United States Patent
Kumar et al.

(10) Patent No.: US 8,652,089 B2
(45) Date of Patent: *Feb. 18, 2014

(54) SYSTEM FOR DISTENDING BODY TISSUE CAVITIES BY CONTINUOUS FLOW IRRIGATION

(75) Inventors: Atul Kumar, Jaipur (IN); Alka Kumar, Jaipur (IN)

(73) Assignee: Arthrex, Inc., Naples, FL (US)

( * ) Notice: Subject to any disclaimer, the term of this patent is extended or adjusted under 35 U.S.C. 154(b) by 1908 days.

This patent is subject to a terminal disclaimer.

(21) Appl. No.: 10/548,950

(22) PCT Filed: Jul. 21, 2004

(86) PCT No.: PCT/IB2004/002341
§ 371 (c)(1),
(2), (4) Date: May 24, 2006

(87) PCT Pub. No.: WO2005/077435
PCT Pub. Date: Aug. 25, 2005

(65) Prior Publication Data
US 2007/0021713 A1    Jan. 25, 2007

(30) Foreign Application Priority Data
Jan. 19, 2004    (IN) .............................. 89/DEL/2004

(51) Int. Cl.
*A61M 1/00* (2006.01)
*A61M 31/00* (2006.01)
*A61B 1/00* (2006.01)

(52) U.S. Cl.
USPC .............................. 604/30; 604/502; 600/101

(58) Field of Classification Search
USPC ...................................... 604/29–35
See application file for complete search history.

(56) References Cited

U.S. PATENT DOCUMENTS

| | | | | |
|---|---|---|---|---|
| 2,689,565 A | * | 9/1954 | Gobel | 604/34 |
| 3,812,855 A | * | 5/1974 | Banko | 604/31 |
| 3,900,022 A | * | 8/1975 | Widran | 600/105 |
| 4,261,360 A | | 4/1981 | Perez | |
| 4,391,599 A | * | 7/1983 | Jenkins | 604/118 |
| 4,613,325 A | * | 9/1986 | Abrams | 604/65 |
| 4,921,477 A | * | 5/1990 | Davis | 604/22 |
| 5,085,658 A | * | 2/1992 | Meyer | 606/46 |
| 5,556,378 A | * | 9/1996 | Storz et al. | 604/31 |
| 5,569,188 A | * | 10/1996 | Mackool | 604/67 |
| 5,586,973 A | * | 12/1996 | Lemaire et al. | 604/19 |
| 5,605,545 A | * | 2/1997 | Nowosielski et al. | 604/118 |
| 5,630,799 A | * | 5/1997 | Beiser et al. | 604/66 |
| 5,776,104 A | * | 7/1998 | Guignard et al. | 604/132 |
| 5,800,383 A | * | 9/1998 | Chandler et al. | 604/35 |

(Continued)

*Primary Examiner* — Kevin C Sirmons
*Assistant Examiner* — Andrew Gilbert
(74) *Attorney, Agent, or Firm* — Dickstein Shapiro LLP

(57) ABSTRACT

The present invention provides a system and a method for distending a body tissue cavity of a subject by continuous flow irrigation such that minimal or negligible fluid turbulence is present inside the cavity, such that any desired cavity pressure can be created and maintained for any desired outflow rate. The present invention also provides a method for accurately determining the rate of fluid loss, into the subject's body system, during any endoscopic procedure without utilizing any deficit weight or fluid volume calculation or flow rate sensor. The system and the methods of the present invention described above can be used in any endoscopic procedure requiring continuous flow irrigation few examples of such endoscopic procedures being hysteroscopic surgery, arthroscopic surgery, trans uretheral surgery, endoscopic surgery of the brain and endoscopic surgery of the spine.

24 Claims, 10 Drawing Sheets

(56) References Cited

U.S. PATENT DOCUMENTS

| | | | |
|---|---|---|---|
| 5,830,180 A * | 11/1998 | Chandler et al. | 604/65 |
| 5,931,808 A | 8/1999 | Pike | |
| 6,030,359 A * | 2/2000 | Nowosielski | 604/65 |
| 6,283,937 B1 * | 9/2001 | Takamatsu et al. | 604/31 |
| 6,302,864 B1 * | 10/2001 | Nowosielski | 604/65 |
| 6,997,896 B2 * | 2/2006 | Novak | 604/67 |
| 7,066,915 B2 * | 6/2006 | Olsen | 604/288.04 |
| 8,226,549 B2 * | 7/2012 | Kumar et al. | 600/156 |
| 8,308,726 B2 * | 11/2012 | Kumar et al. | 606/67 |
| 2004/0030279 A1 * | 2/2004 | Rubenstein et al. | 604/9 |
| 2006/0047185 A1 * | 3/2006 | Shener et al. | 600/156 |

* cited by examiner

SYSTEM FOR DISTENDING BODY TISSUE CAVITIES BY CONTINUOUS FLOW IRRIGATION

FIELD OF INVENTION

The present invention relates to a system for distending body tissue cavities of subjects utilizing continuous flow irrigation during endoscopic procedures. The present invention also provides a method for distending a body tissue cavity of a subject by continuous flow irrigation such that minimal or negligible fluid turbulence is present inside the cavity, such that any desired cavity pressure can be created and maintained for any desired outflow rate. The present invention further provides a method for accurately determining the rate of fluid loss, into the subject's body system, during any endoscopic procedure without utilizing any deficit weight or fluid volume calculation or flow rate sensor. The system and the methods of the present invention described above can be used in any endoscopic procedure requiring continuous flow irrigation few examples of such endoscopic procedures being hysteroscopic surgery, arthroscopic surgery, trans uretheral surgery (TURP), endoscopic surgery of the brain and endoscopic surgery of the spine.

BACKGROUND OF THE INVENTION

Endoscopic Surgery:

Endoscopic surgery is becoming increasingly popular because of the following reasons:
(a) it is a minimally invasive form of surgery,
(b) it avoids large incisions over the skin and muscle,
(c) it is associated with less pain,
(d) there is a relatively less requirement of blood transfusions and
(e) the patients can return back to normal work relatively early with minimal loss of working days.

While in the corresponding open conventional surgeries a relatively large body part consisting of skin and muscle needs to be cut in order to gain access to an underlying body tissue cavity, in endoscopic surgery instead of cutting body structures like skin and muscle an endoscope is introduced into the body cavity via the natural opening of a cavity, if such exists, or alternatively a minute hole is made in the wall of the cavity through which the endoscope is introduced to visualize the interior of the body tissue cavity and to perform major or minor endoscopic surgical procedures. For this reason endoscopic surgery is also sometimes called 'key hole' or 'minimal access surgery'. Besides reducing the pain associated with surgery, endoscopic surgery also helps in reducing the medical expenses.

Endoscopic Surgery is Primarily Related to a Tissue Cavity:

All endoscopic surgeries are carried out on a existing body cavity which is distended or 'ballooned up' by a suitable distending apparatus which permits the inner lining of the said tissue cavity to be visualized by the help of an endoscope. Though multiple endoscopic procedures have become established as the preferred surgical modality but still there is immense scope of increasing the safety and efficiency of the such existing endoscopic procedures by improving upon the existing techniques and apparatus used for distending body tissue cavities. Hysteroscopy, arthroscopy, TURP (transuretheral resection of the prostate), endoscopic surgery of the brain and endoscopic surgery of the spine are few of the routinely performed endoscopic procedures and the organs related to such surgeries being uterus, human joints, bladder, brain and the spine respectively. The list of endoscopic surgeries is long, ever increasing and there is hardly any body organ or organ system to which the benefits of endoscopy have not been extended.

Tissue Cavity is Initially Collapsed in its Natural State:

In the natural state tissue cavities are collapsed structures and the cavity walls are in apposition with each other as if kissing each other. Thus if an endoscope is introduced in such a collapsed cavity no endoscopic visualization is possible unless the cavity is ballooned up by filling it with a transparent fluid or a gas. Such ballooning of a tissue cavity is technically termed as 'cavity distension'. No endoscopic procedure can be performed without an efficient cavity distending system and no endoscopic procedure should be attempted without a safe distending system because unsafe tissue cavity distending means can lead to extreme human morbidity and even the death of a patient and such grim realities shall be discussed in the later sections of this manuscript. Cavity distension provides both endoscopic visualization and mechanical distension which is necessary for the movement of endoscopic instruments.

Continuous Flow Irrigation:

In the present invention, the Inventors are focussed on a system for distending body tissue cavities for those endoscopic procedures in which the cavity needs to be distended by utilizing continuous flow irrigation only. Here, the term 'continuous flow irrigation' means that fluid simultaneously enters and escapes from a tissue cavity via separate entry and exit points, as a result of which a positive fluid pressure is created inside the tissue cavity which distends the cavity.

The Need for Continuous Flow Irrigation:

Any tissue cavity can be easily distended in a 'static manner' by simply pushing fluid via a single inflow tube inserted into the cavity and in this manner a desired cavity pressure can be developed and also maintained. For example, a cavity can be distended by pressing on the piston of a simple syringe filled with fluid with the outlet end of the syringe being connected to the cavity by a tube. Alternatively a fluid filled bottle may be elevated to a suitable height and under the influence of gravity fluid from such bottle may be allowed to enter the cavity via a tube connecting the said bottle to the cavity and in this manner a desired static pressure can be developed and also maintained. Though it is very easy to achieve distension by the said static manner, it is not a practical solution because blood and tissue debris which are invariably released from the fragile cavity inner lining mix with the distending fluid and endoscopic vision gets clouded within a few seconds or a few minutes. Thus continuous flow irrigation is needed to constantly wash away blood and tissue debris in order to maintain constant clear endoscopic vision.

Cavity Pressure and Cavity Flow Rate:

It is obvious that cavity fluid pressure and the flow rate through the cavity are the two basic parameters associated with all continuous flow irrigation systems.

An Efficient Distending System:

The Inventors believe that an efficient distending system is the one which provides a predictably continuous clear visualization and a predictably stable mechanical stabilization of the cavity walls. In order to achieve this the Inventors believe that a suitable stable constant precise cavity pressure and a suitable stable precise cavity flow rate have to be created and maintained in a predictable and controlled manner. The cavity pressure should be adequate so that vision is not clouded by oozing of blood and enough mechanical separation of the cavity walls occurs to allow the movement of the endoscope. Similarly, the cavity flow rate should be adequate enough to constantly wash away blood and tissue debris in order to allow clear vision.

A Safe Distending System:

An efficient distending system as explained in the previous paragraph need not also be a safe distending system. In this regard, the Inventors would like to highlight that if the cavity pressure rises above the prescribed safe limits excessive fluid intravasation may occur or the cavity may even burst. Fluid intravasation is a process by which the irrigation fluid enters into the patient's body system through the cavity walls and may cause significant danger to the patient's life including death. This phenomenon of fluid intravasation has been separately discussed under the heading "Danger of fluid intravasation in hysteroscopy". Thus a safe distending system is one which prevents or minimizes fluid intravasation and does not allow accidental mechanical rupture of the tissue cavity.

No Prior Art is Absolutely Safe:

Many different types of uterine distending systems are known and are being commercially marketed by many different companies but none of these systems can be considered to be absolutely safe for the patient. This fact has been clearly stated in the 'Hysteroscopic Fluid Monitoring Guidelines proposed by the Ad Hoc Committee on Hysteroscopic Fluid Guidelines of the American Association of Gynecologic Laproscopists February 2000 (refer to reference 1 that is Loffler F D, Bradley L D, Brill A I et al: Hysteroscopic fluid monitoring guidelines. The journal of the Americal Association of Gynecologic Laproscopists 7(1): 167-168, 1994) where the authors clearly and explicitly state "fluid pumps for low-viscosity media are a convenience and do not guarantee safety". The present invention aims at providing a distending system which is both safer and more efficient in comparison to all the prior art systems.

Basic Physics of Cavity Distension:

Although, a person skilled in the art may know it, the Inventors would like to provide a brief description of the basic physics of cavity distension. Filling the tissue cavity with fluid enables distension of the same. Initially more fluid is pumped in than the amount which is extracted from the cavity and ultimately the inflow rate is fixed at a level where a somewhat desired cavity pressure and distension is achieved. It may be possible to accurately maintain the desired pressure and distension in the case of a rigid cavity, for example a cavity made of steel.

However, the body tissue cavities are not rigid because they are distensible and also have some element of elasticity. Thus a distended tissue cavity in its attempt to constantly revert back to its natural collapsed state reacts by exhibiting physiological contractions of the cavity wall which generally leads to variations in the cavity pressure which ultimately culminates in irregular movement excursions of the cavity walls. In a static system the said movement excursions may be so minute that they may even go unnoticed. However in a dynamic system such that being created during an endoscopic procedure, the said physiological cavity wall contractions may cause the cavity to expel out its entire fluid content thus leading to a surgically dangerous large magnitude movement excursion of the cavity wall. Because of these reasons it is extremely difficult to maintain the cavity pressure and cavity distension in a predictably stable fashion.

Further, the inflow tube, the out flow tube and the endoscope also invariably move and shake during surgery which leads to variations in fluid flow resistance which is also manifested in the form of variations in the cavity pressure. The cavity pressure variations occurring as a result of cavity wall contractions and the mechanical movement of the tubes and the endoscope tend to occur again even if they are corrected once because it is impossible to prevent the physiological cavity wall contractions and the mechanical movements of the irrigation circuit. Thus, the said cavity pressure variations shall continue to occur even after multiple repeated corrections.

Thus, till date the surgeon was only left with two options, either to ignore the said cavity pressure variations by not correcting them, or to externally and actively correct such pressure variations. The Inventors have noticed that any attempt to externally and actively correct the said cavity pressure variations leads to an undesirable turbulence inside the cavity and also tends to amplify the resultant movement excursions of the cavity walls. Thus there is a grave need to provide a system which can maintain an almost constant and stable cavity pressure even in the presence of the said physiological cavity contractions and the mechanical movements in the irrigation circuit.

BRIEF DESCRIPTION OF AN ENDOSCOPE

Prior to describing the basic layout of a continuous flow irrigation system the basic structure of an 'endoscope' needs to be described. Endoscope is a cylindrical tube having an outer diameter ranging between 3 to 9 mm approximately. A typical endoscope has four channels. One channel is meant to pass a fibereoptic telescope while endoscopic instruments are negotiated through a second instrument channel. A third channel also known as the inflow channel is used for pushing irrigation fluid into a tissue cavity, the proximal end of this channel ending in a metal adaptor known as the inflow port while the distal end of this inflow channel opens near the tip of the endoscope. The inflow port is connectable to an inflow tube which carries sterile irrigation fluid from a fluid source reservoir. A fourth channel also known as the out flow channel is meant for extracting waste fluid out of the cavity, the proximal end of this channel ending in a metal adaptor known as the outflow port while the distal end of this outflow channel opens near the tip of the endoscope. The outflow port is connectable with an outflow tube which transports the waste fluid from the cavity to a suitable waste fluid collecting reservoir. A set of fiber optic bundles contained inside the telescope transmit light energy produced by an external light source. This light energy illuminates the walls of the tissue cavity. The image thus formed is carried via a separate set of optical pathways again situated inside the telescope. A video camera attached to the eye piece of the telescope forms a clear endoscopic image of the cavity on a TV monitor. The endoscopic surgeon has to continuously look at the TV monitor all through the endoscopic procedure.

Basic Layout of a 'Continuous Flow Irrigation System:

Henceforth in this manuscript unless otherwise specified the term 'distension' shall be deemed to imply tissue cavity distension by 'continuous flow irrigation' only and the term 'cavity' unless specifically stated shall be deemed to refer to a 'body tissue cavity'. In a typical distension system a physiological non viscous liquid like 0.9% normal saline, 1.5% glycine, mannitol, ringer's lactate and 5% dextrose is stored in a sterile fluid source reservoir. A fluid supply tube connects the said fluid reservoir with the inlet end of an pump. The outlet end of the inflow pump is connected to the inflow port of an endoscope. When the inflow pump operates the fluid from the fluid source reservoir is sucked via the fluid supply tube and the inflow pump pushes this fluid into the tissue cavity via the said inflow tube. The pump operates by consuming certain amount of energy and as a result of this a positive fluid pressure is created inside the tissue cavity. An outflow tube extends between the outflow port and the inlet end of an outflow pump. When the outflow pump operates it actively extracts waste fluid from the cavity again at the expense of energy and this waste fluid is ultimately sent to a waste fluid reservoir via a tube which connects the outlet end of the outflow pump with the waste fluid reservoir. Alternatively the outflow pump may be missing and in such case the outflow tube directly carries the waste fluid from the cavity to the waste fluid reservoir and the energy for such act is supplied by gravity instead of the outflow pump. Also, the inflow pump may be missing and in such case the inflow tube directly supplies the irrigation fluid from a fluid source reservoir to the cavity. In such case the fluid source reservoir is hung at a suitable height above the patient and the said energy for cavity distension is derived from gravity instead of the inflow pump. A suitable pressure transducer is attached to the inflow tube, the outflow tube or directly to the cavity to measure the fluid pressure. A controller may be incorporated to regulate the system.

The Simplest Continuous Flow Irrigation System:

In its simplest form, a continuous flow irrigation system comprises a fluid reservoir bottle hung at a suitable height above the patient and an inflow tube connecting this fluid reservoir to a tissue cavity. An out flow tube is incorporated to remove fluid from the tissue cavity. In this system there is no pump and no transducer. In such a system fluid flows from the fluid source reservoir into the cavity and the required energy is supplied by gravity. The pressure developed inside the cavity can be increased or decreased by elevating or lowering the height of the fluid source reservoir. In such system the main limiting factor is the height of the room ceiling beyond which the fluid reservoir cannot be raised. This is a crude system having negligible practical importance and has been included only from the academic point of view. Also in such a system unlimited volume of irrigation fluid may enter into the patient's blood circulation. Thus such system is not suitable even from the patient safety point of view.

Basic Components of a Continuous Flow Irrigation System:

Like a motor car is made up of certain obvious components like engine, tyres and a steering wheel, a continuous flow distending system is made of components like pump, pressure transducer, flow regulating valve, rubber tubes and a controller. The pump may be a positive displacement pump like a peristaltic pump, piston pump or a gear pump or alternatively it may be a dynamic pump like a centrifugal pump. Further the said pump may be of a fixed RPM type which runs at fixed RPM all through the endoscopic procedure or the pump may be of a variable RPM type which operates at variable RPM during the endoscopic procedure. It is extremely important to note that fixed RPM pumps and variable RPM pumps are two separate mechanical entities in context with a cavity distending system because the fixed and variable RPM pumps impart different surgical efficiency and patient safety criteria to the distending system. The said pump may be attached on the inflow side only, on the outflow side only or both on the inflow and outflow side. Further if a pump is attached only on the inflow side the outflow tube may directly empty in a waste fluid reservoir at atmospheric pressure or a vacuum source may also be additionally attached. In some distending systems a flow controlling valve is attached on the outflow tube in order to regulate the cavity pressure. There may be a single pressure transducer attached to the inflow tube, the outflow tube or directly to the cavity. In some systems instead of one pressure transducer two pressure transducers may be used, one on the inflow tube and the other on the outflow tube.

Prior Art Documents Categorized According to Type of Pump Used:

Some of the prior art systems use a peristaltic pump on the inflow side while the outflow tube directly drains into a waste collecting reservoir at atmospheric pressure or a vacuum source is attached to it and examples of such systems are seen in U.S. Pat. No. 4,650,462 (DeSatanick et al), U.S. Pat. No. 4,998,914 (Weist et al), U.S. Pat. No. 5,460,490 (Carr et al) and U.S. Pat. No. 6,159,160 (Hsei et al). Some examples of such commercial products are Hamou Endomat (Karl Storz, Tuttinglheim, Germany), Hamou Hysteromat (Karl Storz, Tuttinglheim, Germany), Uteromat Fluid Control of Olympus company, Hystero Pump II 222 of Richard Wolf company, Arthropump (Karl Storz, Tuttinglheim, Germany) and Apex Universal Irrigation System of Linvatec Corporation.

In one of the prior art documents, U.S. Pat. No. 5,152,746 (Atkinson et al) a piston pump has been incorporated on the inflow side while the outflow tube simply drains into a waste collecting reservoir at atmospheric pressure.

In U.S. Pat. No. 5,814,009 (Wheatman) a pneumatic pump situated on inflow side inflates a bladder with air, wherein inflation of said bladder exerts a force against the supply of fluid to deliver fluid there from and the product is commercially marketed as Dolphin II Fluid Management System by ACMI CIRCON. In this system the outflow tube directly empties into a waste collecting reservoir at atmospheric pressure or with a vacuum source attached to it.

In some prior art such as U.S. Pat. No. 5,464,391 (DeVale) and U.S. Pat. No. 6,436,072 (16, 2002 Kullas et al) a centrifugal pump is present on the inflow side while outflow tube may directly drain into a waste collecting reservoir at atmospheric pressure or with a vacuum source attached to it.

In U.S. Pat. No. 5,630,798 (Beiser et al) a centrifugal pump is present on the inflow side and a gear pump is installed on the over outflow side. A commercial product Intelijet System (Smith & Nephew Dyonics Inc, USA) meant for arthroscopy utilizes a centrifugal pump on the inflow side. In one prior art described in U.S. Pat. No. 5,503,626 (1996) the force of gravity is used in the place of an inflow pump while a peristaltic pump is attached on the outflow side. In some prior art systems two peristaltic pumps have been used, one on the inflow side and the other on the outflow side and the examples of such prior art being U.S. Pat. No. 4,261,360 (Perez), U.S. Pat. No. 5,556,378 (Storz et al), U.S. Pat. No. 5,246,422 (Favre) and U.S. Pat. No. 4,902,276 (Zakko). However the prior art related to U.S. Pat. No. 5,246,422 simply provides two peristaltic pumps in a compact confined space and no operating function has been proposed, while the prior art related to U.S. Pat. No. 4,902,276 is meant for a non endoscopic procedure of dissolving gall stones by using two peristaltic pumps which operate intermittently in forward and backward directions and the pressure in the gall bladder is maintained by the opening and closing of multiple valves incorporated in the irrigation circuit. These two prior arts contained in U.S. Pat. Nos. 5,246,422 and 4,902,276 are in not related to the proposed invention but they have been included as references only because in the proposed invention also two peristaltic pumps have been used. The contents of this paragraph have been summarized in table 1 which is as follows:

TABLE 1

| Prior Art | A peristaltic pump on the inflow side | A peristaltic pump on the outflow side | Two peristaltic pumps one on inflow and one on the outflow side | A centrifugal pump on the inflow side | A peristaltic pump on the inflow side and a gear pump on the out flow | A pneumatic pump on the inflow | One pistin pump on the inflow side |
|---|---|---|---|---|---|---|---|
| U.S. Pat. Nos. 4,650,462, 4,998,914, 5,460,490, 6,159,160, Hamou Endomat (Storz), Hamou Hysteromat (Storz), Uteromat Fluid Control (Olympus), Hystero Pump II 222 (Richard Wolf), Arthropump (Storz) and Apex Universal Irrigation System (Linvatec) | Yes | | | | | | |
| U.S. Pat. No. 5,503,626 | | Yes | | | | | |
| U.S. Pat. No. 4,261,360, 5,556,378, 5,246,422 4,902,276 | | | Yes | | | | |
| U.S. Pat. No. 5,464,391, 6,436,072 | | | | Yes | | | |
| U.S. Pat. No. 5,630,798 | | | | | Yes | | |
| U.S. Pat. No. 5,814,009 | | | | | | Yes | |
| U.S. Pat. No. 5,152,746 | | | | | | | Yes |
| Present invention | | | Yes | | | | |

Prior Art Documents Categorized According to Fixed or Variable Pump Flow Rate:

The flow rate of a positive displacement pump like a peristaltic, piston or gear pump is proportional to the pump RPM. In some prior arts an inflow peristaltic pump works at variable flow rate via a pressure feedback mechanism all through the endoscopic procedure. Henceforth in this manuscript any positive displacement which works at a variable flow rate as just described shall be referred to as a 'variable flow rate pump' and any positive displacement pump which works at a constant flow rate through the endoscopic procedure shall be referred to as a 'fixed flow rate pump'. Examples of 'a variable flow rate peristaltic pump' on the inflow side are seen in prior arts such as U.S. Pat. No. 4,998,914 (Weist et al), U.S. Pat. No. 5,460,490 (Carr et al) and U.S. Pat. No. 6,159,160 (Hsei et al) and in some commercial products like Hamou Endomat (Karl Storz, Tuttinglheim, Germany), Hamou Hysteromat (Karl Storz, Tuttinglheim, Germany), Uteromat Fluid Control of Olympus company, Hystero Pump II 222 of Richard Wolf company, Arthropump (Karl Storz, Tuttinglheim, Germany) and Apex Universal Irrigation System of Linvatec Corporation. An example of a fixed flow rate peristaltic pump on the inflow side is seen in U.S. Pat. No. 4,650,462 (DeSatanick et al) and in this system an adjustable flow controlling valve over outflow controls the cavity pressure via a pressure feedback mechanism. An example of a fixed flow rate peristaltic pump on the outflow is seen in U.S. Pat. No. 5,503,626 (Goldrath). An example of a variable flow rate peristaltic pumps on the inflow and on the outflow sides is seen U.S. Pat. No. 1,261,360 (1, 1981, Perez). An example of a fixed flow rate peristaltic pump on the inflow side and a variable speed peristaltic pump on the outflow side is seen in U.S. Pat. No. 5,556,378 (Storz et al). Henceforth in this manuscript a centrifugal pump which operates at variable RPM under the influence of a pressure feedback mechanism shall be referred to as 'variable RPM centrifugal pump'. Examples of 'variable RPM centrifugal pump' on the inflow side are seen in U.S. Pat. No. 5,464,391 (DeVale) and U.S. Pat. No. 6,436,072 (Kullas et al). An example of a system having a 'variable RPM centrifugal pump' on the inflow and a 'fixed flow rate' gear pump on the outflow is seen in U.S. Pat. No. 5,630,798 (Beiser et al). A summary of this paragraph is given in table 2 which is as follows:

TABLE 2 categorizing the prior art on the basis of variable and fixed flow rate pumps:

| Prior Art | A variable flow rate peristaltic pump on the inflow | A fixed flow rate peristaltic pump on the inflow | A fixed flow rate peristaltic pump on the outflow | Variable flow rate peristaltic pumps on the inflow and outflow | Fixed flow rate peristaltic pump on the inflow and a variable flow rate peristaltic pump on the outflow | A variable RPM centrifugal pump on the inflow | A variable RPM centrifugal pump on the inflow and a fixed flow rate gear pump on the outflow | Fixed Flow rate peristaltic pumps on the inflow and on the out flow |
|---|---|---|---|---|---|---|---|---|
| U.S. Pat Nos. 4,998,914, 5,460,490, 6,159,160 Hamou Endomat (Storz), Uteromat Fluid Control (Olympus), Hystero Pump II 222 (Richard Wolf), Arthropump (Storz), Apex Universal Irrigation System (Linvatec) | Yes | | | | | | | |
| U.S. Pat No. 4,650,462 | | Yes | | | | | | |
| U.S. Pat No. 5,503,626 | | | Yes | | | | | |
| U.S. Pat No. 4,261,360 | | | | Yes | | | | |

TABLE 2-continued categorizing the prior art on the basis of variable and fixed flow rate pumps:

| Prior Art | A variable flow rate peristaltic pump on the inflow | A fixed flow rate peristaltic pump on the inflow | A fixed flow rate peristaltic pump on the outflow | Variable flow rate peristaltic pumps on the inflow and outflow | Fixed flow rate peristaltic pump on the inflow and a variable flow rate peristaltic pump on the outflow | A variable RPM centrifugal pump on the inflow | A variable RPM centrifugal pump on the inflow and a fixed flow rate gear pump on the outflow | Fixed Flow rate peristaltic pumps on the inflow and on the out flow |
|---|---|---|---|---|---|---|---|---|
| U.S. Pat No. 5,556,378 | | | | | Yes | | | |
| U.S. Pat Nos. 5,464,391, 6,436,072 | | | | | | Yes | | |
| U.S. Pat No. 5,630,798 | | | | | | | Yes | |
| The present invention | | | | | | | | Yes |

Prior Art Documents Categorized on the Basis of Adjustable Flow Controlling Valve on the Outflow Tube:

In some prior arts such as U.S. Pat. No. 4,650,462 (DeSatanick et al) and U.S. Pat. No. 5,460,490 (Carr et al) an adjustable flow controlling valve on the outflow tube is used for regulating the cavity pressure.

Before describing the physical principals of some of the important prior art systems and their drawbacks, hysteroscopic surgery, TURP surgery and Arthroscopic surgery shall be briefly described especially in context with fluid intravasation, the importance of constant clear visualization, the importance of cavity wall stabilization and the relevance of physiological cavity wall contractions. The concepts of reducing cavity refilling time, intraoperatively switching between two different types of irrigation fluids and predicting the required volume of irrigation fluid shall also be described.

Hysteroscopic Surgery:

In the word hysteroscopy 'hyster' means the uterus and 'scopy' means visualization, thus the term hysteroscopy meaning visualization of the of the uterine cavity. The uterus is also commonly known as the woman's womb. Hysteroscopy is a very useful technique as diagnoses and treats a large number of gynecologic diseases without the need of removing the woman's womb. Some common hysteroscopic procedures are TCRE (Trans Cervical Resection of the Endometrium which is commonly also referred to as 'endometrial resection'), fibroid resection, polyp resection, adhesiolysis, septoplasty, hysteroscopic tubal cannulation and visually targeted endometrial biopsy. Procedures like septolpasty, sub mucous fibroid resection and visually guided adhesiolysis can be accomplished only by hysteroscopic means and in such procedures utilization of the old conventional open surgical techniques may be considered illogical and may also invite medico legal action.

Anatomy of the Uterus:

The uterus is a hollow pear shaped organ having an approximately 5 mm to 20 mm thick muscular wall which encloses the uterine cavity. In a young nulliparours woman the uterus measures about 8 cm in the long length, about 5 cm in the transverse diameter and about 5 cm in the antero posterior axis. The hollow cavity present inside the uterus is known as the uterine cavity. The uterine cavity opens into the vagina via its natural opening known as external os. During hysteroscopy the uterine cavity is distended by pushing fluid through the natural opening of the uterus. The uterine cavity is lined by a 2 to 6 mm thick, delicate and fragile, tissue membrane known as the endometrium. The fertilized egg implants over the endometrium and subsequently a completely developed fetus is delivered through the natural opening of the uterus.

Cavity Distension in Hysteroscopy:

The uterine cavity can be distended by pushing fluids or carbon dioxide gas into the cavity. Carbon dioxide gas has a limited use in few diagnostic procedures while the major hysteroscopic procedures require the uterine cavity to be distended only by continuous flow irrigation. Thus the use of gas has largely been abandoned in favor of physiological non viscous liquids like 0.9% normal saline, 1.5% glycine, mannitol, ringer's lactate and 5% dextrose. Proper distension of the uterine cavity is the primary requirement for safe and accurate completion of all hysteroscopic procedures. Uterine distension, if not done properly, may lead to dangerous surgical complication like fluid overload resulting from excess fluid intravasation (see references 2,3 i.e. Olsson J et. al, "Early detection of the Endometrial Resection Syndrome" Gynecol Obstet Invest 42: 142-4, 1996 and Roesch R P et. al, "Ammonia toxicity resulting from glycine absorption during a transuretheral resection of the prostrate" Anesthesiology 58: 577-79, 1983) and other complications like uterine perforation.

Fluid overload may culminate in the patient's death by a process known as TUR syndrome.

Need for Continuous Flow Irrigation in Hysteroscopy:

While performing hysteroscopic surgery, an endoscope is first inserted into the uterine cavity. Next, fluid is pushed into the uterine cavity via an inflow tube attached to the inflow port of an endoscope. Due to the resultant accumulation of fluid the uterine cavity distends and an endoscopic image of the uterine cavity is seen on a TV monitor. The inner lining of the uterine cavity, technically known as the endometrium, is a very delicate membrane which readily bleeds even on being minutely touched by the endoscope or during surgery and this released blood causes clouding of endoscopic vision because blood being opaque impairs the passage of light. Thus, in order to maintain a clear vision the dirty blood mixed fluid from the uterine cavity by constantly replacing with fresh clear fluid by the said process of 'continuous flow irrigation'. 'Continuous flow irrigation' is thus a method of distending a tissue cavity in such a manner that fluid is continuously instilled into the cavity, while an equal amount of fluid is being constantly removed out of the cavity.

The Need of Maintaining Predictably Almost Constant Precise Uterine Cavity Pressure:

In hysteroscopic surgery and in all other related surgeries utilizing continuous flow irrigation it is extremely important to a maintain predictably almost precise constant cavity pressure all through the surgery because a predictably stable cavity pressure helps in attaining a predictably stable mechanical stabilization of the cavity walls.

Minimum Turbulence is Desirable:

In the nature of the fluid flow through the cavity is turbulent tissue debris shall continuously float in the cavity in an irregular fashion thus obstructing visualization and it also decreases the mechanical stabilization of the cavity walls by encouraging irregular cavity wall movement excursions. Thus, the cavity fluid turbulence should be relatively less and preferably should be reduced to almost negligible levels.

Fluid Pressure Should be Independent of the Flow Rate:

In technical terms it should be possible to create and maintain any desired precise tissue cavity pressure for desired constant outflow rate including a zero outflow rate. This statement an be alternatively stated by saying that cavity pressure has to be made absolutely independent of the cavity flow rate. In hysteroscopic surgery it is essential to have a distending system in which four different types of combinations between 'cavity pressure' and 'cavity flow rate' can be achieved and such combinations are described in table 3 which is as follows:

TABLE 3

| A DESIRED RELATION BETWEEN CAVITY PRESSURE AND CAVITY FLOW RATE | ADVANTAGES OF SUCH A RELATIONSHIP | DISADVANTAGES OF SUCH A RELATIONSHIP |
| --- | --- | --- |
| Low cavity pressure at low flow rate | Reduces the overall volume of fluid intravasation and also reduces the risk of an accidental excess fluid intravasation | Adequate distension may not be achieved, blood may ooze and tissue debris may not be removed quickly |
| Low cavity pressure at high flow rate | Reduces the overall volume of fluid intravasation and helps in quick evacuation of tissue debris and blood | Adequate distension may not be achieved, blood may ooze |
| High cavity pressure at low flow rate | Helps in attaining a better mechanical distension of the cavity, helps in preventing oozing of blood by pressure temponande and reduces the risk of an accidental excess fluid intravasation | The overall volume of intravasation may be relatively high |
| High cavity pressure at high flow rate | Helps in attaining a better mechanical distension of the cavity, helps in preventing oozing of blood through pressure temponande and helps in quick evacuation of tissue debris and blood | The overall volume of intravasation may be relatively high and the risk of an accidental excess fluid intravasation may also be relatively high |

(Note:
The concepts of 'fluid intravasation' and 'accidental excess fluid intravasation' have been described in the next two paragraphs).

The surgeon may need to switch between the said four combinations multiple times in the same endoscopic procedure. The said four combinations between pressure and flow rate need to be utilized in other endoscopic procedures utilizing continuous flow irrigation also such as TURP and arthroscopy. In the present invention besides many other benefits the said four combinations between pressure and flow rate are possible to achieve, because in the present invention the cavity pressure is made absolutely independent of the cavity flow rate.

Danger of Fluid Intravasation in Hysteroscopy:

In continuous flow irrigation the rate at which the fluid enters into the uterine cavity via the inflow tube is known as the inflow rate while the rate at which fluid escapes from the uterine cavity via the outflow tube is known as the outflow rate. As a result of continuous flow irrigation a positive pressure develops due to which the uterine cavity distends. Normally a cavity pressure of 50 to 100 mm Hg pressure is sufficient to distend the uterine cavity. In some hysteroscopic procedures like 'endometrial resection' multiple small blood vessels are cut and the pressure in the lumen of such cut blood vessels may be as low as 5 mm Hg while the intrauterine pressure usually ranges between 50 to 100 mm Hg, thus a positive pressure gradient always exists between the uterine cavity and the lumen of the cut blood vessels. In accordance with the known laws of physics, under the influences of the said pressure gradient the pressurized cavity fluid constantly enters into the systemic circulation of the patient via the said cut ends of the blood vessels and such process is commonly termed as 'fluid intravasation'. In case of an accidental mechanical rupture of the uterine cavity wall (uterine perforation) the cavity fluid enters into the abdominal cavity (peritoneal cavity) through the perforation site. The intravasation rate in the case of uterine perforation can be very high, as the pressure inside the abdominal cavity is very low, almost equal to the atmospheric pressure. In most major hysteroscopic procedures '1.5% glycine fluid' is used to distend the uterine cavity however excess intravasation of such fluid may be dangerous as it leads to an increase in the circulating blood volume (hypervoluemia), a decrease in the blood osmolarity (hypoosmolarity) and a reduction in the blood sodium ion concentration (hyponatremia) all of which combined together constitute a clinical syndrome known as TUR syndrome which may even culminate in the patient's death. TUR syndrome is so named as this syndrome was initially observed in TURP surgery which is a similar procedure like hysteroscopic endometrial resection. It is to be noted that in TURP also multiple small blood vessels are cut as in endometrial resection. It is important to know and limit the volume of the intravasated fluid to as minimum as possible, as excessive absorption of any type of irrigation fluid is dangerous and may even culminate in mortality.

Increased Inflow Rate Increases the Risk of Accidental Excess Intravasation in Hysteroscopy:

In continuous flow irrigation fluid enters the cavity at some flow rate which commonly termed as the 'inflow rate' while simultaneously fluid escapes from the cavity at some flow rate commonly termed as the 'outflow rate' and as a result of these two processes a positive fluid pressure developed inside the cavity. As stated in the previous paragraph the pressure inside the venous blood vessels and inside the abdominal cavity is very low thus if large diameter veins are accidentally cut or if a perforation occurs then almost the entire fluid which is entering the cavity via the inflow tube can enter into the patient's blood circulation or into the abdominal cavity. Henceforth in this manuscript the maximum flow rate at which the irrigation fluid may enter into the patient's body system shall be termed as the 'maximum possible intravasation rate'. Thus the 'maximum possible intravasation rate' is almost equal to the maximum possible or permissible inflow rate. Both positive displacement pumps such peristaltic pumps and the dynamic pumps such as centrifugal pumps carry the risk of high 'maximum possible intravasation rate'. As explained in the subsequent paragraph under the heading "Centrifugal Pump on the Inflow" in the systems having a peristaltic pump on the inflow side the 'maximum possible intravasation rate' is reduced or limited by fixing the maximum RPM beyond which the pump cannot operate but this is usually achieved at the expense of reducing the value of the maximum cavity pressure which the system can generate. In the systems which incorporate a centrifugal pump on the inflow side the 'maximum possible intravasation rate' is high because in centrifugal pumps the pump flow rate and the pressure head are related in a parabolic manner. In the eventuality of an accident like cavity perforation the pump outflow rate becomes very high because the pressure head may becomes almost zero. In centrifugal pumps the 'maximum possible intravasation rate' can be reduced or limited by fixing the maximum RPM beyond which the centrifugal pump cannot operate but again this is achieved at the expense of reducing the value of the maximum cavity pressure which the system can generate. This has been explained in the same paragraph. Hypothetically assuming an inflow rate of 500 ml/minute, in such a situation, the patient can absorb up to 5 liters of fluid in just 10 minutes, which in all probability would culminate in the patient's death. Thus it would be definitely much safer to use a uterine distending system in which the cavity pressure could be increased and maintained at any desired value without increasing the inflow rate and without allowing the inflow rate to increase at any time.

Measurement of Instantaneous Real Time Rate of Fluid Intravasation Increases Patient Safety:

According to the 'Hysteroscopic Fluid Monitoring Guidelines proposed by the Ad Hoc Committee on Hysteroscopic Fluid Guidelines of the American Association of Gynecologic Laproscopists (see reference 1) fluid absorptions greater than 750 ml may be dangerous to the patient's life. In many prior art systems the total volume of fluid absorbed into the patient's body is determined by substracting the volume or weight of waste fluid present in a waste fluid collecting reservoir from the volume or weight of the sterile irrigation fluid which was initially present in the fluid source reservoir and a average rate of intravasation is calculated by dividing the determined fluid deficit by the total time taken for the said intravasation to occur. In this manner the magnitude of rate of intravasation is assessed only after the complication of intravasation has occurred and such system does not provide the safety of preventing intravasation from occurring. In the eventuality of an excessive intravasation having occurred the surgeon can only treat the patient to the best of his abilities but the despite such efforts there can be significant morbidity or even mortality. In some prior art systems efforts have been made to determine the volume of intravasated fluid by measuring the weight of the fluid in the fluid source reservoir and the weight of the fluid present in a waste fluid collecting vessel and subtracting the latter weight from the former weight. The just stated method of determining the volume of fluid intravasation are described in prior arts such as U.S. Pat. No. 5,492,537 (Vancaillie), U.S. Pat. No. 5,556,378 (Storz et al), U.S. Pat. No. 5,814,009 (Wheatman), U.S. Pat. No. 5,921,953 (Novak) and U.S. Pat. No. 5,503,626 (Goldrath). However if the instantaneous real time rate of fluid intravasation is constantly known all through surgery then necessary preventive actions, including abandoning the surgery, can be take by the surgeon within a few seconds after sudden increase in the rate of intravasation is detecting and in this manner the dangerous complication of excess fluid intravasation can be prevented from occurring. The instantaneous rate of fluid intravasation can be determined by incorporating one fluid flow rate sensor on the inflow tube and one fluid flow rate sensor on outflow tube and subtracting the flow rate value of the outflow sensor from the flow rate value of the inflow sensor. Theoretically this appears to be a simple task but practically it is very difficult, especially in context with endoscopic surgery where reliability, accuracy and sterility are important criteria. Many types of external or internal flow rate sensors working on mechanical or electromechanical principals are known as of today but their accuracy and reliability, especially where the irrigation fluid is non viscous and transparent in nature, is a debatable issue. Thus in the said context only that sensor can be permitted to be used which is absolutely reliable and very accurate because a malfunction or inaccurate measurement of the said sensor may culminate in patient morbidity or even mortality. In German Patent No. 4417189 A1 (Meyer Edgar et al.) a mechanical flow rate sensor has been proposed to be incorporated inside the lumen of the inflow tube to determine the inflow rate while the outflow rate is determined by noting the flow rate of a peristaltic pump installed on the outflow side. It is also to be noted that any flow sensor which is installed inside the lumen the irrigation tubes also poses considerable practical difficulties with respect to maintaining a sterile bacteria free environment. Thus it is highly desirable to have a system of reliably and accurately determining the instantaneous real time rate of fluid intravasation without incorporating any kind of flow rate sensor either inside or outside the lumen of the irrigation tubes, however such a system is not present in any of the prior art systems. Thus the Inventors believe that it would be beneficial to continuously and in a reliable and accurate manner to determine the real time rate of fluid intravasation without using any kind of fluid flow rate sensor.

The Significance of the Actual Cavity Pressure in Hysteroscopy:

As already stated previously fluid intravasation occurs due to a positive pressure gradient which inadvertently exists between the pressurized cavity fluid and the lumen of the cut blood vessels, especially the veins. Thus, any increase in the uterine cavity pressure increases the rate of fluid intravasation by promoting the entry of the irrigation fluid through the cut ends of the blood vessels. There are two types of blood vessels, veins and arteries. While the blood pressure inside the veins is as low as 5 mm Hg the blood pressure inside the arteries may be as high as 100 mm Hg. Considering a hypothetical situation where the pressure inside an artery being 100 mm Hg, the pressure inside a vein being 5 mm Hg and the uterine cavity pressure being 80 mm Hg. In such situation, if both veins and arteries are cut the blood oozes out through the arteries while the pressurized irrigation fluid enters into the veins through their cut ends. If larger diameter veins are accidentally cut intravasation may occur at a dangerously high rate and the literature has many case reports in which mortalities occurred due to such accidents. Usually the surgeons do not like increase the uterine cavity pressure beyond the mean arterial pressure of the patient, but such maneuver is only possibly if the actual cavity pressure is known. In order to avoid excess intravasation the surgeon works at the minimum allowable intrauterine pressure at which there is no bleeding and the cavity is also adequately distended to allow free movement of endoscopic instruments. Fluid intravasation being directly related to the cavity pressure it is becomes essential for the surgeon to know the actual pressure which exists inside the uterine cavity. The actual cavity pressure can be measured by directly placing a pressure transducer inside the cavity or by inserting a catheter directly into the cavity with a transducer being attached at the distal end of the catheter such that the transducer measures a true static pressure, but such maneuvers are tedious and practically difficult. In many prior art systems a pressure transducer is attached at the upstream part of the inflow tube but such transducers may read a pressure which is higher than the actual cavity pressure due to mechanical frictional imposed by the inner surface of the inflow tube to the moving fluid column, a phenomenon which has been explained in detail in subsequent paragraphs. Further the cavity wall also exhibits physiological contraction movements which causes the cavity pressure to fluctuate in an irregular fashion and such pressure fluctuations are overcorrected or under corrected by the prior art systems which makes it even more difficult to determine the actual cavity pressure. The irrigation pipes and the endoscope are also constantly moving or shaking which continuously varies the overall resistance to fluid flow thus leading to fluctuations in the cavity flow rate which again causes in cavity pressure fluctuations. In the prior systems as described in U.S. Pat. No. 4,998,914 (Weist et al) and U.S. Pat. No. 5,556,378 (Storz et al) the cavity pressure determined by considering flow resistance, flow rate and the sensed pressure.

The Need of Predictably Continuous Clear Visualization in Hysteroscopic Surgery:

A predictable and continuous clear visualization is extremely essential for all types of hysteroscopic procedures but the importance of clear vision shall be explained especially in context with Endometrial Resection which is a classical representative of major hystroscopic procedures. Endometrial resection is performed in those women who suffer with excess blood loss during their menstrual periods and this procedure is an extremely physiological alternative to hysterectomy (removal of the uterus) because in endometrial resection the uterus is not needed to be removed form the woman's body. Thus it is thus an organ conserving surgery. It is to be noted that each year lakhs of women undergo hysterectomy and endometrial resection can avoid hysterectomy in many such cases. In this procedure the entire inner lining of the uterine cavity, the endometrium, is cut electrosurgically along with an adequate thickness of the underlying myometrium. Myometrium is the muscular wall of the uterine cavity and the roots of the endometrial glands penetrate into the myometrium to variable depths ranging from 1 to 4 mm but in some situations like adenomyosis the endometrial glands may be seen penetrating deeper up to 10 mm or even more. Considering a hypothetical case in which most endometrial glands penetrate up to a depth of 3 mm while few glands are found to be growing much deeper into the myometrium. If such deep penetrating glands are not removed during endometrial resection they may again regenerate and the patient may again develop the initial disease of excessive menstrual bleeding. Thus it is important to either completely remove or destroy all the endometrial glands and in order to accomplish this the surgeon has to precisely identify and target the openings of such glands before elecrtrosurgically cutting such glands to the required depth, while simultaneously coagulating the cut ends of large diameter blood vessels if encountered, talking extreme care to avoid a blood hemorrhage or excess intravasation. Any accidental deep cut into the myometrium at this stage may lead to a life threatening fluid intravasation or a hemorrhage. Such precision and fine surgery is only possible if a predictably continuous clear endoscopic vision is available all through surgery. In the absence of clear visualization accidents like cavity wall perforation can also occur. The importance of continuous clear vision cannot be over emphasized and it is one of the most important requirements for safety and efficiency for every endoscopic surgical procedure.

The Need of Cavity Wall Stabalization in Hysteroscopic Surgery:

As already stated, the uterine cavity wall exhibits physiological contraction movements which produce variations in the cavity pressure but such pressure fluctuations are amplified on being constantly corrected by the prior art systems which culminates into significant undesirable movement excursions of the cavity wall. Further the irrigation pipes and the endoscope are also constantly moving or shaking which produces minute variations in the overall resistance to fluid flow which causes minute fluctuations in the cavity pressure which is also corrected, over corrected or under corrected as just stated and further ads to the magnitude of the resultant cavity wall movement excursion. Let us take a hypothetical example where the intramural part of the fallopian tube is being cut during a procedure of endometrial resection. The total cavity wall thickness around the intramural part of the fallopian tube is about 2 mm, thus a cavity wall movement excursion of 3 mm shall lead to the perforation of the cavity wall which may culminate into a serious injury as high voltage electrosurgical currents are also used in the process. Thus it is highly desirable to mechanically stabilize the cavity wall and to limit the magnitude of cavity wall movement excursions to as minimum as possible, however such movements cannot be totally eliminated.

The Concept of Reducing Cavity Refilling Time:

In hysteroscopic surgery and in many other endoscopic surgeries like TURP the resectoscope needs to be withdrawn multiple times during the endoscopic procedure either to remove the resected tissue pieces or in order to change the operating instruments. Each time the resectoscope is removed the entire cavity fluid spills out of the cavity and when the resectoscope is reintroduced it takes time for the cavity to again completely fill up with fluid and the magnitude of such time depends upon the cavity volume capacity and the inflow rate. For example in TURP surgery the urinary bladder having a substantially high volume capacity, about 300 ml, the time taken for the bladder to completely fill is also relatively high. A similar situation is seen in a large size uterus where the cavity volume may be high. Thus a lot of valuable surgical time is wasted in repeatedly filling the cavity with fluid because during the cavity refilling phase definitive surgery cannot be done as proper visualization may not be available in a partially filled cavity. The time taken for an empty cavity to completely fill up with the irrigation fluid shall henceforth be referred to as the 'cavity refilling time' and the time phase in which the cavity is being filled shall being termed as the 'cavity refilling phase'. If the 'cavity refilling time' is somehow reduced the total surgical time can be significantly shortened. In the present invention besides many other benefits the said 'cavity refilling time' can be varied, that decreased or increased, by any desired magnitude in a predictably controlled and safe manner.

Intraoperatively Switching Between Two Types of Irrigation Fluids:

In routine practice, at the beginning of an endoscopic procedure the surgeon chooses a suitable type of irrigation fluid. As already mentioned in the above paragraph physiological non viscous liquids like 0.9% normal saline, 1.5% glycine, mannitol, ringer's lactate and 5% dextrose are used for distending tissue cavities. Such fluids have been termed 'physiological' as their use is permitted in endoscopic surgeries however all said fluids are not totally physiological in the true sense of the meaning because absorption of such fluids does lead to physiological imbalances and even mortality if absorbed in excess. However certain fluids like 0.9% normal saline are considered relatively more physiological than some fluids like 1.5% glycine. Ionic fluids like 0.9% normal saline and ringer's lactate, being isotonic and isoosmolar with respect to blood, are considered relatively more physiological in comparison to the non ionic fluids like 1.5% glycine, mannitol and 5% Dextrose which are hypotonic and hypoosmolar with respect to blood. Henceforth the term normal saline shall imply a 0.9% normal saline solution and the term glycine shall imply 1.5% glycine because fluids of such concentrations are routinely used as irrigation fluids. The osmolarity and sodium ion concentration of blood plasma is 290 mosmol/L and 137 milli equivalent/L respectively, while the osmolarity and sodium ion concentration of 0.9% normal saline solution is 308 mosmol/L and 154 milli equivalent/L respectively. Thus even if an excess volume of normal saline is absorbed into the systemic circulation it does not cause hyponatremia (decrease in sodium concentration) or hypoosmolarity (decrease in osmolarity). However excess absorption of normal saline may lead to hypervolemia (an increase in the circulating blood volume) which is relatively less dangerous complication when compared to hyponatremia and hypoosmolarity and can corrected in a short time by administering intravenous diuretics. It is for this reason that 0.9% solution of sodium chloride is the fluid of first choice whenever the surgical procedure permits its use. On the other hand the osmolarity of 1.5% glycine solution is only 200 mosmol/L and it is totally deficient in sodium ions. Hence excess absorption of 1.5% glycine leads to a complication known as TUR syndrome as it was first observed in TURP. TUR syndrome comprises of mainly three types of physiological imbalances namely hyponatremia, hypoosmolarity and hypervolemia. If the patient develops TUR syndrome the water from the circulating blood enters into the brain and lung cells and the patient may die due to resultant brain edema and lung edema, besides many other physiological aberrations being caused. However the use of 1.5% glycine fluid is a necessary evil as certain underwater monopolar electrosurgical procedures can only be carried out by using such non ionic fluids. Also, the severity of physiological imbalance caused by glycine absorption is directly related to the total volume of glycine absorbed. Normal saline is a physiologically safer to use but it cannot be used in those surgical procedures which utilize monopolar electrosurgery as in endometrial resections and prostate resections where monopolar electrosurgery is utilized to cut the diseased tissue. Sodium ions make normal saline a good conducter of electricity. For this reason monopolar electrosurgery cannot be done by using normal saline because the sodium ions dissipate the electrical energy in all directions which does not allow the entire monopolar electrical energy to pass through a specific target location which in turn does not allow production of localized intense heat by which tissue is cut in monopolar electrosurgical procedures. 1.5% Glycine being deficient in sodium ions does not conduct electricity thus intense heat can be concentrated at a target point during monopolar electrosurgical procedures. On the other hand certain bipolar underwater electrosurgical procedures, like those done with the help of a bipolar versapoint generator, can be carried out only in the presence of sodium ions present in normal saline because in such procedures heat energy can be localized at the tip of an electrode only in the presence of sodium ions. Thus if monopolar electrosurgery is contemplated then non ionic fluids like 1.5% glycine are chosen at the beginning of the surgery. In case no electrosurgery is contemplated or a bipolar underwater type of electrosurgery is contemplated then ionic fluids like normal saline are chosen at the beginning of the endoscopic procedure. However during surgery situations may arise which require changing from an ionic fluid to a non ionic fluid and vice versa, for example switching between normal saline and glycine or vice versa. Few such situations are mentioned as follows:

1. If at the beginning of the procedure electrosurgery is not contemplated then normal saline is chosen, but if after the introduction of the endoscope an intracavitatory pathology is seen which needs to be treated by monopolar electrosurgery then it is necessary to change from normal saline to glycine.
2. If at the beginning of the endoscopic procedure no electrosurgery is contemplated or if underwater type of bipolar surgery is contemplated then normal saline is initially chosen, however if an intracavitory pathology is subsequently discovered which needs to be treated by monopolar electrosurgery then the initially taken normal saline has to be replaced by glycine in order to carry out monopolar electrosurgely.
3. In certain endoscopic procedures like endometrial resection which utilize monopolar electrosurgery glycine is used for cavity distension. In such procedures considerable time may be spent in removing the resected tissue pieces under endoscopic vision by grasping mechanically with the cutting loop and during such maneuver unnecessararily an extra volume of glycine is absorbed into the patient's body. If during such time while the tissue pieces are being taken out glycine is substituted by normal saline then relatively less glycine is absorption for the same total volume of fluid absorbed and this causes a relatively lesser harm to the patient because in such case a considerable part of the absorbed fluid consists of a relatively more quantity of the more physiological normal saline fluid.

Switching between two types of irrigation fluids as mentioned above essentially requires that the entire fluid present in the irrigation circuit consisting of the inflow tube and the tissue cavity is replaced by flushing with a second type of irrigation fluid. The fluid initially chosen at the beginning of surgery is being referred to as the 'first fluid' and the later chosen fluid by which the irrigation circuit needs to be flushed is being referred to as the 'second fluid'. The degree of contamination of the second fluid by the molecules of the first fluid is being termed as the 'purity' of the second fluid, the second fluid being considered 100% pure if it has no molecules of the first fluid present in it but such situation cannot be attained practically. Considering a first hypothetical situation where normal saline being the first fluid needs to be replaced by glycine as the second fluid, in such a case the flushing of the irrigation circuit has to continue till the purity of the second fluid glycine reaches a threshold level at which the degree of contamination of second fluid glycine by sodium ions is so less that for all practical purposes the second fluid glycine does not conduct electricity and the said threshold level of purity can be determined experimentally. Practically even with rigorous flushing it may not be possible to have a zero concentration of sodium ions in the second fluid glycine thus flushing is done only to the extent that the purity of the second fluid glycine is increased to the said minimum threshold level at which the electrical conductivity of the second fluid glycine is low enough to allow monopolar electrosurgery to be carried out. The time taken for such flushing to be completed is being termed as the 'flushing time'. In physical terms the said flushing is achieved by instilling the second fluid through the inflow tube while the first fluid is allowed to escape through the out flow tube and such process is continued till the desired purity threshold level is achieved in the second fluid glycine. Now considering a second hypothetical situation in which the first fluid glycine needs to be replaced by the second fluid normal saline in order to permit bipolar electrosurgery, in such case the process of flushing is continued till the concentration of the second fluid normal saline increases to a minimum threshold concentration of sodium ions at which bipolar electrosurgery is possible to performed. In the just mentioned first and second hypothetical situations the required flushing time decreases if the flushing flow rate during the flushing phase is increased. A low flushing time is highly desirable as the surgeon does not have to wait unduly long for the process of flushing to complete. A short flushing time thus shortens the total surgical time. However a relatively shorter flushing time requires that the second fluid should flow through the inflow tube and the tissue cavity at a suitably high flow rate during the flushing phase but such high fluid flow rate may create a dangerously high pressure inside the tissue cavity. If the flushing time can be shortened without increasing the cavity pressure then such maneuver of shortening the flushing time can be very helpful in endoscopic procedures like endometrial resection, TURP and arthroscopy as it empowers the surgeon to minimize the patient's exposure to a relatively less physiological fluids and it also allows the surgeon to choose between different types of irrigation fluids during the same endoscopic procedure. Thus a system is desired in which the flushing time can be reduced in a desired controlled manner by temporarily increasing the flow rate through the irrigation circuit such that the cavity pressure does not change during such maneuver.

Predicting the Total Volume of Required Irrigation Fluid:

In endoscopic procedures the irrigation fluid to be used in surgery is usually contained in fluid bottles which are hung on a stand or alternatively the irrigation fluid is kept inside a sterile fluid source container. If the irrigation fluid finishes during surgery it wastes substantial valuable surgical time while a fresh supply of the irrigation fluid is replaced and during this time blood clots might accumulate in the cavity subsequent to the loss in cavity distension. Such clots have to be removed because they impair visualization, thus making surgery difficult and longer. It is difficult to remove such clots as they may spread diffusely over the entire cavity surface. All this can be avoided if before starting the surgery or at any time during the course of surgery the total volume of irrigation fluid required to complete the surgery could be predicted, so that exactly the same volume of fluid could be taken in one single attempt. By such maneuver surgery is not disrupted at any moment on account of changing fluid bottles or the fluid in the fluid source container. The irrigation fluid which is at room temperature has to be warmed to match the body temperature and this takes time. Thus if the expected total requirement of irrigation fluid is known the same can be warmed to body temperature and the surgeon shall not have to stop surgery in between while the fluid warms to body temperature. Such a provision of predicting the total required fluid volume can be very helpful in endoscopic procedures like endometrial resection and transuretheral resection of the prostate.

TURP:

TURP (Trans utretheral resection of the prostate gland) is a commonly performed urologic procedure which is also a classical representative of transuretheral endoscopic procedures. TURP is a very frequently performed procedure in men of the older age group who usually present with urinary retention due to enlargement of the prostate gland. The general principles and problems related to cavity distension are similar in TURP and hysteroscopic surgery. In TURP an endoscope is introduced through a natural opening known as the uretheral meatus. Urethral meatus is the natural opening via which urine is expelled during micturation. As the resectoscope is advanced through the male urethera the prostate gland and the bladder cavity are subsequently visualized and if the prostate gland is found enlarged it is resected electro surgically and the surgical procedure is known as TURP. Hysteroscopic endometrial resection and TURP surgery are similar in light of the fact that in both surgeries multiple blood vessels are inadvertently cut and the irrigation fluid has a grave potential to intravasate into the systemic circulation through the cut end of such blood vessels, thus leading to a dangerous physiological aberration known as the TUR syndrome. The mechanism of fluid intravasation in TURP is same as in hysteroscopic surgery as explained above. Also it is clearly mentioned in Campbells Text Book of Urology 2002 (see reference 4 i.e. Campbells Text Book of Urology 2002, $8^{th}$ edition Edited by Patrick C Walsh page 1409) that during routine TURP surgeries the patient can absorb fluid at an alarming rate of 20 ml/minute. Thus it is important to know the real time rate of fluid intravasation in TURP surgery as well. Multiple references of the dangers of fluid intravasation in TURP surgery are found in the literature. All the features related to continuous flow irrigation discussed in context with hysteroscopic surgery are equally relevant in context with TURP surgery also and in order to avoid repetition the same is not being discussed again.

Arthroscopy:

Arthroscopy means visualization of the joint cavity. The basic principals of cavity distension in arthroscopy, hysteroscopy and TURP surgery are almost similar. All the features related to continuous flow irrigation discussed in context with hysteroscopic surgery are equally relevant in context with arthroscopic surgery also and in order to avoid repetition such features shall not be again discussed. A predictably constant clear visualization, a predictably stable mechanical stabilization distension of the joint cavity and maintenance of joint cavity pressure totally independent of the outflow rate are few important requirements for safe and efficient arthroscopic surgery. In Campbells Text Book of Operative Orthopeadics 2003 (see reference 5 i.e. Campbells Text Book of Operative Orthopeadics 2003, $10^{th}$ edition, Volume 3, Edited by S Terry canale, page 2504) it is clearly mentioned that proper distension of the joint cavity is essential for any type of arthroscopic viewing and the problems of fluid extravasation are also clearly highlighted. In arthroscopic surgery the irrigation fluid can escape into the tissues surrounding the joint and such complication is termed as fluid extravasation. Thus fluid extravasation which occurs in arthroscopy is similar to the 'fluid intravasation' which is observed in hysteroscopy and TURP with the difference between the two being that 'intravasation' is a broad term while 'extravasation' related to fluid which diffuses into the tissues surrounding a tissue cavity. Thus in this manuscript the term 'intravasation' shall also be deemed to include the phenomenon of 'extravasation'. The extravasated fluid compresses the blood vessels which results in a reduced blood supply to vital structures like motor or sensory nerves which may temporarily or permanently damage the nerves. Thus fluid extravasation is one the major complications of arthroscopy. The real time evaluation of the rate of intravasation (extravasation in the case of arthroscopy) which is a unique feature of the present invention can be very helpful in avoiding or minimizing fluid extravasation during arthroscopy. Arthropump plus (Karl Storz, Tuttinglheim, Germany) is a popular prior art system used for distending the joint cavities in arthroscopy it is not surprising to note that the basic mechanics and working principals of this pump are similar to a uterine distending pump Hamou Endomat (Karl Storz, Tuttinglheim, Germany). Thus it is seen that the basic mechanics and the working principals of the pumps used in arthroscopic surgery for distending joint cavities is similar to the pumps used in hysteroscopic surgery for distending the uterine cavity. Some other commercially available pump systems for use in arthroscopy are Arthro Pump 2202 of Richard Wolf, the Intelijet and Access 15 systems of Dyonics and the Apex Universal Irrigation System of Linvatec Corporation. Some other prior art devices used in arthroscopy are described in U.S. Pat. No. 4,650,462 (DeSatanick et al), U.S. Pat. No. 4,998,914 (Weist et al), U.S. Pat. No. 5,556,378 (Storz et al), U.S. Pat. No. 6,436,072 (Kullas et al), U.S. Pat. No. 5,460,490 (Carr et al) and U.S. Pat. No. 5,152,746 (Atkinson et al).

A Proposed Definition for an Ideal 'Continuous Flow Irrigation Distending System':

On the basic of the complications and the general principals associated with 'continuous flow irrigation' the Inventors propose here below define an ideal continuous flow irrigation distending system. The Inventors believe that in order to become ideal systems, a continuous flow irrigation distending system should comprise of 16 features which are as follows:

1. It should be possible to use the same distending system in all endoscopic surgeries which utilize 'continuous flow irrigation'.
2. A predictably constant clear visualization should always be available.
3. A predictably stable distension of the cavity walls should always be present.
4. The physiological contractions of the cavity wall should have negligible or minimal effect on the cavity pressure and cavity distension.
5. The mechanical movements of the irrigation tubes and the endoscope should have negligible or minimal effect on the cavity pressure and cavity distension.
6. The real time rate of intravasation of the irrigation fluid should be constantly known to the surgeon without using any type of fluid flow meters.
7. It should be possible to create and maintain any desired cavity pressure for any desired constant flow rate at which fluid may be allowed tb pass through the cavity.
8. An almost actual fluid pressure inside the cavity should always be known to the surgeon in a simple and reliable manner, while working at any flow rate, without the need of inserting a separate catheter into the cavity and by using a pressure sensor situated far away from the cavity in the upstream portion of the inflow tube.
9. Negligible or minimal fluid turbulence should be present in the fluid inside the cavity and in the fluid flowing through the rest of the irrigation circuit, thus implying that the fluid flow should be as close to a streamline flow as possible.
10. The pressure difference between any two points situated in the endoscopic irrigation circuit should be negligible or minimal even at high flow rates encountered in endoscopic surgery. Also at a fixed cavity flow rate the pressure difference between any two fixed points in the irrigation circuit should not vary during the entire endoscopic procedure.
11. It should be possible to maintain a relatively higher cavity pressure without increasing the 'maximum possible intravasation rate'.
12. It should be possible to increase or decrease the cavity refilling time in a predictably controlled manner.
13. It should be possible to predictably limit the magnitude of a pressure surge which might occur if the outflow tube is accidentally blocked especially while working at a high flow rate.
14. It should be possible to predict by a fair degree of accuracy the total volume of irrigation fluid which would be consumed in the entire endoscopic procedure so that required quantity of irrigation is fluid is taken at the beginning of surgery so that surgery is not interrupted later on account of changing the fluid bottles.
15. It should be possible to safely, easily and quickly switch between two different types of irrigation fluids, for example between normal saline and glycine, intraoperatively during an endoscopic procedure, in any desired short period of time such that the cavity pressure does not vary as a result of such maneuver.
16. It should be possible to set an upper safe limit for the maximum permissible cavity pressure and the maximum permissible inflow rate and it should be possible to set these two safety parameters independent of each other.

In the preceding paragraphs the physical principals, the components and surgical complications associated with 'continuous flow irrigation' have been explained in context with endoscopic procedures such as hysteroscopy, TURP and arthroscopy. Also multiple prior art systems have been categorized on the basis of component layout. In the subsequent paragraphs the physical principals, advantages and disadvantages of the prior art systems shall be described to establish the uniqueness, the mechanical novelty and the functional novelty of the present invention in comparison to the prior art systems.

A Variable Speed Peristaltic Pump on Inflow:

Hamou Endomat (Karl Storz, Tuttinglheim, Germany) is a popular distending system and is used by surgeons worldwide for distending the uterine cavity in hysteroscopic surgeries. In this system a peristaltic pump is incorporated on the inflow side of the uterine cavity while the out flow tube directly drains into a waste fluid collecting vessel at atmospheric pressure and a provision of attaching a vacuum source to the said waste fluid collecting vessel is also provided in this system. A pressure transducer located in the upstream portion of the inflow tube constantly senses the fluid pressure and constantly conveys feedback pressure signals to a controller which in turn regulates by a feed back mechanism the rotations of the peristaltic pump, thereby constantly increasing or decreasing the pump flow rate in order to maintain the cavity pressure around a desired value. Thus the cavity pressure is not constant and fluctuates around the initially preset value. The cavity pressure thus exhibits irregular fluctuations having a variable frequency and variable amplitude. Such pressure fluctuations do not permit a constantly clear visualization as it does not allow establishment of a stable mechanical distension of the cavity walls. Prior to starting the endoscopic procedure the surgeon selects desired values of the maximum permissible cavity pressure and the maximum permissible inflow rate for the planned endoscopic procedure and the said values are fed into a controller via suitable input means provided in the pump system console. In such system the 'desired cavity pressure' and 'the value of the maximum permissible cavity pressure' both are the same entities. Let a hypothetical situation be assumed wherein the surgeon selects 80 ml/min as the maximum inflow rate and 100 mm Hg as the desired that is maximum permissible cavity pressure. When the system is started the peristaltic pump operates at increasing RPM's to create 100 mm Hg pressure, however if even at the maximum set inflow rate of 80 ml/min also a cavity pressure lower than 100 mm Hg is developed then the peristaltic pump just continues to work at the said maximum flow rate of 80 m/min even though the cavity pressure continues to remain below the desired value of 100 mm Hg. In such situation the cavity pressure can be raised to desired preset value of 100 mm Hg only by increasing the value of the maximum permissible inflow rate or by reducing the magnitude of outflow suction. The outflow being essentially uncontrolled, reducing the out flow vacuum also may not yield the desired result, at least not in a predictable or controlled manner. The purpose of having including the just stated hypothetical situation is to demonstrate that in the Hamou Endomat, the cavity pressure is not independent of the flow rate, such that the cavity pressure can be increased or decreased by correspondingly increasing or decreasing the inflow rate. Also, in the Hamou Endomat if the maximum permissible inflow rate is increased it also increases the 'maximum possible intravasation rate', a concept which has already been explained. Also as explained above the physiological contractions of the cavity wall and the unavoidable movements of the irrigation tubes and the endoscope gives rise to minute pressure variations inside the cavity. Such pressure variations are constantly corrected by the said system which causes significant pressure fluctuations in the uterine ca ity. An uncontrolled outflow is one of the major reason due to which a predictably stable cavity pressure and a predictably stable cavity wall distension cannot be maintained by the Hamou Endomat distension system. Taking an extreme example, by using the Hamou Endomat, it is impossible to maintain a precise cavity pressure of 100 mm Hg for a precise cavity flow rate of 1 ml/min, while such extreme situation is very easily possible if the system of the present invention is used. The features available in the system of Hamou Endomat is compared with the ideal system as defined above by the Inventors to find its suitability in Table 4.

TABLE 4

Comparison of the System of Hamou Endomat with the Ideal System

| IDEAL SYSTEM | SYSTEM OF HAMOU ENDOMAT |
| --- | --- |
| It being possible to create and maintain any desired precise tissue cavity pressure for any desired precise constant outflow rate for any length of time. | Not possible. |
| The instantaneous real time rate of fluid intravasation into the patient's body being constantly known without using any type of fluid flow rate sensors. | Only the total volume of fluid absorbed over a certain period of time can be determined. The instantaneous real time rate of fluid intravasation is not obtainable. |
| It being possible to maintain the cavity pressure at any desired precise value for any length of time. | No, the cavity pressure continuously fluctuates around a preset value. |
| It being possible to maintain any desired high cavity pressure without increasing the 'maximum possible intravasation rate'. | Not possible. |
| It being possible to predictably maintain a constant clear visualization and a stable cavity distension for any length of time. | Not possible. |
| It being possible to easily and quickly change over from one type of irrigation fluid to a different type of irrigation fluid intra operatively during an endoscopic procedure in any desired short period of time such that the cavity pressure does not change during such maneuver. | Not possible. |

* Examples of some other prior art systems similar to 'Hamou Endomat' are Uteromat Fluid Control of Olympus company, Hystero Pump II 222 of Richard Wolf company, Arthropump plus (Karl Storz, Tuttinglheim, Germany) and a system described in U.S. Pat. No. 4998914 (Weist et al).

A Variable Speed Peristaltic Pump on Inflow & a Flow Regulating Valve on Outflow:

Systems manufactured by Apex Universal Irrigation System (Linvatec Corporation, USA) for use in arthroscopic surgery has been described in U.S. Pat. No. 5,460,490 (Carr et al). The physical principals of this system are similar to the Hamou Endomat (Karl Storz) described in the previous paragraph except for the fact that a pressure regulating pinch valve has been attached over the out tube. By reducing the lumen of the outflow tube by constricting the said pinch valve relatively higher joint cavity pressures can be achieved for the same inflow rates. By incorporating the said pinch valve an attempt has been made to make the cavity pressure relatively independent of the cavity flow rate. However at any one position of the pinch valve the cavity pressure can only be increased by increasing the rotations of the inflow peristaltic pump. The features available in the system of Apex Universal Irrigation System (Linvatec) is compared with the ideal system as defined above to find its suitability in Table 5.

TABLE 5

Comparison of the System of Apex Universal Irrigation System with the Ideal System

| IDEAL SYSTEM | APEX UNIVERSAL IRRIGATION SYSTEM (linvatet Corporation, USA) |
|---|---|
| It being possible to create and maintain any desired precise joint cavity pressure for any desired precise constant outflow rate, for any length of time. | Not possible. |
| It being possible to know the instantaneous real time rate of fluid extravasation without using any fluid flow rate sensors. | Not possible. |
| It being possible to maintain pressure at any desired precise value for any length of time. | No, the cavity pressure continuously fluctuates around a preset value. |
| It being possible to maintain any desired high joint cavity pressure without increasing the 'maximum possible extravasation rate', | This is possible only if an upper safe limit for the maximum inflow rate is preset and by adequately tightening the outflow pinch valve. |
| It being possible to predictably maintain a constant clear visualization and a stable cavity distension for any length of time. | Not possible. |
| It being possible to easily and quickly change over from one type of irrigation fluid to a different type of irrigation fluid intra operatively during an endoscopic procedure in any desired short period of time such that the cavity pressure does not change during such maneuver. | Not possible. |

A Fixed Speed Peristaltic Pump on Inflow and a Flow Regulating Valve on Outflow:

U.S. Pat. No. 4,650,462 (DeSatanick et al) describes a prior art system suggested to be used in arthroscopic surgery. In this system a fixed RPM peristaltic pump which operates at fixed preset flow rate is incorporated on the inflow side, a pressure transducer measures the pressure directly from the joint cavity and a variable flow controlling valve is attached over the out flow tube. The peristaltic pump constantly runs at a fixed flow rate while the variable flow controlling restriction valve by a pressure feedback mechanism maintains the cavity pressure around a desired preset value by constantly constricting and dilating the inner diameter of the outflow tube. The distal end of the outflow tube opens in a waste collecting container with a vacuum source attached to it. Due to irregular opening and closing of the restriction valve the cavity pressure is turbulent and exhibits wide amplitude around a preset pressure value. The frequency of the said pressure fluctuations is also irregular. The features available in the system described in U.S. Pat. No. 4,650,462 (DeSatanick et al) is being compared with the features that should be available in an ideal system to find out the suitability of the system of DeSatanick et al in table 6.

TABLE 6

Comparison of the System of DeSatanick et al with the Ideal System

| IDEAL SYSTEM | DeSatanick et al |
|---|---|
| It being possible to create and maintain any desired precise joint cavity pressure for any desired precise constant outflow rate, for any length of time. | Not possible. |
| It being possible to know the instantaneous real time rate of fluid extravasation without using any type of fluid flow rate sensors. | Not possible. |
| It being possible to maintain the pressure at any desired precise value for any length of time. | No, the cavity pressure continuously fluctuates around a preset value. |
| It being possible to maintain any desired high joint cavity pressure without increasing the 'maximum possible extravasation rate'. | May be possible by fixing an upper safe limit of the inflow rate and by suitably reducing the outflow tybe lumen by tightening the outflow regulating valve. |
| It being possible to predictably maintain a constant clear visualization and a stable cavity distension for any length of time. | Not possible. |
| It being possible to easily and quickly change over from one type of irrigation fluid to a different type of irrigation fluid intra operatively during endoscopic procedure in any desired short period of time such that the cavity pressure does not change during such maneuver. | Not possible. |

A Fixed Speed Peristaltic Pump on the Inflow and a Variable Speed Peristaltic Pump on the out Flow:

U.S. Pat. No. 5,556,378 (Storz et el) describes a prior art system suggested to be used in endoscopic surgeries such as hysteroscopy, TURP and arthroscopy. In this system two peristaltic pumps operate simultaneously, the inflow pump pushes fluid into the tissue cavity while the outflow pump extracts fluid from the cavity. One pressure transducer is located on the outlet end of the inflow pump while a second pressure transducer is located on the inlet end of the outflow pump. The pressure signals from both these pressure transducers are sent to a controller. The RPM of each pump are determined by suitable sensors like tachometers and the corresponding RPM signals are also sent to the controller. The peristaltic pump RPM are directly proportional to the pump flow rate thus the RPM related signals from both the pumps send flow rate related information to the controller. In this system the inflow peristaltic pump constantly operates at a fixed predetermined flow rate while the outflow peristaltic pump operates at variable flow rates under the influence of pressure feedbacks from the two pressure transducers and the flow rate of the inflow peristaltic pump which has already been predetermined. Before starting the surgery the surgeon chooses a desired flow rate for the inflow peristaltic pump and a desired pressure which would be maintained inside the cavity all through the endoscopic procedure. On the basis of the pressure signals from the two pressure transducers and set flow rate of the inflow pump the controller maintain the cavity pressure around the preset value by constantly increasing or decreasing the flow rate of the out flow peristaltic pump. The features available in the system described in U.S. Pat. No. 5,556,378 (Storz et al) is being compared with is being compared with the features that should be available in an ideal system to find out the suitability of the system of Storz et al in table 7.

The system of Storz is somewhat close to the ideal system. However, the Inventors have noticed that it is not at all possible to operate the system of Storz without utilizing the controller. The controller is an integral part of the system of Storz. Applicants have further noticed that as the outflow pump is a variable speed peristaltic pump which is continuously controlled by the controller, the cavity pressure continuously fluctuates around a preset value. This is because of the fact that the fluctuations in the cavity pressure due to the physiological cavity wall contractions and the mechanical movements of the irrigation circuit are for very short time period and are irregular. The Applicants have noticed that the pressure transducers attached on the inflow and the outflow sides to detect the cavity pressure. Once a variation in the cavity pressure is detected, a corresponding signal is sent to the controller, which after comparing the input signal with a reference signal, outputs a correction signal which is provided to the outflow pump, which thereafter corrects amount of liquid being withdrawn from the cavity. It may take about 2 to 4 seconds approximately for the entire process to happen and by the time the outflow pump starts correcting, the cavity would have returned back to its original shape. Thus, the Applicants note that in the system of Storz et al the controller constantly corrects the variations in the cavity pressure caused by the physiological cavity wall contractions and the mechanical movements of the irrigation circuit, thus extending the time period for which the cavity pressure varies. This leads to extended turbulence inside the cavity.

Note: There are many more mechanical and functional differences between the present invention and the system just described, that is U.S. Pat. No. 5,556,378 (Storz et al).

TABLE 7

Comparison of the System of Storz et al with the Ideal System

| IDEAL SYSTEM | U.S. Pat. No. 5,556,378 (Storz et al) |
| --- | --- |
| It being possible to measure the actual cavity pressure in a simple and easy manner using minimum number One pressure transducer in the upstream part of the inflow tube accurately measures the actual cavity pressure in a simple and easy manner. | Two pressure transducers determine the cavity pressure in a relatively less accurate manner because the cavity pressure constantly fluctuates. |
| It should be possible to operate the system even without a controller. | This system cannot be operated without the help of a controller. |
| It being possible to create and maintain any desired precise cavity pressure for any desired precise constant outflow rate, for any length of time. | Not possible. |
| It being possible to know the instantaneous real time rate of fluid intravasation without using any type of fluid flow rate sensors. | Only the total volume of fluid absorbed over a certain period of time can be determined. |
| It being possible to know the real time rate of fluid intravasation without using a controller. | Not possible. |
| It being possible to maintain the cavity pressure at any desired precise value for any length of time. | No, the cavity pressure continuously fluctuates around a preset value. |
| It being possible to maintain any desired high joint cavity pressure without increasing the 'maximum possible extravasation rate'. | This is possible by fixing the inflow rate at a safe level. |
| It being possible to predictably maintain a constant clear visualization and a stable cavity distension for any length of time. | Not possible. |
| It being possible to easily and quickly change over from one type of irrigation fluid to a different type of irrigation fluid intra operatively during an endoscopic procedure in any desired short period of time such that the cavity pressure does not change during such maneuver. | Not possible. |

Centrifugal Pump on the Inflow:

A system described in U.S. Pat. No. 6,436,072 (Kullas et al) is suggested to be used in endoscopic procedures such as hysteroscopy, TURP and arthroscopy. In this system a variable RPM centrifugal pump is incorporated as the inflow pump and a pressure transducer constantly senses the cavity pressure and sends corresponding pressure signals to a controller. Similarly a sensing devise such as a tachometer coupled with the rotor shaft said centrifugal pump constantly sends the pump RPM related information to the controller. By a pressure feedback mechanism the controller regulates the pump RPM in such a manner that the cavity pressure is maintained around a desired predetermined value. A centrifugal pump is a dynamic pump whose outflow rate is inherently inversely responsive to the pressure in the outflow circuit which in this case is the pressure inside the tissue cavity. The basic component lay out of the system is such that a sterile irrigation fluid contained inside a fluid source reservoir is transported to the inlet end of the centrifugal pump via a plastic tube which connects the fluid source reservoir with the inlet end of the said centrifugal pump. The fluid source reservoir is usually hung at a height about 1 to 2 feet above the pump in order to introduce fluid into the pump inlet by gravity. Before starting the endoscopic procedure the surgeon selects a desired cavity pressure to be maintained during the endoscopic procedure by feeding the value of the said desired pressure via suitable input means which are present in the pump console system. In system being discussed the outflow is uncontrolled because the outflow tube directly empties into a waste fluid collecting reservoir. If the transducer senses a fall in the cavity pressure the controller increases the efficiency of the centrifugal pump by increasing its RPM and in this manner the pump outflow rate is increased which ultimately culminates in an increased cavity pressure. Similarly if an increased cavity pressure is sensed the cavity pressure is accordingly reduced by reducing the RPM of the pump. The advantage of using a centrifugal pump is that even if the pump outflow is totally blocked the pump outflow pressure cannot exceed a certain value commonly termed as the pressure head. In physical terms the pressure head of a centrifugal pump is the pressure generated on the pump outflow side at a zero flow rate, a situation which can be attained by intentionally blocking the pump outflow tube. Alternatively if the discharge of the centrifugal pump is pointed straight up in a vertical pipe the fluid in a vertical tube shall rise to a certain maximum height and the pressure generated at the base of such a vertical column of fluid is known as the 'pressure head' of the centrifugal pump. The pump head is mainly determined by the pump RPM and the outside diameter of the pump impeller. The pump head is increased by increasing the efficiency of the pump and the efficiency of the pump can be increased by either increasing the pump RPM or by increasing the outside diameter of the pump impeller. The main problem associated with such centrifugal pump systems is that if the pressure head is increased by increasing the RPM then maximum possible pump flow rate, that is the pump flow rate at a zero pressure head, becomes dangerously high and this significantly increases the 'maximum possible rate of fluid intravasation'. Let a hypothetical situation be considered wherein at 1000 RPM a cavity pressure of 80 mm Hg is being maintained for a cavity flow rate of 100 ml/min which essentially means that in context with stated parameters the pump is actually pumping fluid into the cavity at a rate of 100 ml/min. If accidentally a large diameter vein inside the cavity wall is cut the cavity pressure may immediately drop to almost zero which implies that effective pressure head (that the pressure at the pump outflow) has also fallen to zero and at such a low pressure head this pump may push fluid into the tissue cavity at a very high rate which may be as high as 2 to 3 litres/min and if irrigation fluid intravasates into the patient's blood circulation at such high rates the patient may die within minutes. It may be argued that a maximum permissible upper limit of the pump RPM may be set but if the desired cavity pressure is not achieved at the said upper RPM limit then surgeon has to perform a compromised surgery at an undesired low cavity pressure or increase the cavity pressure by increasing the maximum permissible upper limit of the pump RPM but such action again increases the 'maximum possible intravasation rate'. Thus in such systems if the cavity pressure can be raised then the 'maximum possible intravasation rate' also increases. Taking an extreme hypothetical example while in the present invention it is possible to predictably and precisely maintain the cavity pressure at 300 mm Hg pressure with the 'maximum possible intravasation rate' being equal to 2 ml/min, such a situation in impossible to even conceive in the centrifugal system being described in this paragraph. Further, in case of the said centrifugal pump system the cavity pressure is never stable as it constantly fluctuates around a preset value in an irregular manner and the fluid turbulence inside the cavity is also very high. Features of the said centrifugal pump system described in the U.S. Pat. No. 6,436,072 is being compared with the features of the ideal system in table 8.

TABLE 8

Comparison of the System of Khullas et al with the Ideal System

| IDEAL SYSTEM | U.S. Pat. No. 6,436,072 (Kullas et al) |
| --- | --- |
| It being possible to create and maintain any desired precise cavity pressure for any desired precise constant outflow rate, for any length of time. | Not possible. |
| It being possible to know the instantaneous real time rate of fluid intravasation without using any type of fluid flow rate sensors. | Not possible. |
| It being possible to maintain the cavity pressure at any desired precise value for any length of time. | No, the cavity pressure continuously fluctuates around a preset value. |
| It being possible to maintain any desired high cavity pressure without increasing the 'maximum possible intravasation rate'. | Not possible. |
| It being possible to predictably maintain a constant clear visualization and a stable cavity distension for any length of time. | Not possible. |

TABLE 8-continued

Comparison of the System of Khullas et al with the Ideal System

| IDEAL SYSTEM | U.S. Pat. No. 6,436,072 (Kullas et al) |
|---|---|
| It being possible to easily and quickly change over from one type of irrigation fluid to a different type of irrigation fluid, intra operatively during an endoscopic procedure in any desired short period of time such that the cavity pressure does not change during such maneuver. | Not possible. |

Variable Speed Centrifugal Pump of the Inflow and a Gear Pump on the Outflow:

Such a system has been described in the U.S. Pat. No. 5,630,798 (Beiser et al) and has been suggested to be used in endoscopic procedures such as arthroscopy. This system is similar to the system described in the above paragraph except for the fact that in this system a 'fixed speed gear pump' has also been incorporated on the outflow side. The surgeon sets a desired cavity pressure and also sets a specific flow rate for the gear pump. By a pressure feedback mechanism the controller maintains the cavity pressure around a desired value by constantly varying the RPM of the inflow centrifugal pump. However a precise stable cavity pressure is not achieved and the cavity pressure constantly fluctuates around a preset pressure value and the said pressure fluctuations are of an irregular frequency and irregular amplitude. However one advantage of this system in comparison to the system described in the previous paragraph is that in this system there is a relatively slightly better mechanical stabilization of the cavity walls and pressure fluctuations are also relatively less. However significant cavity pressure fluctuations and fluid turbulence do exist. In this system if the cavity pressure is increased by decreasing the RPM of the outflow gear pump the 'maximum possible rate of fluid intravasation' does not increase because the in this system the 'maximum possible rate of fluid intravasation' is equal to the maximum outflow rate of the inflow centrifugal pump at zero pressure head which increases only if the RPM of the centrifugal pump are increased In the presently being discussed system for a specific value of the centrifugal pump RPM the specific value of maximum cavity pressure can be generated by reducing the RPM of the outflow gear pump to zero value, however if a still higher cavity pressure is required then that can be possible only by increasing the RPM of the inflow centrifugal pump which would dangerously increase the 'maximum possible rate of fluid intravasation or extravasation'. It has already been stated previously that the term 'intravasation' is deemed to include the process of 'extravasation' as well but in this paragraph the term 'extravasation' has been intentionally used because the prior art being discussed has specifically recommended to be used in arthroscopic procedures besides other endoscopic procedures, and in arthroscopic procedures 'extravasation' predominates over 'intravasation' though both terms are essentially same. It is also to be noted that in the U.S. Pat. No. 5,630,798 (Beiser et al) being discussed a gear pump has been used as a positive displacement pump however no gear pump can be 100% sealed and some forward or backward leakage might occur while the pump is operating or is stationary and the direction of such leakage shall depend on the pressure gradients on both sides of the gear pump. In this respect a gear pump is different from a peristaltic pump, which is also a positive displacement pump, because in a peristaltic pump no fluid flow in any direction when the pump is stationary. The said leakage through a gear pump tends to make the outflow relatively uncontrolled, depending upon the magnitude of such leakage which imparts turbulence to the fluid flow. Features of the said centrifugal pump system described in the U.S. Pat. No. 5,630,798 (Beiser et al) is being compared with the features of the Ideal system to find out its suitability in table 9:

TABLE 9

Comparison of the System of Beiser et al with the Ideal System

| INDEAL SYSTEM | Pat. No. 5,630,798 (Beiser et al) |
|---|---|
| It being possible to create and maintain any desired precise cavity pressure for any desired precise constant outflow rate, for any length of time. | Not possible. |
| It being possible to know the real time rate of fluid intravasation. | Such feature is not present is this prior art. |
| It being possible to know the instantaneous real time rate of fluid intravasation even without using a controller. | Not possible. |
| It being possible to maintain the cavity pressure at any desired precise value for any length of time. | No, the cavity pressure continuously fluctuates around a preset value. |
| It being possible to maintain any desired high cavity pressure without increasing the 'maximum possible intravasation rate'. | Not possible. |
| It being possible to predictably maintain a constant clear visualization and a stable cavity distension for any length of time. | Not possible. |
| It being possible to easily and quickly change over from one type of irrigation fluid to a different type of irrigation fluid intra operatively during an endoscopic procedure in any desired short period of time such that the cavity pressure does not change during such maneuver. | Such feature is not present is this prior art. |

The Dolphin II Fluid Management System (ACMI Circon, USA):

This type of system has been described in U.S. Pat. No. 5,814,009 (Wheatman). In this system the irrigation fluid is pushed into the uterine cavity by the help of a bladder pump which compresses the irrigation fluid contained in a collapsible plastic container. In this system a pressure transducer located in the downstream portion of the inflow tube near the inflow port constantly senses the cavity pressure and sends appropriate signals to a controller which by a feedback mechanism regulates the air pressure inside the bladder enclosing the said collapsible fluid source container. If the said pressure transducer senses a fall in the uterine cavity pressure it sends a feedback signal to the said controller via a feedback mechanism and the controller in turn increases the air pressure inside the said bladder by activating an air compressor which results in the collapsible fluid source container being compressed with a greater force which culminates in an increased inflow rate and the end result being an increased uterine cavity pressure. Similarly when the uterine cavity pressure increases the controller causes the bladder pressure to decrease and the end result being a reduced uterine cavity pressure. In this system the cavity pressure is maintained by irregularly fluctuating around a preset value, thus implying that in the said system the pressure cannot be maintained at a fixed and precise value. Features of the Dolphin II Fluid Management System (ACMI CIRCON) is being compared with the features of the ideal system to determine its suitability in table 10.

TABLE 10

Comparison of the System of Wheatman et al with the Ideal System

| IDEAL SYSTEM | U.S. Pat. No. 5,814,009 (Wheatman) |
| --- | --- |
| It being possible to create and maintain any desired precise cavity pressure for any desired precise constant outflow rate, for any length of time. | Not possible. |
| It being possible to know the instantaneous real time rate of fluid intravasation without using any flow rate sensor. | Not possible. |
| It being possible to maintain the cavity pressure at any desired precise value for any length of time. | No, the cavity pressure continuously fluctuates around a preset value. |
| It being possible to maintain any desired high cavity pressure without increasing the 'maximum possible intravasation rate'. | Not possible. |
| It being possible to predictably maintain a constant clear visualization and a stable cavity distension for any length of time. | Not possible. |
| It being possible to easily and quickly change over from one type of irrigation fluid to a different type of irrigation fluid, intra operatively during an endoscopic procedure in any desired short period of time such that the cavity pressure does not change during such maneuver. | Not possible. |

Thus it can be noticed that none of the system available till today or those which have been patented do not provide all the features required to qualify to be called as an ideal system.

OBJECTS OF THE INVENTION

The main object of the invention is to provide a safe and efficient system for distending body tissue cavities for those endoscopic procedures which utilize continuous flow irrigation. In technical terms the user should be able to create and maintain any desired pressure inside a tissue cavity through which fluid may be allowed to flow at any desired constant flow rate.

Another object of the present invention is to provide a system for distending tissue cavities using which it being possible to create and maintain any desired precise cavity pressure for any desired precise and fixed outflow rate, for any length of time.

Still another object of the present invention is to provide a system for distending tissue cavities using which it being possible to achieve a predictably constant clear endoscopic vision throughout the endoscopic procedure.

Yet another object of the present invention is to provide a system for distending tissue cavities using which it being possible to achieve a predictably stable mechanical cavity distension throughout the endoscopic procedure.

One more object of the present invention is to provide a system for distending tissue cavities using which it being possible to predictably maintain the cavity pressure at any desired precise value despite physiological contractions of the cavity wall.

One another object of the present invention is to provide a system for distending tissue cavities using which it being possible to constantly, accurately and reliably determine the instantaneous real time rate of fluid intravasation into the patient's body without using any type of fluid flow rate sensors.

A further object of the present invention is to provide a system for distending tissue cavities using which it being possible to determine the instantaneous real time rate of fluid intravasation mechanically without using a controller or any type of fluid flow rate sensors.

A further more object of the present invention is to provide a system for distending tissue cavities using which it being possible to maintain any desired precise and high cavity pressure without increasing the 'maximum possible fluid intravasation rate'.

Another object of the present invention is to provide a system for distending tissue cavities using which it being possible to measure the actual cavity pressure, in an accurate, reliable and simple manner, by using a pressure transducer located far away from the cavity in the up stream portion of the inflow tube.

Yet another object of the present invention is to provide a system for distending tissue cavities using which it being possible to make the pressure inside the body cavity and the flow rate of the fluid passing through the body cavity absolutely independent of each other such that the value of any may be altered without affecting the value of the other.

Still another object of the present invention is to provide a system for distending tissue cavities using which it being possible to reduce the cavity filling time in a predictably controlled manner and at the same time achieving a desired cavity pressure at the end of the cavity refilling phase, cavity refilling time being the time taken to completely fill a cavity with the irrigation fluid.

One more object of the present invention is to provide a system for distending tissue cavities using which it being possible for the surgeon to have a fairly accurate assessment of the total volume of the irrigation fluid which would be required to complete the entire endoscopic procedure.

On another object of the present invention is to provide a system for distending tissue cavities using which it being possible for the surgeon to accurately know the maximum pressure which might develop inside the cavity in case of an accidental obstruction of the outflow tube and it should be possible to minimize such rise in the cavity pressure in a controlled and predictable manner.

A further object of the present invention is to provide a system for distending tissue cavities using which it being possible to easily, quickly and safely change from one type of irrigation fluid to a different type of irrigation fluid, for example between normal saline and glycine, intraoperatively (that is during a surgical procedure), in any desired short period of time such that the cavity pressure does not change during such maneuver.

SUMMARY OF THE INVENTION

The present invention is a safe and an efficient system for distending body tissue cavities for those endoscopic procedures which utilize continuous flow irrigation. The present invention is a system of creating and maintaining any desired positive pressure inside a body tissue cavity through which fluid is made to flow at any fixed flow rate, including a zero flow rate. Alternatively the present invention may be considered as a system of creating cavity fluid pressure which is absolutely independent of the cavity outflow rate. The present invention comprises of two peristaltic pumps which work simultaneously, for indefinite time, at absolutely fixed flow rates to create and maintain any precise desired cavity pressure for any desired cavity outflow rate, including a zero outflow rate. One pump is located on the inflow side of a cavity while the other pump is attached to the out flow side of the cavity. Further if any fluid is being absorbed into or through the cavity walls, such as fluid intravasation which occurs during hysteroscopic endometrial resection, the instantaneous real time rate of such fluid absorption can be constantly determined in the proposed invention without using any type of fluid flow rate sensors. Also the cavity pressure can be maintained at any desired high value without increasing the 'maximum possible fluid intravasation rate'. The proposed invention also has multiple other features of endoscopic surgical relevance which greatly enhance the patient safety and efficiency during endoscopic surgery few such features being shortening of the cavity refilling time in a predictably controlled fashion, to be able to predict by a fair degree of accuracy the volume of fluid which would be required to complete the endoscopic procedure, to be able to quickly switch during endoscopic surgery between two types of irrigation fluids without varying the cavity pressure and to be able to predict and limit the magnitude of the maximum increase in the cavity pressure or the magnitude of a minor pressure surge which might occur in case of an accidental obstruction of the outflow tube for a specific outflow rate. Also the same system can be used for all types of endoscopic procedures which utilize continuous flow irrigation.

DETAILED DESCRIPTION OF INVENTION

Figure 1:
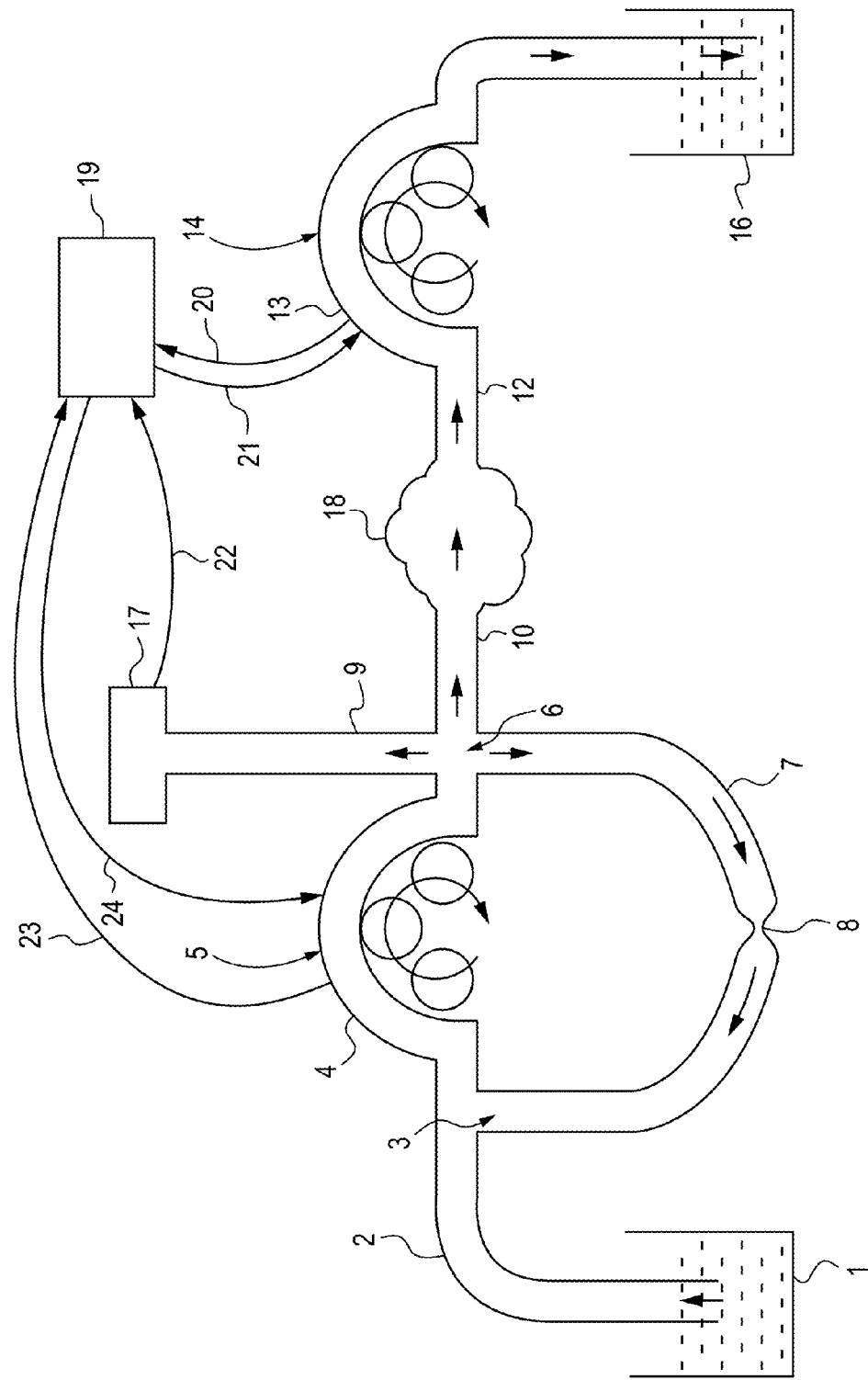
FIG. 1 shows the basic block diagram of the invention with the controller system.

Accordingly, the present invention provides a system for distending body tissue cavities of subjects by continuous flow irrigation during endoscopic procedures the said system comprising:

a fluid source reservoir containing a non viscous physiologic fluid meant for cavity distension;

a fluid supply conduit tube connecting the fluid source reservoir to an inlet port of a variable speed positive displacement inflow pump and an outlet port of the said inflow pump being connectable to an inflow port of an endoscope instrument through an inflow tube for pumping the fluid at a controlled flow rate into the cavity, the flow rate of the said inflow pump being termed as the inflow rate;

an inflow pressure transducer being located anywhere in the inflow tube between the outlet port of the inflow pump and the inflow port of the endoscope;

an outflow port of the endoscope being connectable to an inlet port of a variable speed positive displacement outflow pump through a outflow tube for removing the fluid from the cavity at a controlled flow rate, the flow rate of the said outflow pump being termed as the outflow rate, an outlet port of the outflow pump being connected to a waste fluid collecting container, and characterized in that a housing tube having a controllable constriction site is being provided between the fluid source reservoir and the inflow tube such that the same by-passes the inflow pump; wherein housing tube provides a route for any excess fluid being pumped by the inflow pump to bypass the inflow pump and go back to the fluid supply tube or the fluid source reservoir, thereby minimizing turbulence inside the cavity and maintaining the cavity pressure at a stable value despite physiological contractions of the cavity wall.

In an embodiment of the present invention, the fluid source reservoir containing the non-viscous physiologic fluid is maintained at atmospheric pressure or at a pressure greater than the atmospheric pressure.

In another embodiment of the present invention, a proximal open end of the fluid supply tube is connected to the fluid source reservoir and a distal end of the tube is connected to the inlet port of the variable speed positive displacement inflow pump.

In yet another embodiment of the present invention, the proximal open end of the fluid supply tube is constantly and completely immersed in the fluid source reservoir.

In still another embodiment of the present invention, a proximal end of the inflow tube is connected to the outlet port of the variable speed positive displacement inflow pump and a distal end of the inflow tube being connectable to the inflow port of the endoscope instrument.

In a further embodiment of the present invention, the variable speed positive displacement inflow pump is selected from the group comprising peristaltic pump, piston pump, gear pump, diaphragm pump and plunger pump.

In one more embodiment of the present invention, the variable speed positive displacement inflow pump is a peristaltic pump.

In one another embodiment of the present invention, the housing tube is releasably provided between the fluid source reservoir and the inflow tube to enable replacement of the housing tube with yet another housing tube having a different diameter at the constriction site to suit the operational need of the endoscopic procedure.

In a further more embodiment of the present invention, a proximal end of the housing tube is connected to the fluid supply tube near its distal end close to the inlet port of the inflow pump.

In an embodiment of the present invention, a proximal end of the housing tube is empties directly into the fluid source reservoir and is constantly and completely immersed in the fluid source reservoir.

In another embodiment of the present invention, a distal end of the housing tube is connected to the inflow tube near its proximal end close to the outlet port of the inflow pump.

In yet another embodiment of the present invention, the housing tube is provided with a clamping means at the constriction site to enable the user to vary the diameter of the housing tube at the constriction site to suit the operational needs of endoscopic procedures.

In still another embodiment of the present invention, the diameter of the housing tube at the constriction site is in the range of 0.005 mm to a maximum value which is less than the overall diameter of the rest of the housing tube In one more embodiment of the present invention, the diameter of the housing tube at the constriction site is in the range of 0.05 to 2.5 mm.

In one another embodiment of the present invention, the inflow pressure transducer is located sufficiently away from the cavity site, preferably near the outlet port of the inflow pump from the practical point of view, such that the actual pressure inside the cavity is measured.

In a further embodiment of the present invention, a proximal end of the outflow tube being connectable to the outlet port of the endoscope instrument and a distal end of the outflow tube is connected to an inlet port of the variable speed positive displacement outflow pump.

In an embodiment, the present invention further comprises an outflow pressure transducer connected between the proximal end of the outflow tube and the inlet port of the variable speed positive displacement outflow pump for measuring the pressure in the outflow tube.

In another embodiment of the present invention, the variable speed positive displacement outflow pump is selected from the group comprising peristaltic pump, piston pump, gear pump, diaphragm pump and plunger pump.

In yet another embodiment of the present invention, the variable speed positive displacement outflow pump is a peristaltic pump.

In still another embodiment of the present invention, the outlet port of the variable speed positive displacement outflow pump is connected to the waste fluid collecting container through a waste fluid carrying tube.

In one more embodiment, the present invention further comprises a micro-controller means electrically coupled to the inflow pressure transducer, the outflow pressure transducer, the inflow pump and the outflow pump for regulating the operation of the inflow and the outflow pumps.

In one another embodiment, the present invention further comprises a housing tube having a variable size constriction site being provided between the outflow tube and the waste fluid reservoir.

In another embodiment of the present invention, the fluid supply tube, the inflow tube, the outflow tube and the waste fluid carrying tube are flexible, disposable and are made of polymeric material.

The present invention also provides a method of distending a body tissue cavity of a subject by continuous flow initiation such that minimal or negligible fluid turbulence is present inside the cavity, such that any desired cavity pressure can be created and maintained for any desired outflow rate, said method comprising the steps of:

(a) dispensing a non viscous physiologic fluid meant for cavity distension from a fluid source reservoir to an inflow port of an endoscope instrument at a controlled flow rate through a fluid supply conduit tube, a variable speed positive displacement inflow pump and an inflow tube, the flow rate of the said inflow pump being termed as the inflow rate;

(b) injecting the non-viscous physiologic fluid at a controlled flow rate into the cavity for distending the body tissue cavity of the subject;

(c) removing a waste fluid from the cavity via the outlet port of the endoscope;

(d) actively extracting the waste fluid via the outlet port of the endoscope and transporting it to a waste fluid collecting reservoir at a controlled flow rate, the said flow rate being termed as the outflow rate through a outflow conduit tube, a variable speed positive displacement outflow pump and a waste fluid carrying tube and (e) providing a housing tube having a controllable constriction site between the fluid source reservoir and the inflow tube such that the housing tube provides a route for any excess fluid being pumped by the inflow pump or due the physiologic contraction of the cavity walls to bypass the inflow pump and go back to the fluid supply tube or the fluid source reservoir, and also to supply any extra fluid required as a result of physiologic expansion of the cavity wall, thereby avoiding turbulence inside the cavity and to maintain a stable pressure inside the cavity.

The present invention further provides a method of determining the instantaneous real time rate of fluid intravasation/extravasation during endoscopic procedures, without using any type of fluid flow rate sensor, said method comprising the steps of:

(a) dispensing a non viscous physiologic fluid meant for cavity distension from a fluid source reservoir to an inflow port of an endoscope instrument at a controlled flow rate through a fluid supply conduit tube, a variable speed positive displacement inflow pump and an inflow tube, the flow rate of the said inflow pump being termed as the inflow rate "R1";

(b) injecting the non-viscous physiologic fluid at the controlled flow rate into the cavity for distending the body tissue cavity of the subject;
(c) removing a waste fluid from the cavity via the outlet port of the endoscope;
(d) actively extracting the waste fluid via the outlet port of the endoscope and transporting it to a waste fluid collecting reservoir at a controlled flow rate, through a outflow conduit tube, a variable speed positive displacement outflow pump and a waste fluid carrying tube wherein the flow rate of the said outflow pump being termed as the outflow rate "R2",
(e) measuring instantaneously the pressure inside the cavity using a pressure transducer and denoting the determined pressure as "P", and obtaining the instantaneous real time rate of intravasation as:

$$KP=(R1-(R2+R3))^2$$

wherein K is a constant and R3 is the instantaneous real time rate of fluid intravasation or extravasation.

The proposed invention is described hereafter with reference to the accompanying drawings in order to clearly explain and illustrate the system and the working of the system. It is respectfully submitted the scope of the invention should not be limited by the description being provided hereafter.

Figure 2:
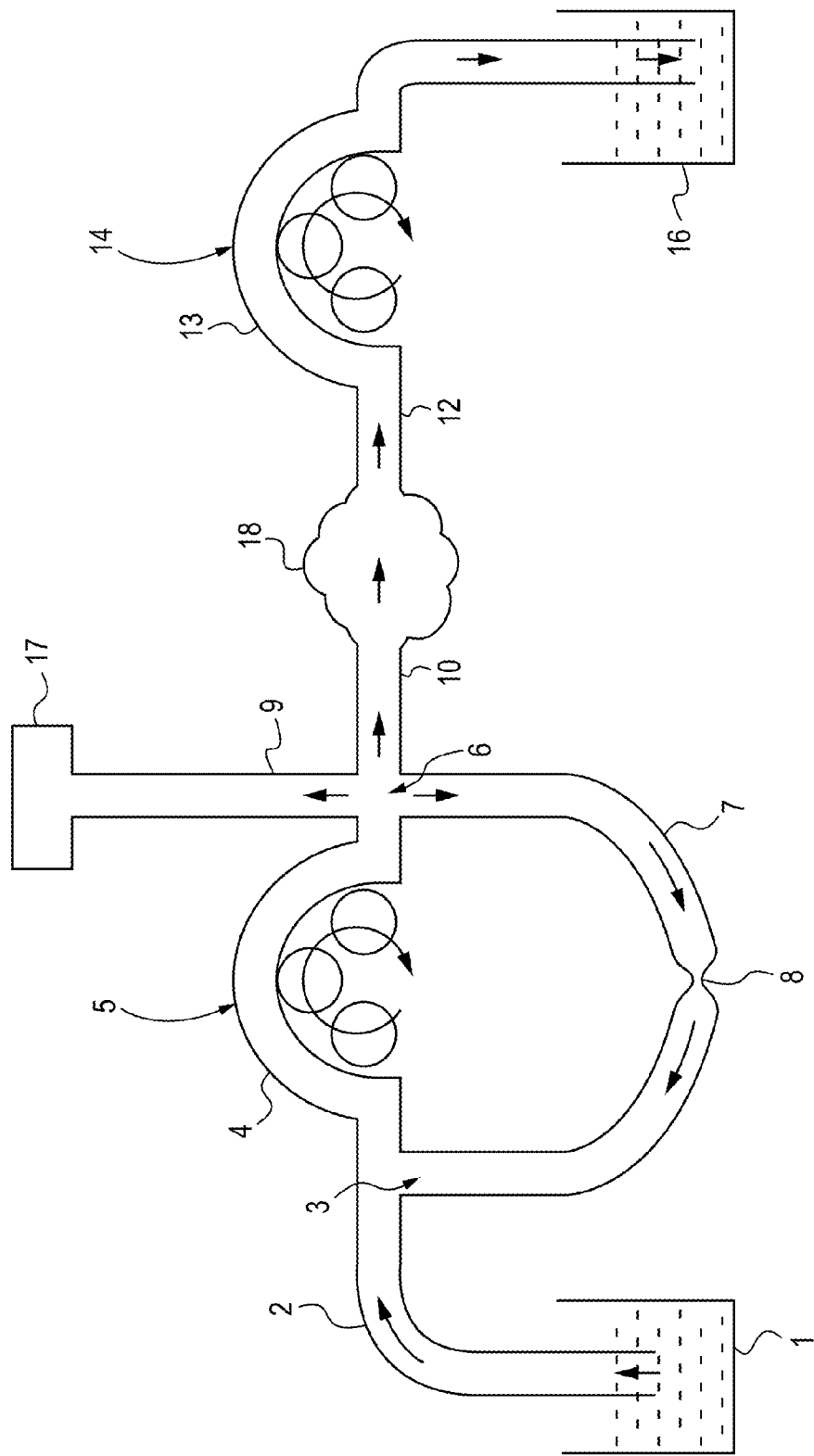
FIG. 2 shows the block diagram of the invention without the controller system.

The system of the present invention is a unique system for distending body tissue cavities in endoscopic procedures. In the proposed invention a body tissue cavity is distended by continuous flow irrigation in such a manner that the cavity pressure is absolutely independent of the cavity outflow rate, such the both, the cavity pressure and the outflow rate, may be independently altered without varying the value of the other parameter. The schematic diagram of the invention is shown in FIG. 1. The two peristaltic pumps 5 and 14 operate simultaneously in order to distend a tissue cavity in such a manner that the cavity pressure is totally independent of the cavity outflow rate. FIG. 1 represents the complete schematic diagram of the invention. Please note that the controller being used in the system shown in FIG. 1 is an optional feature and the system would provide most of the features even without the controller. The FIG. 2 represents the schematic diagram of the invention but without a controller system. Thus FIG. 2 is a mechanical version of the invention. A human operator is required to operate such mechanical version of the invention shown in FIG. 2. Though it is recommended that the controller based version of the invention be used in endoscopic surgeries, it is not essential. The controller being used in the present invention merely assists the user in arriving easily at some of the additional functions which otherwise can be performed manually. Thus, in this manuscript the mechanical version of the invention shown in FIG. 2 is being discussed in more detail in order to explain the basic physical principals of the invention with a greater clarity.

Referring to FIG. 2, the system shown in this figure comprises of two peristaltic pumps which can maintain a predictably precise stable cavity pressure for indefinite time by working simultaneously at constant rotational speeds. Pump 5 pushes fluid into the cavity 18 and while pump 14 simultaneously extracts fluid out of the cavity 18. The inlet end of the inflow peristaltic pump 5 is connected to a fluid source reservoir 1 via tube 2. The distal open end of tube 2 is constantly submerged in a sterile non viscous physiological fluid like 0.9% normal saline, 1.5% glycine, ringer lactate or 5% dextrose contained inside the reservoir 1 at atmospheric pressure. One end of the tube 7 connects the 'T junction' 3 situated at the inlet end of the pump 5 while the other end of tube 7 connects with the 'square junction' 6 situated at the outlet end of the pump 5. The 'T' junction 3 is thus the meeting point of three tubes, namely 2, 4 and 7. Similarly the square junction 6 is the meeting point of four tubes, 4, 9, 7 and 10. The rollers of the peristaltic pump 5 continuously compress and roll over the entire length of tube 4 thus displacing fluid in the direction of the curved arrow. This curved arrow denotes the direction in which the rotors of the peristaltic pump 5 rotate. Tube 7 has a constriction point 8 which can be located anywhere along its length. Such constriction point refers to a point where the inner diameter of the lumen of tube 7 is reduced in comparison to the lumen of the rest of the tube 7. Such constriction may be a permanent constriction in the lumen of tube 7 or it may be a variable constriction whose diameter may be increased or decreased as desired. A pressure transducer 17 is attached at one of tube 9 while the other end of tube 9 is connected anywhere on inflow tube 10. For practical convenience it is desirable that the said other end of tube 9 be connected in the up stream part of the inflow tube 10 such as at the square junction 6. The pressure transducer 17 measures the fluid pressure via a column of liquid or air present in the lumen of tube 9. The fluid pressure as measured by the pressure transducer shall be referred to as P. In this manuscript the term 'P' shall frequently be used to refer to the actual pressure inside the tissue cavity but in physical terms P is the pressure sensed by the transducer 17 at point 6. The pressure transducer 17 may also be in the form of a membrane diaphragm incorporated in the wall of the inflow tube 10 such that this membrane diaphragm is in direct contact with the fluid contained in the inflow tube 10, such that the linear movement excursions of the said membrane are interpreted as pressure of the fluid inside the inflow tube 10 by a suitable pressure transducer. Such type of pressure sensor being directly incorporated in the wall of the inflow tube 10 senses the fluid pressure without the intervention of tube 9. The basic purpose of the transducer is to measure the fluid pressure inside the inflow tube 10, such as at point 6, thus the mechanical construction of the transducer is not important as long as it measures the fluid pressure. For the sake of simplicity the existence of tube 9 shall be continued to be considered in the rest of the manuscript. The peristaltic pump 14 attached to the outflow side actively extracts fluid out of the tissue cavity 18 via the out flow tube 12. The outlet end of the pump 14 is connected to a waste fluid carrying tube 15 which opens into a waste fluid collecting reservoir 16 at atmospheric pressure. The rollers of the pump 14 constantly compress and roll over the entire length of the peristaltic pump tubing 13 thus displacing fluid in the direction of the curved arrow which also corresponds with the direction of pump rotation.

Figure 6:
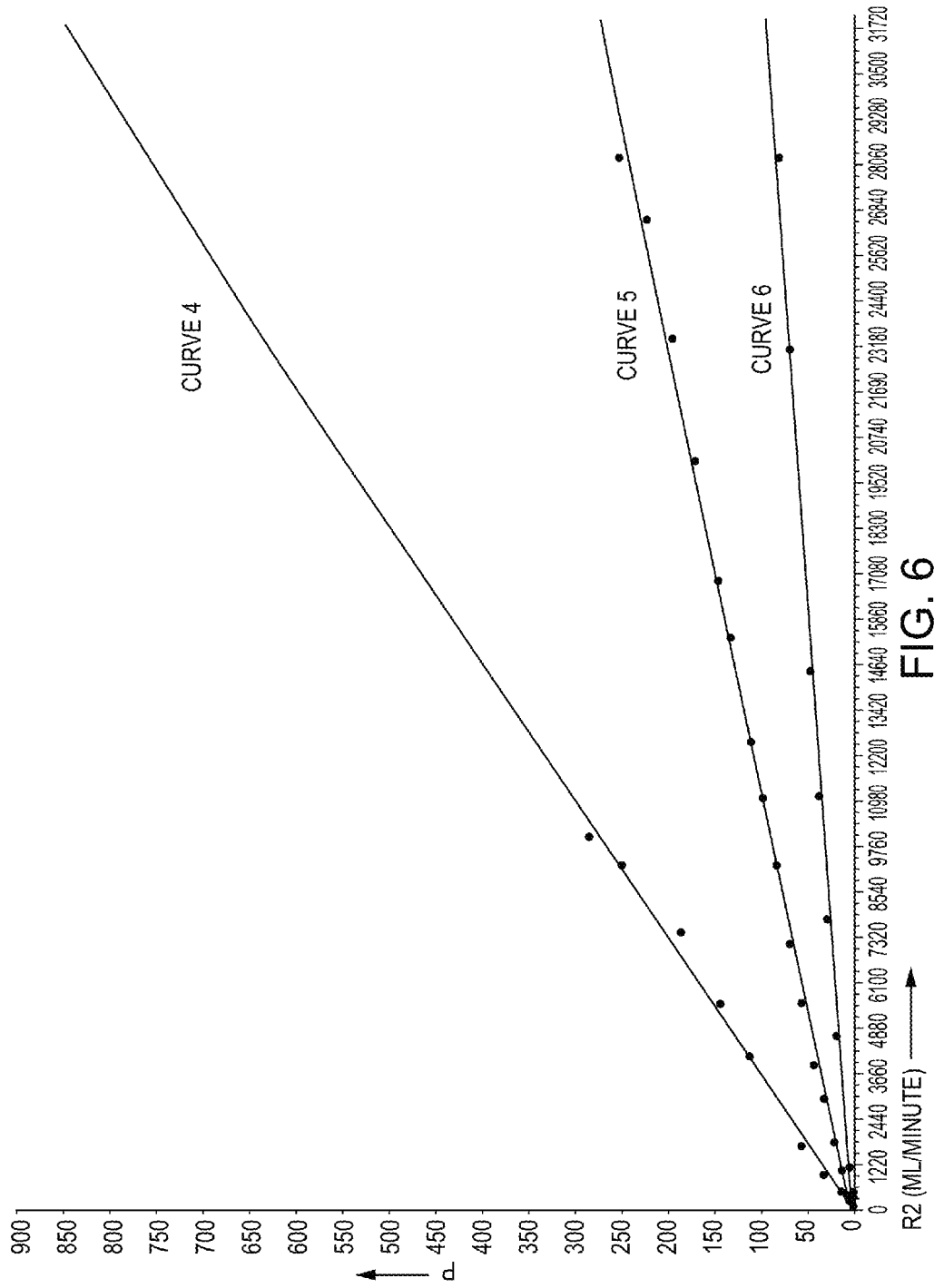
FIG. 6 shows curves 4, 5 and 6.

In order to understand the invention in a simpler manner both pumps are being considered to be identical in all respects and all the tubes shown in FIG. 6 and the inflow and out flow port are also being considered to be having the same uniform inner diameter. However the inner diameter of the tubes and the inflow and outflow ports can also be different. The inflow and outflow ports are metallic adaptors located at the proximal end of the endoscope and are meant to connect with the inflow and outflow tubes respectively, however the said inflow and outflow ports have not been separately shown in any of the figures. Tubes 4 and 13 consist of a soft resilient plastic material which can be efficiently compressed by the rollers of the peristaltic pumps. The other tubes also consist of a suitable resilient plastic material. It is assumed that all the components shown in FIG. 2, including the two pumps, all tubes and the said cavity, are placed at the same horizontal height with respect to the ground. Also the rollers of pumps 5 and 14 should press adequately over tubes 4 and 13 in such a manner that there is no leak through these tubes when the pumps are stationary. It is also assumed that there is no abnormal leak of fluid in the irrigation system, for example leak via a accidental hole made in any irrigation tube or a fluid leak which might occur if the endoscope loosely enters into the tissue cavity, for example in hysteroscopic surgery fluid leaks by the sides of the endoscope if the cervix is over dilated.

Figure 9:
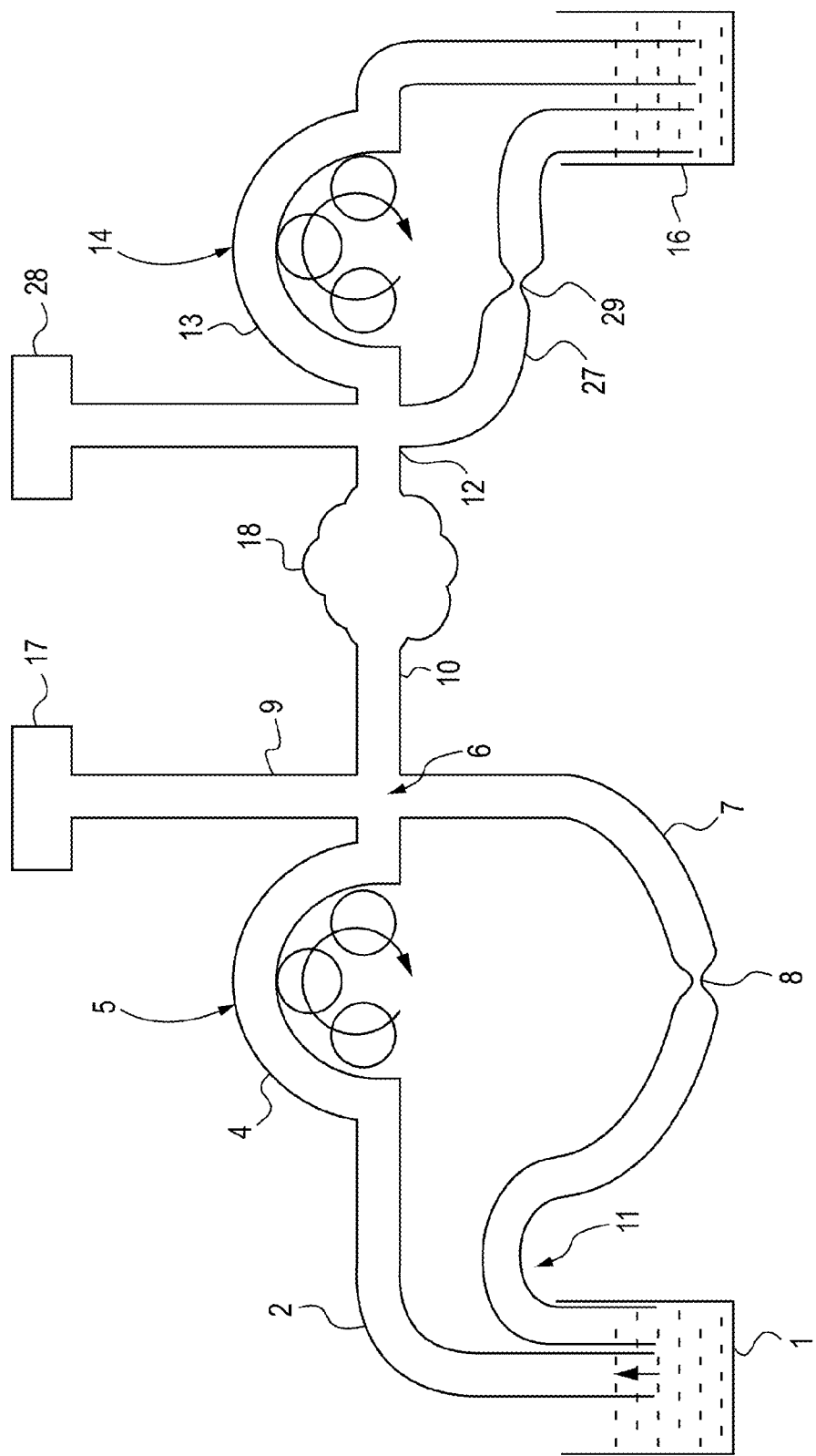
FIG. 9 is similar to FIG. 2 except that an additional/optional constriction housing tube 17 and an additional/optional pressure transducer 18 has been included.
Figure 10A:
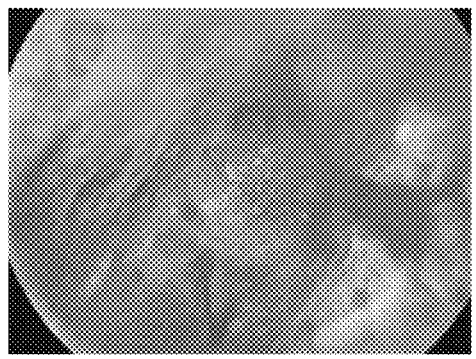
FIG. 10 shows the high resolution, sharp & high magnification images obtained using the system of the present invention.
Figure 10D:
Figure 10B:
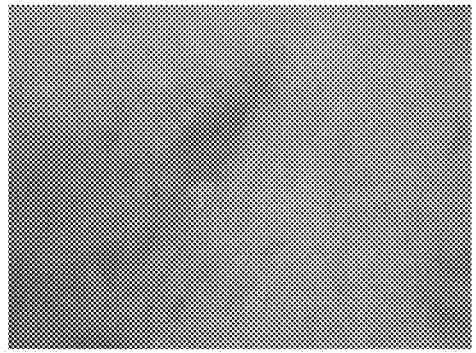
Figure 10E:
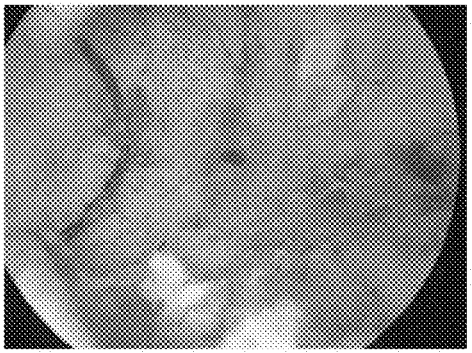
Figure 10C:
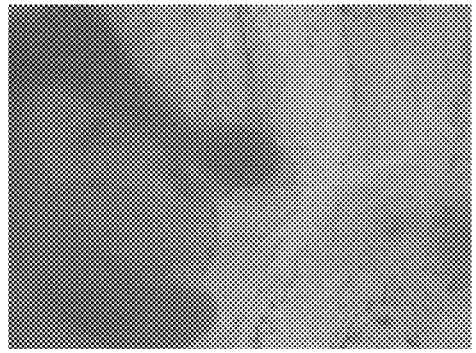
Figure 10F:

One end of the constriction site housing tube 7 instead of being connected with tube 2 at the 'T' junction 3 can also open directly into the fluid source reservoir 1. This shall not affect the efficiency of the system in any way but it may be practically difficult from the surgical point of view in some special cases. Thus such a provision is separately shown in FIG. 9 and the said tube has been labeled as 11 but it has intentionally not been included in the main block diagram of the invention as in FIGS. 1 and 2 in order to keep the drawings simple. Also a constriction site housing tube similar to tube 7 labeled as can be attached to the outflow tube 12 as shown in FIG. 9. In the said tube 27 the said constriction site is labeled as 29. Such tube can serve a number of purposes. Tube 27 can be utilized for relatively faster evacuation of air bubbles from the cavity. The said bubbles are invariably created inside the cavity as a result of electrosurgical cutting and coagulation or they may enter the cavity while the endoscope is being introduced into the cavity. Such bubbles cause extreme nuisance for the surgeon because they obscure vision and thus the surgical time may be greatly increased. In routine surgery the surgeon moves the tip of the resectoscope near the bubble and the bubble is sucked out of the cavity by the process of continuous flow irrigation. However in certain situations it may not be possible to bring the tip of the resectoscope near the bubble, one such situation is when bubbles accumulate inside a very deep cornuae associated with a long septum, the diameter of the cornuae being less than the outer diameter of the resectoscope. In such a situation the tubal opening situated at the center of the cornuae can only be visualized after evacuating such bubbles from the cavity. In such situation the bubbles can be quickly evacuated without moving the tip of the resectoscope near the bubbles by simply opening the constriction 29 in the tube 27. However such maneuver tends to completely collapse the cavity. Thus if the resctoscope tip is only moderately away from the bubbles the constriction is opened only partially so that the bubbles are sucked out and the cavity collapses by a relatively smaller magnitude. In place of the adjustable constriction site 29 a pressure release safety valve may be incorporated as a safety feature, however it is more beneficial to install such pressure safety valve in the inflow circuit. The tube 27 may also be used for quickly flushing air bubbles from the irrigation tubes by fully opening the constriction site 29 for a few minutes or seconds. The tube 27 may also be used for any other purpose as deemed fit by the surgeon. However the said tube 27 has intentionally not been included in the main block diagrams of the invention because by including the tube 27 in the main block diagrams it would have become very difficult to explain the basic physical principals of the invention. However tube 27 is a very beneficial component and is thus recommended to be incorporated in the system of the proposed invention. The opening and closing of the constriction site 29 can also be regulated manually to help in various special advanced endoscopic applications. Incorporation of tube with 27 the variable constriction site 29 can help in reducing the substantially high amplitude pressure variations inside the cavity caused by abnormally large cavity wall contractions, but such phenomenon is only rarely encountered. Also an additional pressure transducer 28 may also be attached on the out flow tube 12, if desired, as shown in FIG. 9. However the said pressure transducer 28 has intentionally not been included in the main block diagrams of the invention because by doing so it would have become very difficult to explain the basic physical principals of the invention.

Figure 3:
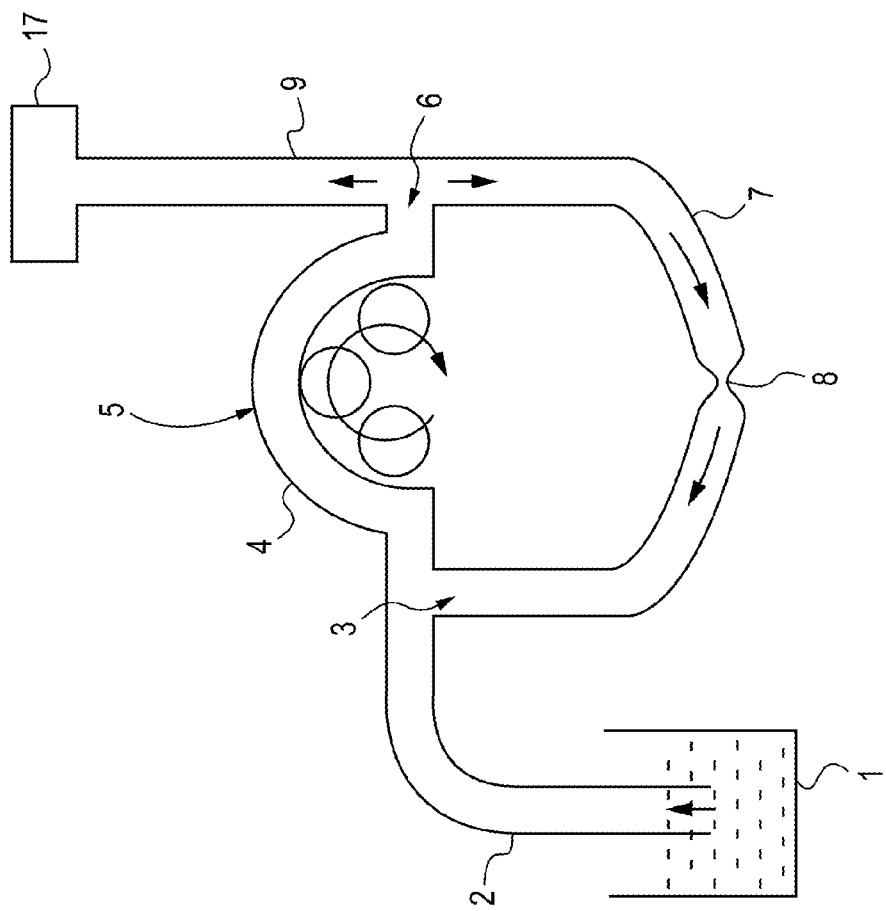
FIG. 3 shows the inflow part of the system along with the inflow peristaltic pump 5, the pressure transducer 17 and the constriction site 8.

In order to clearly understand the system shown in FIG. 2 it would be helpful to discuss the functioning of the inflow peristaltic pump 5 as a separate entity as shown in FIG. 3. The rollers of pump 5 move in the direction of the curved arrow and squeeze over the entire length of peristaltic pump tubing 4. Initially tubes 2, 4, 7 and 9 contain air at atmospheric pressure and the free open end of tube 2 is submerged in a sterile fluid contained inside the fluid source reservoir 1. The moment the constriction site 8 is fully occluded a column of fluid is immediately sucked into tube 4 via tube 2, and thus fluid starts accumulating in the proximal parts of tubes 9 and 7. As the fluid fills in tube 9 it pushes a column of air distal to the fluid column created in tube 9 and the pressure of this compressed air column is sensed by the pressure transducer 17. The fluid pressure and the pressure of the said compressed air column are same thus the pressure transducer 17 actually senses the fluid pressure. If tube 7 continues to remain fully occluded at the constriction site 8, the fluid continues to accumulate inside tubes 9 and in that part of tube 7 which lies between point 6 and the constriction site 8, and the pressure transducer 17 thus displays a continuously rising fluid pressure. The moment the block at the constriction site 8 is partially released the fluid escapes in the form of a jet through the partially open constriction opening 8 in the direction of point 3. With the constriction opening 8 being only partially blocked, if the pump 5 continues to rotate at a constant rotational speed the fluid pressure ultimately gets stabilized at a fixed value provided the internal diameter of the constriction site 8 is not further varied. The diameter D of the constriction site 8 ranges from a minimum non-zero value to a maximum value which is less than the overall diameter of the rest of the housing tube, that is when the constriction site 8 is fully occluded, to a maximum value which is equal to the diameter of tube 7. Henceforth in this manuscript the inner diameter of the constriction site 8 shall be deemed to be fixed at some predetermined value D, unless otherwise stated. The fluid being displaced by the peristaltic pumps is actually pulsatile in nature thus the fluid pressure exhibits minute pulsations having a fixed frequency and a fixed amplitude. From the practical point of view such minute pressure fluctuations of such a regular nature can be ignored in context with distension of body tissue cavities in endoscopic procedures. Henceforth in the entire manuscript the fluid pressure shall be assumed to be non-fluctuating in nature.

Figure 4:
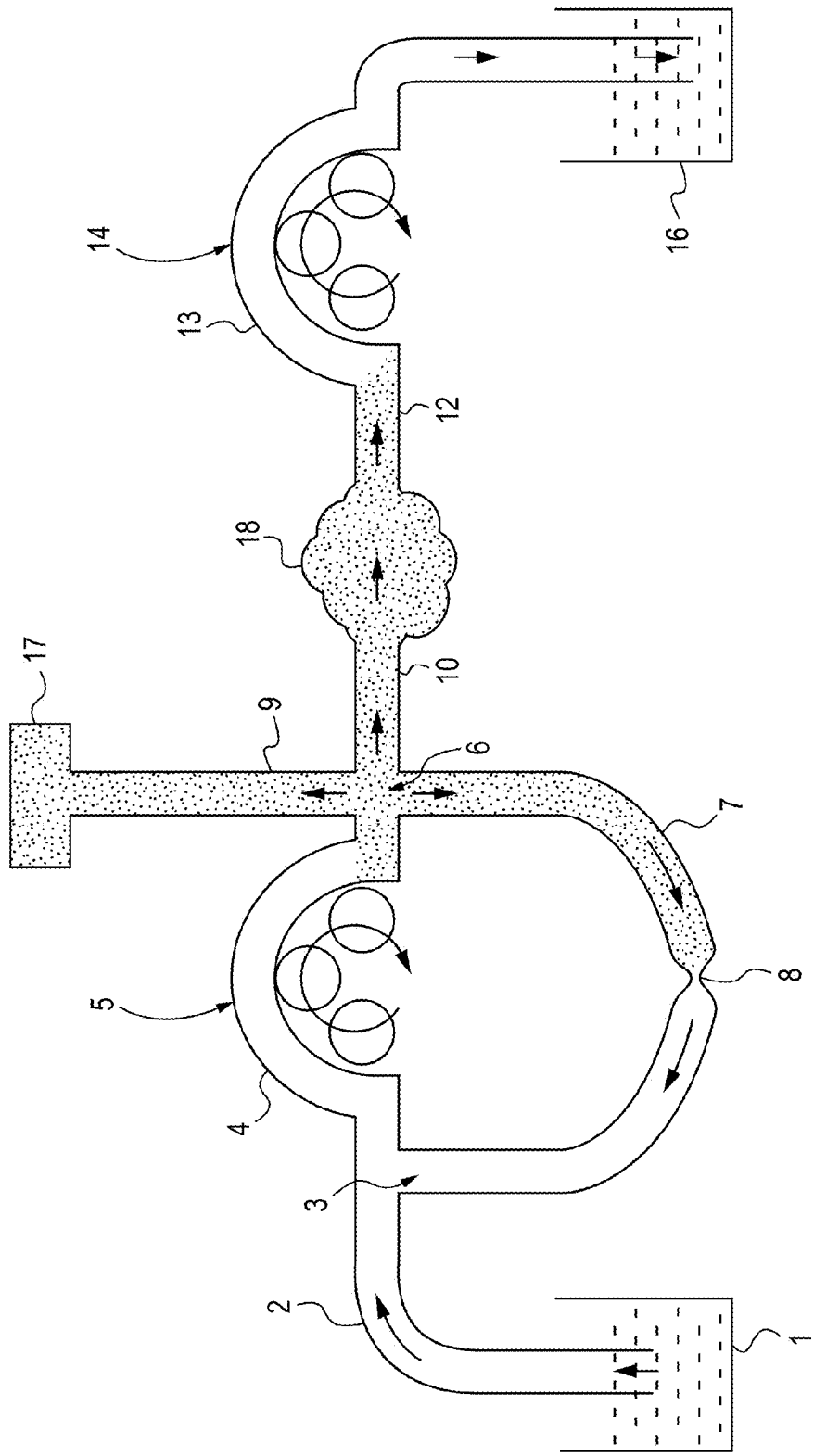
FIG. 4 is similar to FIG. 2 except that in this figure a shaded region represents an area having an almost similar pressure.

Referring to FIG. 4, this figure is similar to FIG. 2 but a limited region of the irrigation circuit having an almost same pressure has been shaded black. Due to frictional resistance experienced by the moving fluid the pressure at point 6, as sensed by the transducer 17, is always found to be higher than the actual pressure inside the tissue cavity 18 but the said pressure difference is so small that it may be neglected from the practical surgical point of view. Also such pressure difference increases as the fluid flow rate increases. In a simulated experimental endoscopic model, as explained hereafter, such pressure difference was found to be only 2 mm Hg at a out flow rate of 500 ml/minute, while at outflow rates less than 400 ml/minute this pressure difference was so small that it had not been possible to demonstrate it experimentally. The term 'out flow rate' being referred to the flow rate of pump 14. Also, the said pressure difference remains constant all through surgery at any fixed outflow rate. Though the said pressure difference is negligible but if desired its effect can also be totally negated by subtracting its value from the pressure reading of the transducer. In this manner, in endoscopic surgeries, it is possible to determine the actual cavity pressure by using the pressure transducer 17 located far away from the cavity. This feature is of special relevance because in endoscopic procedures like hysteroscopy, arthroscopy and brain endoscopic surgery while it is important to know the actual cavity pressure but at the same time it is practically difficult to take a pressure measurement directly from the cavity. The physical principals relating to this have been discussed in detail below.

Referring to FIG. 2 it shall be first described as to how the system of the proposed invention can be used mechanically, that is without a controller. The peristaltic pumps 5 and 14 can be made to work at any fixed rotational speed and the fluid flow rate of each pump is directly proportional to the pump RPM or the pump rotational speed. Thus any precise pump flow rate can be generated by selecting a suitable pump rotational speed. The fluid flow rate of pump 14 shall henceforth be denoted by R2 and shall be termed as the 'outflow rate'. The fluid flow rate of pump 5 shall be denoted by R1 and shall be termed as the 'inflow rate' Here it is to be noted that the term 'inflow rate' R1 is not the true inflow rate for the cavity 18, as might be suggested by the literary meaning of the term 'inflow' because R1 is not the actual rate at which fluid into the cavity 18 because some fluid also constantly escapes through the constriction site opening 8. Henceforth in the entire manuscript the term 'inflow rate' shall only be referred to the flow rate of the inflow pump 5 unless specifically mentioned. However the term 'outflow rate' R2 does correspond to the literary meaning of the term 'outflow' because R2 is equal to the rate at which fluid flows out of the cavity 18. The surgeon initially decides an out flow rate R2 by selecting a suitable rotational speed for pump 14. Next the surgeon decides the maximum flow rate at which fluid could be allowed to enter into the cavity via the inflow tube 10 and the inflow pump 5 is set to work at such flow rate or at a flow rate slightly lesser than this. As discussed in paragraph 26, intravasation is process by which fluid enters into the patient's blood circulation through the cut ends of blood vessels located in the cavity wall or enters into the patient's body, for example into the peritoneal cavity, as a result of an accidental perforation or escapes via patent fallopian tubes into the peritoneal cavity. Thus 'intravasation' is a process by which the pressurized irrigation fluid enters into the patient's body system through the walls of the tissue cavity. In case of a surgical accident like cavity wall perforation the fluid being pumped by the inflow pump 5 can enter into the patient's body at a rate almost equal to R1. It is obvious that the maximum rate of fluid intravasation cannot exceed the value R1. In case of an accident like cavity wall perforation it may take some time before an abnormally high intravasation rate is discovered and in such time a dangerous quantity of fluid might enter into the patient's body. If the inflow rate R1 is kept at a relatively lower value then the volume of intravasated fluid in case of such an accident would be low. After fixing the values for R2 and R1 the system is started and the diameter of the constriction site 8 is gradually reduced. As the diameter of the constriction site 8 is reduced fluid starts flowing into the tissue cavity and the pressure inside the tissue cavity starts rising. When the desired pressure is achieved inside the tissue cavity the diameter of the constriction site 8 is not reduced any further and is fixed. The diameter of the constrictions site at this stage is termed as "D". The constriction site may also be a plastic or metal piece which has a hole in the centre such that the diameter of the hole is permanently fixed at some value D. If a constriction 8 has a permanently fixed diameter then only the flow rates of pumps 14 and 5 have to be set before the system becomes completely operational.

The Inventors here would like to discuss about the importance of incorporating the housing tube 7 with the constriction site and the non-obvious advantages provided by the housing tube 7 with the constriction site.

As mentioned earlier, till date the surgeons were left with only two options, either to ignore the said cavity pressure variations by not correcting them, or to externally and actively correct such pressure variations. To externally and actively correct the variations in the cavity pressure, controller was incorporated and the working of the pumps were essentially controlled by the controller. Incorporation of the controller controlling the operation of the pumps did not provide any benefit. The controllers used to activate the controlling action after the variations in the cavity pressure had subdued. Thus, the controlling action initiated by the controller instead of benefiting the surgeon leads to an undesirable turbulence inside the cavity and also tends to amplify the resultant movement excursions of the cavity walls.

The Inventors have noticed that if the controller continuously controls the operations of the pumps (either on the inflow side or on the outflow side), the cavity pressure continuously fluctuates around a preset value and it not at all possible to attain a constant value. The Inventors believe that the controller provides proper corrective action (by continuously controlling the operations of the pumps) only if the fluctuations in the cavity pressure are gradual and not highly instantaneous. That is, if the quantitative rise/fall in the cavity pressure is over long time period, the controller would be able to provide proper corrective action. As the time period to detect variation in the cavity pressure and commence corrective action is ideally in the range of 2 to 4 seconds, if the quantitative rise/fall in the cavity pressure is over very short time period, the suggested mechanism of providing a controller will be unsuitable. Under such instances, instead of providing any corrective action, the controller destabilizes the system and induces additional pressure fluctuations inside the cavity (because of commencing a corrective action at a delayed stage). Thus it takes very long time period for the system to once again get stabilized.

The Inventors have surprisingly found that by incorporating a housing tube provided with a constriction site at the inflow side as described above, inherently and passively corrects the pressure variations due to physiological cavity wall contractions and the mechanical movement of the tubes and the endoscope and also limits the variation in the size of the cavity. The Applicants would like to highlight that it is important to control both the variations in the pressure inside the cavity and the changes in the size of the distended cavity. Large variations in the pressure inside the cavity or the size of the cavity are detrimental to the surgical procedure. In all the prior art systems attempts were made to either control the variations in the pressure or the variations in the cavity size. But none of the prior art document the need to control both the cavity pressure variations and the cavity size variations and hence failed to provide a safe and ideal system. During the contraction of the cavity, a minute quantity of the fluid is pushed out of the cavity. If during this stage the system does not provide a way for releasing the fluid being pushed out, the instantaneous pressure inside the cavity increases tremendously which is harmful to the patient. On the other hand, if the amount of fluid being pushed out of the cavity is not checked/controlled, the changes in the size of the distended cavity are very high. The incorporation of the housing tube having the constriction site for the first time in the present system controls both the variations in the pressure inside the cavity and the changes in the size of the distended cavity The housing tube having the constrictions site provides a by-pass route for the fluid being pushed out of the cavity to go back to the fluid supply tube or the fluid source reservoir. This avoids the instantaneous pressure surge inside the cavity which is harmful to the patient. The size of the diameter at the constrictions automatically controls the amount of fluid passing through the housing tube, thereby controlling the amount of fluid being pushed out of the cavity. Inclusion of the housing tube with the constrictions site therefore minimizes the instantaneous variations in the size of the distended cavity.

Alternatively if the cavity expands a suitable volume of fluid is sucked into the cavity from the irrigation circuit, such as from the region of point 6, and this is accompanied by a corresponding transient decrease in the flow rate at which fluid which fluid is escaping via the constriction site 8 in the direction of point 3 but if the magnitude of the said physiological expansion is more fluid may even be sucked into the cavity via the constriction site 8. This implies that the constriction site 8 is helping in maintaining a stable cavity pressure despite physiological cavity wall contractions by suitably varying the magnitude of an imaginary fluid flow vector passing through the constriction site 8.

Determining the Real Time Rate of Fluid Intravasation:

Again referring to FIG. 2, let it be hypothetically assumed that the diameter at the constriction site 8 has been fixed at some predetermined value D, the outflow and the inflow rates have been fixed at some values R2 and R1 respectively and in such a situation a pressure P is created inside the tissue cavity 18 when the system is operated. In such a case if no intravasation occurs during the endoscopic procedure then the pressure inside the tissue cavity 18 continues to remain at the same value P. However, if at any stage during the endoscopic procedure intravasation occurs then the cavity pressure immediately falls below the desired initial value P and inflow rate has to be increased by some magnitude in order to raise the cavity pressure to its initial value P. Here magnitude of the required increase in the inflow rate to attain the initial cavity pressure P is equal to the instantaneous real time rate of intravasation R3 existing at that moment of time. In this way the real time rate of fluid intravasation can be determined by using the mechanical version of the proposed invention.

Cavity Pressure or the Outflow Rate, Both Can be Altered Independently without Varying the Value of the Other Parameter:

Referring again to FIG. 2 an hypothetical endoscopic procedure is being considered where surgery is being performed at an outflow rate R2 and inflow rate R1 with the constriction 8 diameter being been fixed at some value D and a resultant cavity pressure P being created maintained. In such hypothetical situation as long as R2 and R1 are not altered the cavity pressure P remains predictably constant throughout surgery resulting in a predictably stable mechanical distension of the tissue cavity walls which culminates in constant clear visualization throughout the endoscopic procedure. If in the said hypothetical procedure the cavity pressure needs to be increased without altering the out flow rate R2 then all that is needed is to start increasing the value of R1 and stop doing so when the desired higher cavity pressure is achieved. Similarly if the cavity pressure needs to be decreased without altering the out flow rate R2 then R1 is decreased till the desired lower cavity pressure is attained. In the said hypothetical endoscopic procedure if the outflow rate R2 needs to be increased without altering the cavity pressure P then the value of R2 is increased by the desired magnitude but simultaneously the value of R1 is also increased by a similar magnitude. Similarly, if the outflow rate R2 needs to be decreased without altering the cavity pressure P then the value of R2 is decreased by the desired magnitude but simultaneously the value of R1 is also decreased by a similar magnitude. Thus if R1 and R2 are simultaneously increased or decreased by the same magnitude the cavity pressure does not vary, the value D is always fixed as already stated. The preceding statements shall now be explained by the help of a numerical hypothetical example. In reference to FIG. 2 considering a hypothetical situation in which an endoscopic procedure is being done at an outflow rate of 100 ml/minute, an inflow rate R1 and the cavity pressure being 80 mm Hg. If the surgeon wants to increase the outflow rate to 322 ml/minute by maintaining the cavity pressure at the same value of 80 mm Hg outflow rate is increased to 322 ml/minute and the inflow rate is increased by 222 ml/minute, because 322 ml/min−100 ml/min=222 ml/minute. As already mentioned in this paragraph if both inflow and outflow rates are increased or decreased by the same magnitude the cavity pressure does not change. Thus the final inflow rate becomes R1+222 ml/minute, where R1 was the initial inflow rate. Thus in the proposed invention the cavity pressure and the outflow rate both can be altered absolutely independent of each other without affecting the value of the other parameter.

Mechanical Version of the Invention:

The mechanical version of the invention shown in FIG. 2 can be used practically in endoscopic surgeries but it requires a skilled operator having a detailed knowledge of the physical principals involved in cavity distension, which may not be always possible. Also the mechanical version has certain practical limitations which shall be explained in the later sections of the manuscript. This mechanical version of the invention has been discussed only in order to explain more clearly the physical principals associated with the controller based version of the invention shown in FIG. 1.

Controller Based Version of the Invention:

Referring to FIG. 1, this figure shows a schematic diagram of the main invention which is proposed to be used in endoscopic procedures. FIG. 1 and FIG. 2 are similar except that in figure except that in FIG. 2 the controller system is not included. A tachometer, not shown in the diagrams, is coupled to each peristaltic pump and sends information regarding the pump rotation speed to the controller 19 via wires 20 and 23. The pump flow rates being proportional to the pump rotation speed the tachometer signal always conveys flow rate related information to the controller. As already mentioned in paragraph 51 both peristaltic pumps have been considered to be similar in all respects because this makes it easier to understand and operate the system. However the two peristaltic pumps may also be different in context with the inner diameter of the peristaltic pump tubes 4 and 13 but in such case suitable modifications have to be made in the controller programming in order to operate the system as described in this manuscript. The controller also regulates the rotation speed of the two pumps via electrical signals sent through wires 24 and 21. The pressure transducer 17 conveys the pressure signal to the controller via wires 22. On the basis of a pressure feed back signal received from the pressure transducer 17 the controller regulates the rotational speed of the inflow pump 5. The outflow pump 14 works at fixed outflow rates and the flow rate of this pump is also regulated by the controller via suitable electrical signals sent via wires 21. A provision exists by which desired values for P and R2 can be fed into the controller and the values R1, R2 and P can be continuously displayed via suitable display means incorporated in the controller. The controller can be programmed to perform many special functions related to endoscopic surgery which shall be discussed in the following paragraphs.

Method of Operating the Controller Based Version of the Invention:

Again referring to FIG. 1, in context with the present invention at the start of surgery the surgeon initially selects suitable values for cavity pressure P and outflow rate R2. The said desired values of P and R2 are fed into the controller via suitable input means incorporated in the controller. The diameter D at the constriction site 8 remains fixed at some pre selected value. The diameter of the constriction site 8 is so chosen that it suits the operational needs of the endoscopic procedure. The method of selecting a suitable diameter D for the constriction site 8 has already been discussed under the heading 'Selection of a suitable diameter for the constriction site'. When the system shown in FIG. 1 is operated the controller 19 instructs the outflow pump 14 via wires 21 to continuously extract fluid out of the body cavity 18 at a desired fixed outflow rate R2. Thus all through the surgery the outflow rate remains fixed at R2 irrespective of any internal or external factors unless intentionally changed by the surgeon. The cavity pressure is sensed by the pressure transducer 17 and a corresponding pressure feedback signal is sent to the controller via wires 22 on the basis of which the controller regulates the inflow rate R1, via wires 24. After the system is made operational the controller 19 gradually increases the inflow rate up to the point where the desired preset cavity pressure P is achieved. Let the value of the inflow rate at which the desired cavity pressure is achieved be termed as 'R1.Final'. It is obvious that the value 'R1.final' is actually determined by the controller by a pressure feed back mechanism and such determination of the value 'R1.Final' is based on the preset values of R2 and P. The controller is so programmed that once the value 'R1.Final' is achieved and is maintained for a desired minimum time interval, for example 10 seconds, after which the controller releases the inflow pump 4 from its pressure feedback control mechanism and allow the inflow pump 4 to operate on its own at an inflow rate 'R1.Final' which was determined by the controller. In this manner the two peristaltic pumps continue to work at fixed flow rates to maintain a desired stable cavity pressure. The controller is also programmed that in case the cavity pressure subsequently alters, for example due to intravasation, by a desired minimum preset magnitude and for a desired minimum time, which may hypothetically be 10 seconds, the inflow pump 4 again comes under the pressure feedback control of the controller and a new value of 'R1.Final' is determined by the controller after which the inflow pump 4 is again allowed to be operated without the pressure feedback mechanism at the newly determined 'R1.Final' inflow rate. Such sequence of events continue to occur throughout the endoscopic procedure. Taking an imaginary example if the total surgical time is 60 minutes then it may be hypothetically possible to operate the inflow pump independent of the pressure feedback mechanism for 55 minutes and under the control of the pressure feedback mechanism for 5 minutes. However, provision of operating the inflow pump 4 under a pressure feedback mechanism all through the endoscopic procedure can also be incorporated.

The Advantage of Operating the Inflow Pump Independent of The Pressure Feedback Mechanism:

The only reason for operating the inflow pump 4 independent of the pressure feedback mechanism is to avoid unnecessary corrections of minor pressure variations caused by physiological cavity wall contractions. The concept of physiological cavity wall contractions has been explained in detail under the heading 'basic physics of cavity distension'. In the present invention the physiological variations in cavity pressure are automatically corrected by the constriction site 8 without the need of a controller. If the cavity contracts a minute quantity of fluid which is pushed out of the cavity escapes via the constriction site 8 towards point 3. It is to be noted that the part of tube 7 between point 8 and 3 is at atmospheric pressure thus the fluid which is expelled from the cavity as a result of a physiological contraction escapes through the constriction site 8 against a zero pressure head, which is at atmospheric pressure. Thus, the transient, insignificant and instantaneous rise/fall in cavity pressure variations get stabilized at the desired preset value within a fraction of seconds. Alternatively if the cavity expands a suitable volume of fluid is sucked into the cavity from the irrigation circuit, such as from the region of point 6, and this is accompanied by a corresponding transient decrease in the flow rate at which fluid which fluid is escaping via the constriction site 8 in the direction of point 3 but if the magnitude of the said physiological expansion is more fluid may even be sucked into the cavity via the constriction site 8. This implies that the constriction site 8 is helping in maintaining a stable cavity pressure despite physiological cavity wall contractions by suitably varying the magnitude of an imaginary fluid flow vector passing through the constriction site 8. Normally the direction of such imaginary vector is always towards point 6 while its magnitude constantly varies to take care of the pressure changes resulting due to physiological cavity contractions. Normally a cavity continuously contracts and dilates by approximately the same magnitudes thus there is no logic to check the minor pressure variations emanating from the said contractions. Also the opening of the constriction site 8 does not allow the said physiological cavity pressure fluctuations to cause any significant cavity wall movement excursions by allowing to and fro movement of flow through its lumen. However, if the said pressure changes are made to be corrected by a controller, as is done in the prior art systems, the cavity wall may exhibit significant irregular pressure fluctuations which may result in significant movement excursions of the cavity wall, thus disallowing a predictably stable mechanical stabilization of the cavity walls. However, in the eventuality of fluid intravasation the fall in cavity pressure drop is relatively more permanent in nature thus needs to be corrected by the controller. As explained in the previous paragraph the controller is so programmed that the inflow pump 4 automatically comes under the pressure feedback control mechanism of the controller in case the cavity pressure alters by a desired minimum preset magnitude and for a desired preset time interval, thus a new 'R1.Final' inflow rate is established at which the inflow pump is again allowed to operate without the feedback control of the controller. As a safety precaution a provision can be made in the controller via suitable input means to fix an upper safe limit for the inflow rate R1 and the cavity pressure P such that these safe limits are riot exceeded accidentally.

Controller Programming for Determining the Instantaneous Rate of Fluid Intravasation During Surgery In the above paragraphs a mechanical method of determining the instantaneous real time instantaneous rate of fluid intravasation without using the controller has been described. However such mechanical evaluation is subject to human error and is also difficult to repeat multiple times during an endoscopic procedure. Hence, the need arises to continuously determine and display the real time rate of fluid intravasation by the help of the controller. Excess fluid intravasation during an endoscopic procedure can even lead to the patient's death thus it is extremely important for the surgeon to reliably, accurately and constantly know the real time rate of fluid intravasation R3 throughout the endoscopic procedure. In order to determine the real time rate of intravasation an equation $KP=(R1-(R2+R3))^2$ has been derived where K=constant, P=cavity pressure, R1=inflow rate, R2=outflow rate and R3=instantaneous rate of fluid intravasation. Let this equation be referred to as equation 1. In equation 1, the values of P, R1 and R2 are always known by the controller and the value of the constant K can be determined by suitable analytical means. Thus in equation 1, R3 is the only unknown value which can be determined by feeding the expression contained in the equation 1 into the controller via suitable programming means and directing the controller to continuously determine and display R3. The controller can be further programmed to carry out multiple other functions related to intravasation such as an alarm being sounded if intravasation of a specific minimum magnitude occurs or if the rate of intravasation rate increases by a specific magnitude. The controller can also be programmed to completely shut down the system in case the rate of intravasation exceeds a specified dangerously high rate. The equation 1 has been derived experimentally, and the said experimental methods are described in the subsequent paragraphs.

Experimental Determination of Equation 1

Figure 5:
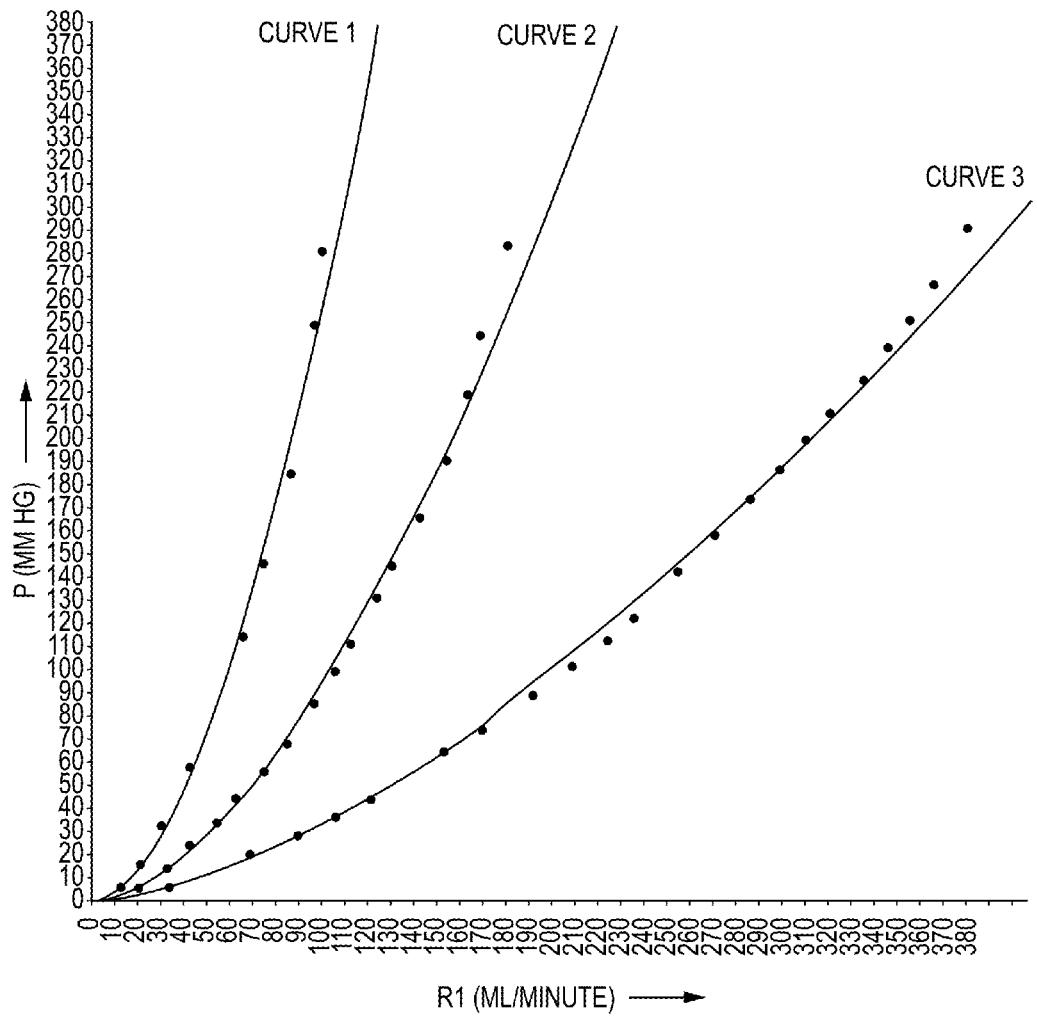
FIG. 5 shows curves 1, 2 and 3.

The equation 1 has been determined by using an experimental setup as shown in FIG. 3. In FIG. 3 the inflow tube 10, the cavity 18, the outflow pump 14, the tube 15 and the waste fluid collecting vessel 16 are not included otherwise FIG. 3 is similar to FIG. 2. The peristaltic pump shown in the experimental set up shown in FIG. 3 was operated by increasing the inflow rate R1 and the corresponding values of R1 and P were plotted on a graph paper. The values R1 were plotted on the X axis while the corresponding values of P were plotted on the Y axis and the said plotted values are represented by small dots in FIG. 5. By the help of a suitable computer programme a curve corresponding to each set of dots was created and superimposed over the said dots. In this manner three curves 1, 2 and 3, were experimentally plotted and are shown in FIG. 5. All of the said dots do not fall exactly over the resultant curve because of mechanical errors and variations associated with practical experimentation. The values of R1 are in 'ml/minute' and correspond to the X axis, while the values of P are in 'mm Hg' and correspond to the Y axis. In order to plot curve 1 the constriction site 8 was substituted by a 20 guage hypodermic injection needle which is used for giving injections to the patients and the experiment as described above was conducted. The curve 2 and 3 were similarly drawn by substituting the constriction site 8 as shown in FIG. 3 by 18 guage and 16 guage hypodermic injection needles respectively. The inner diameter of a 16 guage needle is more than the inner diameter of an 18 guage needle which in turn is more than the inner diameter of a 20 guage needle. The experimental values related to each of the three curves are depicted in table 11 which is as follows:

TABLE 11

Data for curves 1, 2 and 3:

| Curve 1 (Drawn by using 20 guage hypodermic injection needle) | | Curve 2 (Drawn by using 18 Guage hypodermic injection needle) | | Curve 3 (Drawn by using 16 Guage hypodermic injection needle) | |
|---|---|---|---|---|---|
| R1 (ml/min) | P (mm Hg) | R1 (ml/min) | P (mm Hg) | R1 (ml/min) | P (mm Hg) |
| 8 | 2 | 16 | 2 | 22 | 2 |
| 12 | 6 | 20 | 6 | 33 | 6 |
| 21 | 16 | 32 | 14 | 68 | 20 |
| 30 | 32 | 42 | 24 | 88 | 28 |
| 42 | 58 | 54 | 34 | 105 | 35 |
| 64 | 112 | 62 | 44 | 120 | 44 |
| 74 | 144 | 74 | 56 | 152 | 64 |
| 86 | 184 | 84 | 68 | 168 | 74 |
| 96 | 248 | 96 | 82 | 190 | 86 |
| 100 | 280 | 105 | 96 | 208 | 98 |
| | | 112 | 108 | 223 | 110 |
| | | 124 | 128 | 234 | 120 |
| | | 130 | 142 | 254 | 140 |
| | | 142 | 164 | 270 | 156 |
| | | 153 | 190 | 285 | 172 |
| | | 163 | 218 | 298 | 186 |
| | | 168 | 244 | 310 | 198 |
| | | 180 | 282 | 320 | 210 |
| | | | | 335 | 224 |
| | | | | 345 | 238 |
| | | | | 355 | 250 |
| | | | | 365 | 266 |
| | | | | 380 | 290 |

The curves 1, 2 and 3 appear to be parabolas and the mathematical expression for a parabolic curve being $X^2=CY$, where X is a variable related to the X axis, C is a constant and Y is a value related to the Y axis. In order to confirm the parabolic nature of curves 1, 2 and 3 the numerical values related to these three curves were again considered but this time curves were plotted by taking the square values of R1 on the X axis and the values P over the Y axis and the resultant curves 4, 5 and 6 as shown in FIG. 6 are straight line curves cutting the X and the Y axis at zero point. Such mathematical exercise proves the curves 1, 2 and 3 to be parabolas. By substituting R1 and P in the said parabolic expression $X^2=CY$ an equation 2 is derived which is $(R1)^2=KP$ where K is a constant. The numerical values $(R1)^2$ and P taken for plotting curves 4, 5 and 6 are depicted in table 12 which is as follows.

TABLE 12

Data for curves 4, 5 and 6:

| Curve 4 | | Curve 5 | | Curve 6 | |
|---|---|---|---|---|---|
| $(R1)^2$ | P | $(R1)^2$ | P | $(R1)^2$ | P |
| 64 | 2 | 256 | 2 | 484 | 2 |
| 144 | 6 | 400 | 6 | 1089 | 6 |
| 441 | 16 | 1024 | 14 | 4624 | 20 |
| 900 | 32 | 1764 | 24 | 7744 | 28 |
| 1664 | 58 | 2916 | 34 | 11025 | 35 |
| 4096 | 112 | 3844 | 44 | 14400 | 44 |
| 5476 | 144 | 5476 | 56 | 23104 | 64 |
| 7396 | 184 | 7056 | 68 | 28224 | 74 |
| 9216 | 248 | 9216 | 82 | 36100 | 86 |
| 10000 | 280 | 11025 | 96 | 43264 | 98 |
| | | 12544 | 108 | 49729 | 110 |
| | | 15376 | 128 | 54756 | 120 |
| | | 16900 | 142 | 64516 | 140 |
| | | 20164 | 164 | 72900 | 156 |
| | | 23409 | 190 | 81225 | 172 |
| | | 26569 | 218 | 88804 | 186 |
| | | 28224 | 244 | 96100 | 198 |
| | | 32400 | 282 | 102400 | 210 |
| | | | | 112225 | 224 |
| | | | | 119025 | 238 |
| | | | | 126025 | 250 |
| | | | | 133225 | 266 |
| | | | | 144400 | 290 |

Substituting 'R1' BY '(R1−(R2+R3))':

Referring to the equation 2, that is $KP=(R1)^2$, in physical terms R1 is the rate at which fluid fills into tubes 7 and 9 as shown in FIG. 3. But in context with FIG. 2, the rate at which fluid fills into tubes 7 and 9 is equal to (R1−(R2+R3)) because the outflow R2 and the intravasation R3 are two processes which constantly remove fluid from tubes 7 and 9 at a rate R2+R3 while the pump 5 pushes fluid into these tubes at a rate R1. Thus the net rate at which fluid tends to accumulate in the irrigation circuit comprising of the inflow tube 10, the cavity 18 and the outflow tube 12 is equal to (R1−(R2+R3)). In context with FIG. 3 it is extremely important to understand that in actual physical terms R1 is the rate at which fluid tends to accumulate in the irrigation circuit comprising of the tube 9 and that part of tube 7 which lies between point 6 and the constriction point 8. Thus, in context with FIG. 2 the value R1 can be substituted by the value (R1−(R2+R3)). By substituting the value (R1−(R2+R3)) in place of the value R1 in equation 2 the originally proposed main equation 1 is derived, which being $KP=(R1-(R2+R3))_2$.

A Less Accurate Method of Determining the Instantaneous Rate of Fluid Intravasation:

As described in the preceding paragraphs the real time instantaneous rate of fluid intravasation R3 can be accurately determined by using equation 1 and such method is not handicapped by any flow rate or pressure limits. R3 can be determined in a different way also but this method is an inferior and less accurate way of determining R3 and is being mentioned more from the academic point of view and may not necessarily be used in actual practice. In the said less accurate method an equation $P=(K1\times(R1-(R2+R3))+K2$ is used for calculating the value R3 and such equation is being labeled as equation A. In equation A, P is the cavity pressure, K1 is a first constant, R1 is the inflow rate, R2 is the out flow rate, R3 is the real time rate of intravasation and K2 is the second constant. Equation A is a linear expression and can be used for determine R3 within a specific range for cavity pressure and flow rate. In the system shown in FIG. 1 information regarding P, R1 and R2 is constantly available to the controller 19 via wires 22, 23 and 20 respectively. In equation A, R3 is the only unknown value which needs to be determined. On the basis of the linear expression contained the equation A the controller 19 can be programmed to constantly determine and display the value R3. This less accurate method of determining the instantaneous real time rate of fluid intravasation by using the equation $P=(K1\times(R-(R2+R3))+K2$ is also being proposed because such method can facilitate the determination of the real rate of fluid intravasation in the mechanical version of the invention. For financial reasons certain hospitals, especially in developing countries, may be able to afford the mechanical version of the proposed invention. In the prior art systems there is no provision of determining the real time rate of fluid intravasation in the manner described in this manuscript.

Experimental Determination of Equation A:

The curves 1, 2 and 3 shown in FIG. 5 have already been derived using an experimental setup as shown in FIG. 3 and the related experimental steps are described under the heading 'Experimental determination of equation 1'. Referring again to FIG. 5, on close inspection it is seen that a central part of each of the three curves resembles an almost straight line. All three curves can help in the determination of R3, however the curve 3 appears most appropriate for this purpose. Upon careful examination of curve 3 it is seen that a part of this curve lying between the values 70 ml/min to 300 ml/min for R1 and 20 mmHg to 190 mm Hg for P appears almost linear thus for all practical purposes such central part of the parabolic curve 3 may be considered to be an almost straight line.

Figure 7:
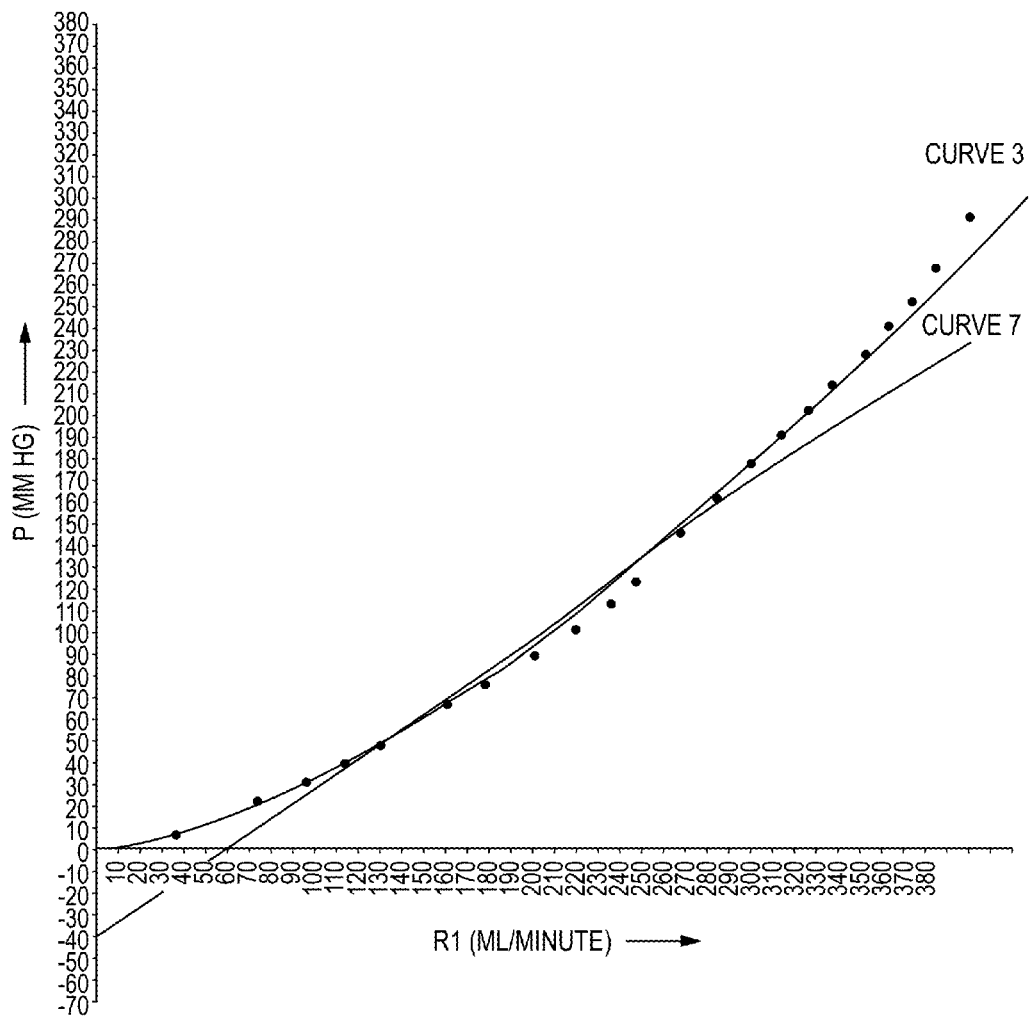
FIG. 7 shows curves 3 and 7.

The values of R1 between 70 ml/min to 300 ml/min and the values of P between 20 mmHg to 190 mm Hg related to curve 3 were plotted separately and an approximate linear approximation for all these values was determined and the same has been labeled as curve 7 as shown in FIG. 7. This straight line curve 7 can be used for determining R3 in an approximate and less accurate manner.

The part of the straight line curve 7 which can be used for determining the real time rate of fluid intravasation in endoscopic surgeries appears to lie between R1=70 to 300 ml/min and P=10 to 170 mm Hg. Curve 7 when extrapolated towards the Y axis cuts the Y axis towards its minus side at a value K2 which being the value of the second constant in equation A. The mathematical expression for curve 7 can be written in the form of equation B which is $P=(K1\times R1)+K2$ where P=pressure measured by the transducer 17, R1=Flow rate of pump 5, K1 is a first constant and K2 is the second constant having a negative value corresponding to the point where the extrapolated part of curve 7 cuts the Y axis. As already explained in paragraph 64 value '(R1−(R2+R3))' can be substituted in place of the value R1. Thus by substituting the value (R1−(R2+R3)) in place of the value R1 in equation B, the original equation A initially proposed in paragraph 65 is derived, the equation being $P=(K^1\times(R1-(R2+R3))+K2$.

Selection of a Suitable Diameter for the Constriction Site:

The three curves drawn in FIG. 5 are not similar because while determining these three curves constriction sites of three different diameters D were used in the experiment. This implies that the shape of such curves is influenced by the value D. Referring to FIG. 5, curve 1 appears unsuitable for endoscopic surgeries because the curve rises very steeply with minimal increase in the inflow rate R1. Curve 3 is very flat and appears relatively more suitable for endoscopic surgeries like hysteroscopy, arthroscopy, transuretheral surgery and other endoscopic surgeries utilizing continuous flow irrigation because in curve 3 a steep rise in the pressure P is not seen even with a substantial increase in the inflow rate R1. As already stated under the heading 'Experimental determination of equation 1', in order to plot curves 1, 2 and 3 the constriction site 8 had been randomly substituted by a 20, 18 and 16 guage by hypodermic injection needles respectively. The diameter of 20 guage needle being is less than the diameter of an 18 gauge needle which is less than the diameter of a 16 guage needle. It is observed that any reduction in the value of D tends to tilt the curve towards the Y axis and while any increase in the value D tends to tilt the curve towards the X axis as shown in FIG. 5. The 20, 18 and 16 gauge needles have been selected at random and there is no specific reason for having selected needles of these particular diameters only, so the selection of guage for the said system should not construed to limit the scope of invention. More such curves can be plotted by increasing the constriction site diameter more than the diameter of a 16 guage needle and the most suitable such curve which fulfills the operational needs of an endoscopic procedure or procedures can be experimentally derived and the constriction site diameter D found associated with the most suitable curve can be permanently substituted in place of the constriction site 8. In this manner the most suitable diameter D for the constriction site 8 can be selected for endoscopic procedure or procedures but such an approach does not take into consideration the operational efficiency needs in context with the cavity pressure fluctuations which might occur due to the inevitable physiological contraction or expansion of the cavity walls. If the diameter of the constriction site 8 is very small then the said transient pressure fluctuation in the cavity pressure would be of a relatively larger magnitude and would last for a relatively longer time interval but the associated resultant movement excursion of the cavity wall would be of a relatively small amplitude. Similarly if the diameter of the constriction site 8 is very large then the said transient cavity pressure fluctuations would be of a relatively smaller magnitude and would last for a relatively shorter time interval but the associated resultant movement excursion of the cavity walls would be of a much larger amplitude. These statements are explained by the help of three hypothetical numerical assumptions as stated in table 13 which is as follows:

TABLE 13

| Serial number of the assumption | A hypothetically assumed numerical value of the constriction site diameter | A hypothetically assumed numerical value of the magnitude of a transient pressure surge associated with a physiological cavity wall contraction movement | A hypothetically assumed time interval for which the said pressure surge exists | A hypothetically assumed magnitude of the associated resultant cavity wall movement excursion |
|---|---|---|---|---|
| 1 | 0.1 mm | 20 mm Hg | 3 seconds | 0.5 mm |
| 2 | 1 mm | 5 mm Hg | 1 second | 1 mm |
| 3 | 1.5 mm | 1 mm Hg | 0.5 seconds | 5 mm Hg |

(*Note:
A similar table can be hypothetically constructed taking into consideration cavity wall expansion, instead of contraction.)

In context with routine endoscopic procedures the above mentioned hypothetical situation associated with serial number 2 is most acceptable out of the three hypothetical examples because a high magnitude cavity wall movement excursion is not at all desirable while a moderately high transient pressure surge may be acceptable in most endoscopic procedures. Thus the nuisance value of a cavity wall movement excursion is relatively more than the nuisance value of the said transient pressure surge. However the amplitude of the pressure surge should also be not very high because it may promote intravasation and other problems.

Thus while selecting the diameter of the constriction site two things are kept in mind, the operational needs of the endoscopic procedure as already explained in this paragraph and the anticipated cavity wall contraction and expansion movements. Thus in those endoscopic procedures where mechanical stability of the cavity walls is important the numerical value of the constriction site diameter D should be relatively smaller. Thus in context with FIG. 5, the fact that slope of curve 3 is relatively less does not make it an ideal curve for all endoscopic procedures because there may be endoscopic precedures where mechanical stability of the cavity walls is the major concern and in such case curve 1 or 2 could be ideal to follow.

Limiting and Predicting Cavity Pressure Surge in Case of Accidental Outflow Obstruction:

If an abnormally high pressure develops inside a tissue cavity during endoscopic surgery it may cause mechanical rupture of the cavity and may also lead to dangerous intravasation. Referring to FIG. 1 if during endoscopic surgery the outflow tube is accidentally blocked the cavity pressure does not increase to dangerous levels because the controller automatically instructs the pump 5 to work at a reduced inflow flow rate, thus a surgical complication is avoided. Referring to the system shown in FIG. 2 if the outflow tube 12 is accidentally blocked the cavity pressure rises to a dangerously high value in the absence of a controller. In context with FIG. 2 an accidental obstruction of the outflow tube or a deliberate obstruction of the inflow tube as achieved by willfully closing the inflow port, both the situations result in a steeply rising pressure as measured by the transducer 17. Thus, while using the mechanical version of the invention as shown in FIG. 2, it is suggested that before starting the endoscopic surgery the surgeon should deliberately blocks the distal end of the inflow tube 10 by closing the inflow port of the endoscope and note the resultant maximum pressure rise. If the resultant pressure is higher than the maximum prescribed safe cavity pressure, then the diameter of the constriction site can be increased by some magnitude such that the resultant pressure created by blocking the inflow tube is well below the maximum safe pressure prescribed for the tissue cavity. In this manner, for a mechanical system as shown in FIG. 2, for a specific inflow rate, the maximum resultant pressure that would develop inside the cavity in the case of a block in the outflow tube can be predictably known and limited. Such method of knowing and limiting the rise in cavity pressure as a result of outflow tube obstruction does not have much role in the controller based version of the invention as shown in FIG. 1. However, even if the controller based version of the invention as shown in FIG. 1 is being used and a high out flow rate is being used then if the outflow tube is suddenly obstructed a transient pressure surge of a relatively small or large amplitude may be experienced before the controller finally stabilizes the inflow pump rotation speed at a significantly reduced value to maintain the initially desired preset cavity pressure. Such pressure surge occurs because initially the pressure transducer senses an exponentially increasing cavity pressure, next a corresponding feedback signal is sent to the controller and the controller finally acts by reducing the rotational speed of the inflow pump and all these actions may take a few seconds to be implemented, especially if the inflow pump was operating at a very high speed of rotation, and in this short time interval a transient surge in the cavity pressure may be experienced. The amplitude of such pressure surge would be small due to the controller feedback mechanism but even a small magnitude surge may damage fragile tissues, for example tissue inside a brain tissue cavity. The amplitude of the said surge can be predictably reduced by suitably increasing the value D. Thus a relatively higher value of D enhances patient safety by predictably limiting the maximum pressure which can develop inside the cavity in case of an accidental obstruction of the outflow tube 12 if the mechanical version of the invention is being used and it also predictably limits the amplitude of any small amplitude pressure surge which might occur when the inflow tube is accidentally blocked while the controller based version of the invention is being used. It has been described in the previous paragraph that the operational efficiency of the system also improves if the value of D is increased. Thus a suitable value of D can be selected by keeping into consideration patient safety and system efficiency. Once a suitable value for D is selected it never altered thereafter as has already been discussed previously. The systems shown in FIGS. 1 and 2 can also have the provision of incorporating multiple constriction sites having different diameters D to suit and accommodate the operational needs of multiple type of endoscopic procedures.

Methods of Shortening the Cavity Refilling Time:

The advantage of shortening the cavity refilling time has already been discussed in paragraph 32 and in the present invention this beneficial maneuver can be carried out by the help of the controller. Referring to FIG. 1, one simple way of reducing the cavity refilling time is by temporarily increasing the fluid flow rate into the cavity while the cavity is being filled. The physical principals related to the said maneuver shall now be described. Referring to FIG. 1 let the difference in the values of R1 and R2 be denoted by a value R which can be stated in equation form as R=R1−R2. Also R1 has to be always more than R2 if any positive cavity pressure is to be maintained. In the system shown in FIG. 1 it is seen that if the cavity pressure is fixed at a preset value P then the value R=R1−R2 also never changes irrespective of the desired outflow rate. The value D is always fixed as already discussed. This implies that in the normal operational mode, for any fixed value of P, the value R=R1−R2 always remains the same. However, when the inflow port is deliberately closed the pressure transducer senses an increased pressure due to which the inflow rate is significantly reduced by the pressure feedback circuit, the outflow rate being always fixed at a value R2. In a mathematical manner it can be stated that if the inflow port is deliberately closed the value R reduces while the pressure value P remains unchanged. A certain minimum reduction in the value R associated with an unchanged P can serve as a trigger which prompts the controller to carry out a specified sequence of events. Let such trigger be termed as 'refilling initiation trigger'. The controller can be so programmed such that upon being prompted by the 'refilling initiation trigger' the controller can carry out any one of the below mentioned three maneuvers A, B or C:

1. Maneuver A: The moment the controller is prompted by a 'refilling initiation trigger' the controller makes the pump 5 to work at some increased flow rate such that a pressure P1, which usually would be higher than the desired cavity pressure, is created and maintained in the inflow circuit proximal to the blocked inflow port. The value of P1 is so selected that when the inflow port is opened after reintroducing the endoscope the cavity gets completely filled up in a desired shorter time interval and at the end of such a maneuver the cavity pressure also should not exceed a prescribed maximum safe cavity pressure or a lower value as desired by the surgeon. Subsequent to opening the inflow port the pressurized fluid accumulated in the inflow circuit enters the cavity in the form of a transient high velocity jet lasting for a few seconds, due to which the cavity gets filled at an accelerated pace thus reducing the total refilling time. The cavity refilling time can thus be reduced by programming the controller to create and maintain a suitable higher value of P1 but it is also important that the value P1 should be low enough such that at the end of the refilling phase, that is when the cavity is completely filled, the pressure inside the cavity does not exceed the maximum prescribed safe cavity pressure. The moment the inflow port is opened the pressurized fluid enters into the cavity and pressure transducer immediately senses a fall in pressure below P1. The controller has to be further programmed that such that any further fall in pressure below P1 should serve as a second trigger which prompts the controller to start working in the normal mode. By normal mode it is meant that the controller functions in order to maintain a desired cavity pressure at a desired outflow rate as was initially decided at the beginning of the surgery. The only draw back in this proposed method of reducing the cavity refilling time is that an accidental kinking of the outflow tube 12 may be wrongly sensed by the controller as deliberately blocking the inflow port. But such accident can be avoided by fixing a suitable upper limit for the cavity pressure or to just accept the remote possibility of such a remote accident but the maximum cavity pressure created in such an eventuality is known and can also be limited. Some hypothetical numerical examples shall be taken in order to further clarify the steps proposed in this paragraph. It is practically seen in hysteroscopy that if the value P1 is taken as 160 mm Hg a uterine cavity having a volume capacity about 20 ml gets filled in approximately 2 seconds and at the end of which a uterine cavity pressure of 60 mm Hg is created. If the cavity had been allowed to fill at a normal flow rate used in actual surgery, for example 50 ml/minute, it would have taken 24 seconds to completely fill a cavity having the same volume capacity. However if a bladder cavity having a large volume capacity of up to 300 ml is substituted in place of the uterine cavity the proposed 'method A' cannot be used for reducing the cavity refilling time. Methods B and C are being proposed to reduce the cavity refilling in the case of large cavities like bladder cavity.

2. Method B: Let us take a hypothetical example of a bladder cavity having volume capacity of 300 ml and the desired cavity pressure while doing the endoscopic surgery being 30 mm Hg. As explained in method A the controller is programmed to create a pressure P1 when the inflow tube is deliberately blocked after withdrawing the endoscope. In method A the opening of the inflow port after again introducing the endoscope into the cavity, serves as the second trigger for the controller to start working in the normal operational mode to maintain a desired cavity pressure and at a specified outflow rate but in method B the controller is programmed differently such that opening the of inflow port after again introducing the endoscope into the cavity should serve as the second trigger which prompts the controller to work at an increased flow rate for a specified time, such time being the calculated time interval in which the cavity would get completely filled, and after the expiry of such specified time the controller being further programmed to start working the system in the normal operational mode. Taking an hypothetical example with numerical values, if the value P1 was taken as 160 mm Hg, as was assumed in method A, then 20 ml fluid shall accumulate inside the bladder cavity in 2 seconds but still 280 ml=300 ml-20 ml more fluid needs to be introduced inside the bladder cavity in order to fill it completely. Hypothetically, the controller may be so programmed that opening of the inflow port should serve as a second trigger to the controller to make the inflow pump 5 work at an inflow rate of 1000 ml/minute for 16.8 seconds. At such flow rate 280 ml fluid can be pushed into the bladder cavity within 16.8 seconds. Had the bladder cavity been filled at an inflow rate of 50 ml/min it would have taken 6 minutes for the cavity to get completely filled where as by resorting to method B the cavity filling time is reduced to 18.8=2+16.8 seconds.

3. Method C: Let the 'refilling initiation trigger' serve only as a trigger which informs the controller that the inflow port has been deliberately blocked and the controller should be so programmed that it allows the inflow pump to continue working in the normal operational mode, that is to maintain the desired cavity pressure. The opening of the inflow port can serve as the second trigger which prompts the controller to make the inflow pump work at an increased flow rate for a specified time and then to again start working in the normal operational mode. This would reduce the cavity refilling time significantly. Taking a hypothetical example similar to the example taken in method B, if opening the inflow port serves as a trigger to make the inflow pump work at a flow rate of 1000 ml/min for 18 seconds then the bladder cavity would get completely filled in 18 seconds.

It is to be noted that in this paragraph the term 'inflow rate' is not the true actual rate which fluid enters into the cavity via the inflow tube because some amount of fluid is also constantly escaping via the opening in the constriction site 8. But the fluid escaping via the opening in the constriction site 8 is very small, especially during the initial part of the cavity refilling phase, thus it can be neglected. Thus in this paragraph the term 'inflow rate' made be deemed to imply the actual cavity inflow rate.

Measurement of the Actual Cavity Pressure:

In the system shown in FIG. 1 and FIG. 2, the value P refers to the actual fluid pressure inside the cavity 18, but in reality P is a pressure value which is sensed by the transducer 17 in the inflow tube, such as at a point 6 which is situated in the upstream part of the inflow tube 10, far away from the cavity. In any system the most convenient place for installing the pressure transducer is inside the main pump housing. As already discussed in paragraph 29 a transducer located in such position may not measure the actual pressure inside the cavity. However in the proposed invention the pressure P measured by the said transducer is only negligibly higher that the actual cavity pressure thus the pressure measured by the said transducer may be considered to represent the actual cavity pressure. In context with determining the actual cavity pressure three experiments were carried out and these experiments are described in the following paragraphs.

'EXPERIMENT 1' TO SHOW THAT 'P' IS ONLY NEGLIGEBLY HIGHER THAN THE ACTUAL CAVITY PRESSURE

Experiment 1 was conducted to demonstrate that the pressure value P measured by the transducer 17 can be considered to represent an almost true cavity pressure, from the surgical point of view. The layout of experiment 1 is similar to the system shown in FIG. 2 except that the inner diameter and length of the inflow and out flow tubes has been specified and in this experiment the cavity pressure has also been measured directly. In experiment 1 the inflow tube 10 is a two meter long rubber tube having an internal diameter of 5 mm, the out flow tube 12 is also a two meter long rubber tube having an inner diameter of 5 mm and the tissue cavity has been substituted by a rigid spherical cavity having approximately the same volume capacity, that is 25 ml, as that of a normal uterine cavity. In this experiment fluid pressures, P2 and P3, have been measured at two different locations by varying the out flow rate R2 between 0 to 600 ml/minute. Let P2 represent the pressure which is measured at a point located high up in the up stream portion of the inflow tube 10, such as point 6. This pressure P2 is measured by the already existing transducer 17. Let P3 represent the actual pressure inside the experimental cavity pressure which is measured directly by inserting a tube into the said experimental cavity and by attaching a transducer at the distal open end of this tube. The transducer and the separate tube which is inserted into the experimental cavity for measuring the actual cavity pressure P3 is not shown in any diagram and has only been hypothetically assumed. Let the difference between P2 and P3 be represented by a value P.diff. This expression can be written in the equation form as P.diff=P2−P3. Experiment 1 was carried out by keeping R2 at seven different values ranging between 0 to 600 ml/minute and the value P.diff was measured for each of the seven values of R2. Also, during the entire experiment 1 the P2 was maintained approximately at 60 mm Hg by suitably increasing or decreasing the flow rate of the inflow pump 5 and the value 60 mm Hg was so chosen as such a pressure value is commonly maintained in endoscopic procedures, however in such an experimental setup the actual value of P2 does not seem to influence the result of experiment 1 which is shown in table 14.

TABLE 14

| R2 (ml/minute) | P.diff (mm Hg) |
| --- | --- |
| 0 | Zero |
| 50 | Zero |
| 130 | Zero |
| 230 | Zero |
| 400 | Zero |
| 500 | 2 |
| 600 | 6 |

It is evident that for the outflow rate between 0 to 400 ml/minute the value P.diff is so small that it had not been possible to elicit it experimentally. At an out flow rate of 500 ml/minute P.diff was found to be 2 mm Hg while at an outflow rate of 600 ml/minute the value of P.diff was 6 mm Hg. Most endoscopic surgeries are done and can be done at outflow rate ranging between 0 to 400 ml/minute and higher flow rates are needed rarely. Even the value 2 mm Hg for P.diff, which is seen at an outflow rate of 500 ml/minute is small enough to be neglected from the surgical point of view. Thus for endoscopic surgeries which are done below 500 ml/minute outflow rate the value P.diff may be considered zero, for all practical purposes.

Experiment 2:

In experiment 1 it is clear that the value P.diff is negligibly small for outflow rates below 500 ml/min. The values P.diff were so small that they could not be determined experimentally.

However in context with experiment 1 a mathematical relationship between R2 and P.diff can only be derived if the values of P.diff are somehow determined experimentally. Thus it was decided to use a 20 meter long tube so that resistance to fluid flow is adequate enough to make it possible to determine the values P.diff via experimental means. For this an experiment 2 was carried out.

The layout for experiment 2 is similar to experiment 1 except that the inflow tube 10, the experimental cavity 18 and the outflow tube 12, all three items were replaced by a single tube 20 meter long, having an internal diameter of 5 mm and extending between the inflow and the outflow pumps. In experiment 2 the pressures P2 and P3 were measured at the proximal part of this 20 meter long tube very near to the outlet end of the inflow pump 5 and at the distal end of this 20 meter tube very near to the inlet end of the outflow pump 14. The experiment was conducted utilizing similar steps as in experiment 1. The results of experiment 2 are given in table 15 which is as follows:

TABLE 15

| R2 (ml/minute) | P. diff (mm Hg) |
| --- | --- |
| 0 | 0 |
| 50 | 4 |

TABLE 15-continued

| R2 (ml/minute) | P. diff (mm Hg) |
|---|---|
| 130 | 10 |
| 230 | 18 |
| 400 | 42 |
| 500 | 44 |
| 600 | 50 |

Figure 8:
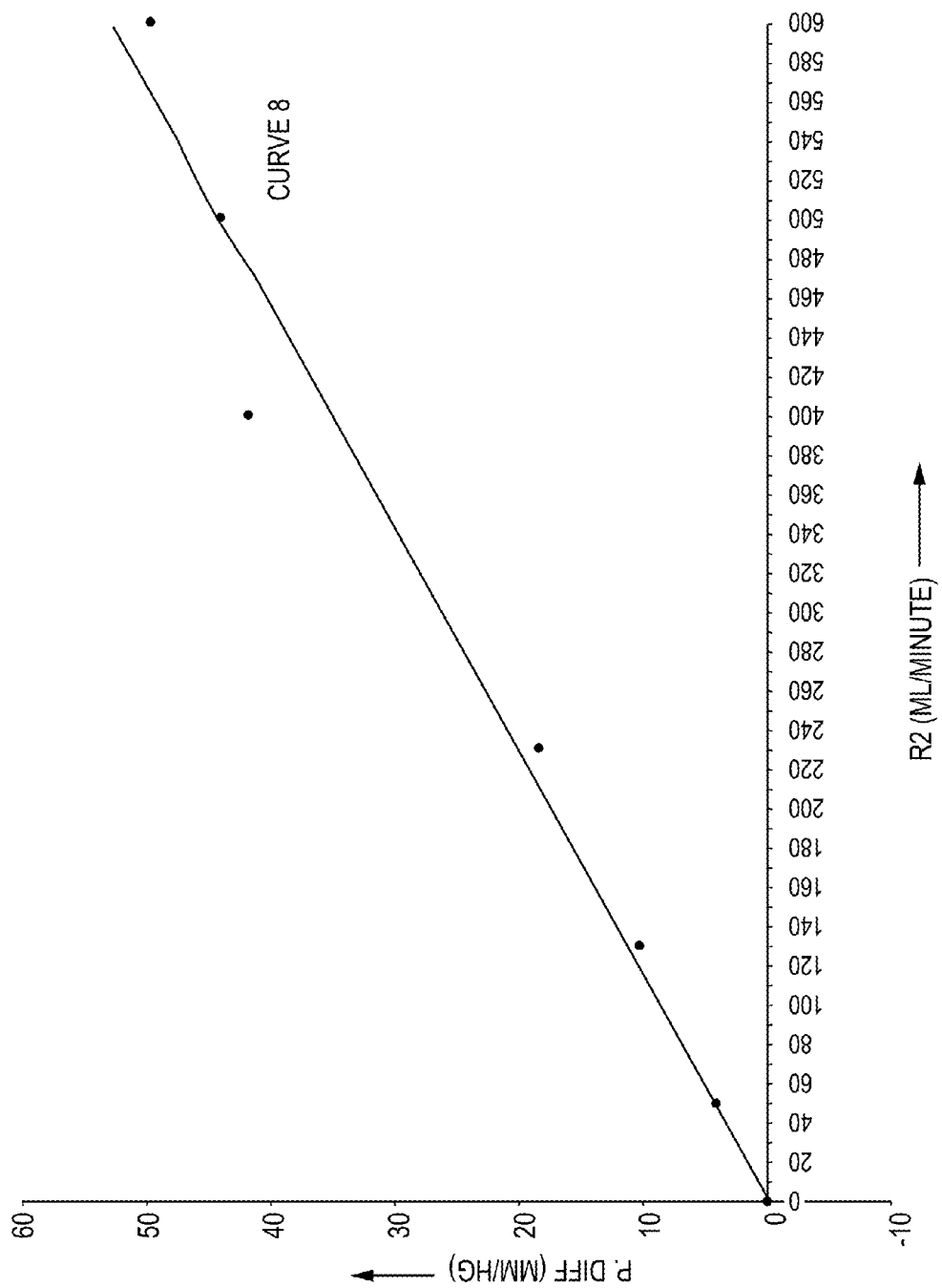
FIG. 8 shows curves 8 and 9.

Referring to table 15 the values of R2 were plotted on the X axis of a graph and the values for P.diff were plotted on the Y axis of the graph and the resultant curve 8 is shown in FIG. 8.

At least in the range of R2 between 0 to 600 ml/min the curve 8 can be considered to be a straight line curve.

For values of R2 greater than 600 ml/min this curve may become non linear but that is not relevant with respect to endoscopic surgery where generally flow rates greater than 600 ml/min are seldom required. The curve 8 can be represented by a mathematical expression R2=A=P.diff where 'A' is a constant. In context with table 13 the values of P.diff can be determined empirically by utilizing more sensitive experimental means and the said determined values of P.diff and R2 in the range 0 tp 600 ml/min can be fed into the controller and the controller can be programmed in a manner that the value P.diff is automatically substracted from the perceived value P, thus the actual cavity pressure is always displayed. In this manner the controller always displays and works at the actual cavity pressure which is determined after taking into consideration the value P.diff as just explained. Thus it can be concluded that the system of the present invention as shown in FIG. 1 can display and work at the actual cavity pressure, irrespective of the outflow rate. It is being possible to determine the actual cavity pressure in the described manner because in the present invention the out flow rate remains constant all through the surgery and is never allowed to vary. If the out flow rate continuously fluctuates as in the prior art systems, the true cavity pressure cannot be measured in the manner just described because irregular variations of the outflow rate are always associated with irregular accelerations and de accelerations of the inflow rate which lead to irregular fluctuations in the value P.diff which does not allow the value P.diff to be measured by the method just described. It may be concluded that in the present invention the surgeon may work at any outflow rates and still know the actual cavity pressure in an extremely reliable manner.

EXPERIMENT 3:

Experiment 3 was carried out to show that the pump 14 which is incorporated on the out flow side of the irrigation circuit also contributes towards reducing the value of P.diff for any same outflow rates. Experiment 3 was carried out using the same experimental setup as used in experiment 1, except that the outflow pump 14 was removed, the outflow tube 12 was made to directly drain into the waste fluid collecting reservoir 16 at atmospheric pressure and the constriction site 8 was fully occluded. In experiment 3, R2 is equal to R1 thus the value R1 is being substituted in place of R2. In experiment 3 the values P.diff were calculated for different values of the inflow rates. The findings of experiment 3 are stated in table 16 which is as follows:

TABLE 16

| R1 (ml/minute) | P. diff (mm Hg) |
|---|---|
| 0 | 0 |
| 50 | 4 |
| 130 | 6 |
| 230 | 8 |

TABLE 16-continued

| R1 (ml/minute) | P. diff (mm Hg) |
|---|---|
| 400 | 10 |
| 500 | 12 |
| 600 | 14 |

By comparing the results of experiment 1 and experiment 3 as given in tables 14 and 16 it is clear that by removing the outflow pump the pressure fall between any two points in the irrigation circuit is reduced. In physical terms it can be stated that by the system of the proposed invention fluid can be transported at a reduced pressure gradient for the same flow rate. A proposed explanation to these experimental observations is that in the proposed invention the fluid flow is somehow acquiring the characteristics of a laminar or streamline flow which is helping in reducing the turbulence in the fluid flow. Though non scientific but it may even be proposed that the fluid in the irrigation circuit is not actually flowing but is being carried enmass by the help of two peristaltic pumps. It may also be proposed that the two peristaltic pumps by consumption of energy are reducing the fluid turbulence. It may also be proposed that the fluid inside the cavity is not actually flowing but is being displaced, the inflow pump pushes some volume in the cavity while the outflow pump simultaneously extracts the same volume of fluid from the cavity. It may also be proposed the system of the proposed invention is somehow contributing by reducing the Reynold number for the flow path. It may also be proposed that the two peristaltic pumps, by the consumption of energy, are somehow reducing the cavity turbulence because theoretically if turbulence is produced by the consumption of energy then it should also be possible to negate turbulence by the consumption of energy.

EXPERIMENT 4: Demonstrates the Effects of Introducing Constrictions in the Irrigation Circuit on The Value P.diff:

In paragraph 61 the inner diameter of the inflow tube, the inflow port, the outflow port and the out flow tube were considered to be uniformly the same and the same has been maintained till now. In routine endoscopic setups it is frequently seen that the diameter of the inflow port is smaller than the diameter of the inflow tube which can be considered as a constriction in the inflow tube, because the inflow tube and the inflow port are in continuity with each other. Experiment 4 was carried out in order to demonstrate the effect of such a constriction on the value P.diff and the steps and the basic layout for experiment 4 being similar to experiment 1. Experiment 4 consists of multiple steps. First, the inner diameter of the inflow port was reduced from 5 mm to 2 mm with all other factors remaining unchanged and the experimental findings are given in table 17 which is as follows:

TABLE 17

| R1 (ml/minute) | P. diff (mm Hg) |
|---|---|
| 0 | Zero |
| 50 | Zero |
| 130 | Zero |
| 230 | Zero |
| 400 | 1 |
| 500 | 3 |
| 600 | 7 |

Next, the inner diameter of the inflow port was maintained at 2 mm but the inner diameter of the out flow port was also reduced to 2 mm and by doing so the experimental findings were found to the same as depicted in the above table 17. Next, the inner diameters of the inflow and the out flow ports were maintained at 2 mm respectively but the inner diameter of the outflow tube was increased from 5 mm to 10 mm and the experimental findings were still the same as shown in table 17. Thus the findings of experiment 4 reveal that the by introducing a constriction in the inflow tube the value P.diff increases by a small magnitude which depends on the magnitude of the constriction diameter. Such effect of introducing a constriction in the inflow circuit on the value P.diff may either be ignored from the practical point of view or such effect may be totally negated by suitably programming the controller as previously described by utilizing the equation R2=A×P.diff. In this manner even in the presence of constrictions inside the inflow tube the controller can be programmed to display and work at the actual cavity pressures. From experiment 4 it is inferred that even if the diameter of the outflow port is reduced but its value is not made lower than the inflow port diameter, the value P.diff does not change. From experiment 4 it is also inferred that increasing the diameter of the outflow tube or the outflow port does not affect the value P.diff. Certain endoscopic surgeries are carried out utilizing miniature endoscopes which have inflow and outflow ports of significantly reduced diameters and in such cases the value P.diff may be appreciably high to be ignored especially at high outflow rates. In such cases it would be extremely useful to negate the effect of P.diff as already described. Thus in the present invention it is possible to continuously determine the actual cavity pressures even if a miniature endoscope is used.

Intraoperatively Switching Between Two or More Types of Irrigation Fluids:

The concept of switching between two or more types of irrigation fluids during an endoscopic procedure has been described in a previous paragraph entitled 'Intraoperatively switching between two types of irrigation fluids'. This concept relates to a maneuver in which a 'first fluid' contained inside the irrigation circuit consisting of the inflow tube and the tissue cavity is replaced by a 'second fluid' in a relatively short time and such being achieved by flushing the said inflow circuit with the 'second fluid' till the point where a desired minimum purity threshold level for the second fluid is achieved. As already explained the minimum purity threshold is the minimum concentration of sodium ions in the second fluid at the end of the flushing phase at which monopolar or bipolar electrosurgery can be carried out. Also as previously discussed a relatively short flushing time is desirable as it reduces the total surgical time and this can be achieved by temporarily increasing the flow rate through the irrigation circuit provided the cavity pressure does not increase during such maneuver because a high pressure may cause the tissue cavity to burst. Taking a hypothetical example let the total volume capacity of the irrigation circuit consisting of the inflow tube and the tissue cavity be equal to a value V which implies that the total volume of the first fluid contained in the said irrigation circuit is V. If the said irrigation circuit is to be flushed by an equivalent volume V of the second fluid in time T then the second fluid needs to flow through the irrigation circuit at a rate which is equal to V divided by T. If a minimum threshold purity of the second fluid is not attained in time T then flushing flow rate can be suitably increased. Let R.flush be the flow rate at which if the irrigation circuit is flushed for a time T then at the end of such flushing a minimum acceptable threshold purity is attained inside the second fluid. R.flush is obviously a high flow rate and if the second fluid is pushed into the inflow tube at such a high flow rate it may cause mechanical rupture of the tissue cavity or a sudden intravasation due to a high pressure which is created inside the cavity by such an act. It has been clearly described previously in the paragraph entitled 'Cavity pressure or the outflow rate, both can be altered independently without varying the value of the other parameter' that if the outflow rate and the inflow rate are increased or decreased by the same magnitude the cavity pressure does not vary. Assuming a hypothetical situation that the system shown in FIG. 1 working at inflow rate R1 and outflow rate R2 generates a cavity pressure P and the system is to be flushed at a higher flow rate 'R.flush'. If the outflow rate in this assumed hypothetical situation is increased to R.flush and the inflow rate is also simultaneously increased by a magnitude R.flush−R2 which implies that the value of the inflow rate is made equal to R1+(R.flush−R2) then the cavity pressure P shall not change. The controller 17 can be programmed that by a single command the out flow rate is increased from R2 to R.flush and the inflow rate is increased from R1 to R1+(R.flush−R2) for a time T. It may be argued that during such an act if the outflow tube gets accidentally blocked the cavity pressure may increase to a dangerously high level and such an accident can be avoided by the pressure feedback mechanism wherein the controller can be additionally programmed that during the cavity flushing phase if an increased cavity pressure is sensed then the said process of cavity flushing is to be immediately stopped. It may also be argued that in FIG. 1 only a single fluid source reservoir 1 and a single fluid supply tube 2 is shown then how it would be possible to deal with two different types of fluids in the system shown in FIG. 1. Such problem can be easily solved by incorporating two separate fluid reservoirs containing different fluids along with two separate suction tubes and suitable clamps capable of blocking the lumen of the suction tubes can be attached to the suction tubes. The clamps can work electromechanically under the influence of the controller such that the clamp related to the right type of fluid opens subsequent to a flushing command being given to the controller and the other clamp keeps the lumen of the second suction tube closed. In FIG. 1 the second fluid reservoir and the second suction tube have deliberately not been shown only to keep the drawing simple. Thus in the proposed invention it is possible to switch between two different types of irrigation fluids intraoperatively by temporarily increasing the flushing flow rate in such a manner that the cavity pressure does not vary during the said flushing maneuver. The proposed invention has obvious use in hysteroscopic surgery, arthroscopic surgery and TURP surgery. The proposed invention can also be utilized for carrying out endoscopic procedures in the brain and the spine. Brain endoscopic surgery also known as neuro endoscopy is a frequently performed life saving procedure. The human brain has got cavities known as the brain ventricles. Many endoscopic procedures are performed by inserting the endoscope into the brain ventricles and many such procedures utilize continuous flow irrigation. Endoscopic surgery of the spine is also a frequently performed and many endoscopic procedures related to the spine utilize continuous flow irrigation. The proposed invention can be useful in other endoscopic procedures also which require continuous flow irrigation. The present invention can be useful in certain non endoscopic procedures also where a tissue cavity needs to be distended by continuous flow irrigation such as phako emulsification and vitrectomy procedures which are related to the eye ball cavity.

The advantage of predicting the required volume for the irrigation fluid at the beginning of the surgery has already been explained. Such maneuver though extremely simple is extremely helpful. In the present invention the outflow rate remains fixed all through the surgery unless intentionally changed by the surgeon. The average total surgical time for similar endoscopic procedures usually does no vary and the surgeons on the basic of their past experience always have an idea of the approximate time which an endoscopic procedure takes. Such time multiplied by the outflow rate R2 gives a fairly accurate idea of the total volume of irrigation which would be consumed in the proposed endoscopic procedure if intravasation was to be ignored and the surgeons again by their past experience also have a fairly rough idea of the of the volume of fluid which is intravasated in a certain duration of time for specific endoscopic procedures. In this manner the total fluid that would be required in a particular endoscopic procedure can be roughly evaluated but even such rough evaluation is helpful as explained in a previous paragraph entitled 'Predicting the total volume of required irrigation fluid'. It is advisable to take a slightly greater volume than that predicted by the method described in this paragraph.

The proposed invention can also be used to impart endoscopic training skills by the help of endoscopic experimental models based on the present invention. Also use and scope of the present invention is not limited to human tissue cavities and it may be used for performing multiple endoscopic procedures in animal tissue cavities also and also for imparting training in endoscopic surgeries related to animal tissue cavities.

It is believed that the foregoing description conveys the best understanding of the objects and the advantages of the present invention. It will be understood by those skilled in the art that numerous improvements and modifications may be made to the embodiments of the invention disclosed herein without departing from the departing from the spirit and scope thereof.

The Invention is Unique

There is no other prior art system in which two peristaltic pumps running simultaneously at fixed flow rates predictably create and maintain any desired fixed pressure inside a tissue cavity, despite unpredictable irregular physiological contractions of the cavity walls, for any precise and fixed outflow rate for unlimited time such that the instantaneous real time rate of fluid intrvasation is constantly known. Besides many other unique features of the invention are stated have already been stated above.

The Heart and Soul of the Invention

The constriction site 8 as described in the manuscript is the heart and soul of the invention without which the invention cannot exist.

The inventors have published a research paper entitled 'A simple technique to reduce fluid intravasation during endometrial resection' in the Feburary 2004 issue of the Journal of the American Association of Gynecologic Laproscopists (see reference 6 i.e. Kumar A, Kumar A: A simple technique to reduce fluid intravasation during endometrial resection. The journal of the American Association of Gynecologic Laproscopists 11(1): 83, 2004). In this study endometrial resections were performed in 539 women using the system of the present invention. During the endometrial resections excess fluid intravasation were detected and prevented from occurring in 20 cases using the feature of the system of the proposed invention which enables the surgeon to always know the instantaneous real time rate of fluid intravasation. Also in all these 539 the inventors could resect the intramural part of the tubal openings successfully in a prospective manner only because of the predictably stable mechanical distension provided by the system of the proposed invention. Such findings have not been published in the past, possibly because such a maneuver is not possible with any of the prior art systems.

The inventors have published another research paper entitled 'Endometrial Tuberculosis' in the February 2004 issue of the Journal of the American Association of Gynecologic Laproscopists (see reference 7 i.e. Kumar A, Kumar A: Endometrial Tuberculosis, The Journal of the American Association of Gynecologic Laproscopists 11(1): 2, 2004). In this study two high quality images of endometrial tuberculosis have been published. It is important to note that it was possible to obtain such high quality images only because the uterine cavity wall could achieve absolute mechanical stability and the uterine cavity pressure could be maintained at a precise stable desired value by using the system of the proposed invention. As of today, besides this study, no other image is available in which the caseous tubercular deposits have been photographed. It is evident that the negligible fluid turbulence provided by the system of the proposed invention prevented such deposits from being washed away.

The inventors have published another research paper entitled 'Microcolpohysteroscopy' in the May 2004 issue of the Journal of the American Association of Gynecologic Laproscopists (see reference 8 i.e. Kumar A, Kumar A: Microcolpohysteroscopy. The Journal of the American Association of Gynecologic Laproscopists 11(2): 131, 2004). In this study, in one of the images it is even possible to see the microvessels inside the microvilli related to the endocervical canal. It is not possible to photograph such minute structures like microvessels unless the cavity wall exhibits absolute mechanical stability which was provided by the system of the proposed invention.

HIGH RESOLUTION, SHARP & HIGH MAGNIFICATION IMAGES were possible to be photographed from the inside of the uterine cavity only due to the less turbulence and predictably stable mechanical distension possible by the proposed invention. Few such images are shown in FIG. 10 and are they are explained herebelow:

Image A and B show tubercular deposits over the endometrium in proven cases of endometrial tuberculosis. The said tubercular deposits could be photographed only because they were not washed away due to negligible turbulence.

Images C and D show retrograde menstruation blood coming out of the tubal openings, a fact which has been reported in text literature but never photographed. These photographs were again possible due to minimal turbulence.

Image E shows the intramural part of the left tubal opening being resected electrosurgically.

The surgeon can have courage to undertake such maneuver only if a predictably stable mechanical distension of the uterine cavity is present.

Image F shows a highly magnified endometrial polyp in the panoramic mode. The afferent and efferent capillary blood vessels of the polyp are also clearly seen due to. It has been possible to capture this image only because of negligible turbulence. Such pedunculated polyps continuously exhibit swaying movements in a turbulent environment as a result of which it is difficult to photograph the microvessels with such clarity.

Advantages of the Proposed Invention

The proposed invention makes endoscopic procedures extremely safe, simple, more accurate and easy to perform. The proposed invention helps the surgeons to perform endoscopic surgeries with greater safety and confidence especially in the initial phase of their learning, curve. Also a distending system based on the proposed invention can be used in multiple endoscopic procedures thus reducing the financial burden on the hospital and the patient. The advantages of proposed invention are summarized in the following table along with the corresponding disadvantages of the prior art systems:

| ADVANTAGES OF THE UTERINE DISTENDING SYSTEM BASED UPON THE PRESENT INVENTION: | DISADVANTAGES OF THE PRIOR ART SYSTEMS: |
| --- | --- |
| It is possible to create and maintain any desired precise tissue cavity pressure for any desired precise fixed outflow rate including a zero outflow rate. | This is not possible in any prior art system. |
| The instantaneous real time rate of fluid intravasation into the patient's body is constantly known without using any type of fluid flow rate sensors. | Such feature is not present in any prior art system. |
| The instantaneous real time rate of fluid intravasation into the patient's body can be determined even mechanically without using a controller and any type of fluid flow rate sensors. | This is not possible in any prior art system. |
| A predictably constant any desired fluid pressure can be maintained inside a tissue cavity for indefinite time. | This is not possible in any prior art system. |
| A predictably constant any desired fluid pressure can be maintained inside a tissue cavity for indefinite time despite physiological cavity wall contractions. | This is not possible in any prior art system. |
| A predictably constant clear endoscopic visualization is possible. | This is not possible in any prior art system. |
| It is possible to achieve a predictably stable mechanical distension of the cavity walls. | This is not possible in any prior art system. |
| It is possible to maintain any desired precise and high cavity pressure without increasing the 'maximum possible fluid intravasation rate'. | This is not possible in any prior art system. |
| It is possible to easily and quickly change over from one type of irrigation fluid to a different type of irrigation fluid during an endoscopic procedure in any desired short period of time such that the cavity pressure does not change during such maneuver. | This is not possible in any prior art system. |

Conclusion

The proposed invention is novel and unique. The invention relates not only to increasing surgical efficiency in certain endoscopic procedures but it also helps in preventing human morbidity and human mortality in many endoscopic procedures. Thus the proposed invention is extremely useful for entire mankind.

We claim:

1. A system for distending body tissue cavities of subjects by continuous flow irrigation during endoscopic procedures, said system comprising:
a fluid source reservoir containing a low viscosity physiologic fluid;
a fluid supply conduit tube connecting the fluid source reservoir to an inlet port of a variable speed positive displacement inflow pump and an outlet port of the said inflow pump being connectable to an inflow port through an inflow tube for pumping the fluid at a controlled flow rate into the body tissue cavity, the flow rate of the said inflow pump being termed as the inflow rate;
an outflow port connectable to an inlet port of a variable speed positive displacement outflow pump through an outflow tube for removing the fluid from the body tissue cavity at a controlled flow rate, the flow rate of the said outflow pump being termed as the outflow rate;
an outlet port of the outflow pump being connected to a waste fluid collecting container;
a tube having a controllable constriction site provided between the fluid source reservoir and the inflow tube such that the tube by-passes the inflow pump, wherein the tube provides a route for any excess fluid being pumped by the inflow pump to bypass the inflow pump to maintain a constant cavity pressure in the body tissue cavity regardless of the outflow rate and without a controller operating the variable speed positive displacement inflow pump and the variable speed positive displacement outflow pump, wherein the constant cavity pressure in the body tissue cavity allows for endoscopic imaging and endoscopic visualization of body tissue cavity walls; and
an endoscope having an imaging device for endoscopic imaging and endoscopic visualization of the body tissue cavity walls while constant cavity pressure is maintained in the body tissue cavity.

2. A system as claimed in claim 1, wherein the fluid source reservoir containing the low viscosity physiologic fluid is maintained at atmospheric pressure or at a pressure greater than the atmospheric pressure.

3. A system as claimed in claim 1, wherein a proximal open end of the fluid supply tube is connected to the fluid source reservoir and a distal end of the tube is connected to the inlet port of the variable speed positive displacement inflow pump.

4. A system as claimed in claim 3, wherein the proximal open end of the fluid supply tube is constantly and completely immersed in the fluid source reservoir.

5. A system as claimed in claim 1, wherein a proximal end of the inflow tube is connected to the outlet port of the variable speed positive displacement inflow pump and a distal end of the inflow tube being connectable to the inflow port.

6. A system as claimed in claim 1, wherein the variable speed positive displacement inflow pump is selected from the group consisting of peristaltic pump, piston pump, gear pump, diaphragm pump and plunger pump.

7. A system as claimed in claim 6, wherein the variable speed positive displacement inflow pump is a peristaltic pump.

8. A system as claimed in claim 1, wherein the tube is releasably provided between the fluid source reservoir and the inflow tube to enable replacement of the tube with another tube having a different diameter at the constriction site to suit the operational need of the endoscopic procedure.

9. A system as claimed in claim 1, wherein a proximal end of the tube is connected to the fluid supply tube near its distal end close to the inlet port of the inflow pump.

10. A system as claimed in claim 1, wherein a distal end of the tube is connected to the inflow tube near its proximal end close to the outlet port of the inflow pump.

11. A system as claimed in claim 1, wherein the tube is provided with a clamping means at the constriction site to enable the user to vary the diameter of the tube at the constriction site to suit the operational needs of endoscopic procedures.

12. A system as claimed in claim 1, wherein the diameter of the tube at the constriction site is in the range of 0.005 mm to a maximum value which is less than the overall diameter of the rest of the tube.

13. A system as claimed in claim 1, wherein the diameter of the tube at the constriction site is in the range of 0.05 to 2.5 mm.

14. A system as claimed in claim 1, further comprising an inflow pressure transducer located between the outlet port of the inflow pump and the inflow port, wherein the inflow pressure transducer is located away from the body tissue cavity, near the outlet port of the inflow pump, such that the actual pressure inside the cavity is measured.

15. A system as claimed in claim 1, wherein a proximal end of the outflow tube is connected to the outlet port and a distal end of the outflow tube is connected to an inlet port of the variable speed positive displacement outflow pump.

16. A system as claimed in claim 1, wherein the variable speed positive displacement outflow pump is selected from the group consisting of peristaltic pump, piston pump, gear pump, diaphragm pump and plunger pump.

17. A system as claimed in claim 16, wherein the variable speed positive displacement outflow pump is a peristaltic pump.

18. A system as claimed in claim 1, wherein the outlet port of the variable speed positive displacement outflow pump is connected to the waste fluid collecting container through a waste fluid carrying tube.

19. A system as claimed in claim 14, further comprising a micro-controller means electrically coupled to the inflow pressure transducer, the inflow pump and the outflow pump for regulating the operation of the inflow and the outflow pumps.

20. A system as claimed in claim 1 further comprising another tube having a variable size constriction site being provided between the outflow tube and the waste fluid collecting container.

21. A system as claimed in claim 18, wherein the fluid supply tube, the inflow tube, the outflow tube and the waste fluid carrying tube are flexible, disposable and are made of polymeric material.

22. A method of distending a body tissue cavity of a subject by continuous flow irrigation, said method comprising the steps of:
(a) dispensing a low viscosity physiologic fluid from a fluid source reservoir to an inflow port through a fluid supply conduit tube, a variable speed positive displacement inflow pump and an inflow tube;
(b) providing the low viscosity physiologic fluid into the body tissue cavity for distending the body tissue cavity of the subject;
(c) removing a waste fluid from the cavity via an outlet port through an outflow conduit tube, a variable speed positive displacement outflow pump and a waste fluid carrying tube;
(d) providing a tube having a controllable constriction site between the fluid source reservoir and the inflow tube such that the tube provides a route for any excess fluid being pumped by the inflow pump to bypass the inflow pump to maintain a constant cavity pressure in the body tissue cavity regardless of the outflow rate and without a controller operating the variable speed positive displacement inflow pump and the variable speed positive displacement outflow pump, wherein the constant cavity pressure in the body tissue cavity allows for endoscopic imaging and endoscopic visualization of body tissue cavity walls. and
(e) performing endoscopic imaging and endoscopic visualization of the body tissue cavity walls while constant cavity pressure is maintained in the body tissue cavity.

23. A system for distending a uterine cavity by continuous flow irrigation during endoscopic procedures, said system comprising:
a fluid source reservoir containing a low viscosity physiologic fluid;
a fluid supply conduit tube connecting the fluid source reservoir to an inlet port of a variable speed positive displacement inflow pump and an outlet port of the said inflow pump being connectable to an inflow port through an inflow tube for pumping the fluid at a controlled flow rate into the uterine cavity, the flow rate of the said inflow pump being termed as the inflow rate;
an outflow port connectable to an inlet port of a variable speed positive displacement outflow pump through an outflow tube for removing the fluid from the uterine cavity at a controlled flow rate, the flow rate of the said outflow pump being termed as the outflow rate;
an outlet port of the outflow pump being connected to a waste fluid collecting container;
a tube having a controllable constriction site provided between the fluid source reservoir and the inflow tube such that the tube by-passes the inflow pump, wherein the tube provides a route for any excess fluid due to physiological contraction of uterine cavity walls to bypass the inflow pump to maintain a constant cavity pressure in the uterine cavity regardless of the outflow rate and without a controller operating the variable speed positive displacement inflow pump and the variable speed positive displacement outflow pump, wherein the constant cavity pressure in the uterine cavity allows for endoscopic imaging and endoscopic visualization of the uterine cavity walls; and
an endoscope having an imaging device for endoscopic imaging and endoscopic visualization of the body tissue cavity walls while constant cavity pressure is maintained in the body tissue cavity.

24. A method of distending a body tissue cavity of a subject by continuous flow irrigation, said method comprising the steps of
(a) dispensing a low viscosity physiologic fluid from a fluid source reservoir to an inflow port through a fluid supply conduit tube, a variable speed positive displacement inflow pump and an inflow tube;
(b) providing the low viscosity physiologic fluid into a body tissue cavity for distending the body tissue cavity of the subject;
(c) removing a waste fluid from the cavity via an outlet port through an outflow conduit tube, a variable speed positive displacement outflow pump and a waste fluid carrying tube;
(d) providing a tube having a controllable constriction site between the fluid source reservoir and the inflow tube such that the tube provides a route for any excess fluid due to physiological contraction of body tissue cavity walls to bypass the inflow pump to maintain a constant cavity pressure in the body tissue cavity regardless of the outflow rate and without a controller operating the variable speed positive displacement inflow pump and the variable speed positive displacement outflow pump, wherein the constant cavity pressure in the body tissue cavity allows for endoscopic imaging and endoscopic visualization of body tissue cavity walls; and (e) performing endoscopic imaging and endoscopic visualization of the body tissue cavity walls while constant cavity pressure is maintained in the body tissue cavity.

* * * * *

UNITED STATES PATENT AND TRADEMARK OFFICE
CERTIFICATE OF CORRECTION

PATENT NO. : 8,652,089 B2
APPLICATION NO. : 10/548950
DATED : February 18, 2014
INVENTOR(S) : Kumar et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2039 days.

Signed and Sealed this
Twenty-ninth Day of September, 2015

Michelle K. Lee
*Director of the United States Patent and Trademark Office*